(12) United States Patent
Chen et al.

(10) Patent No.: US 12,304,955 B2
(45) Date of Patent: *May 20, 2025

(54) ANTIBODIES BINDING PD-1 AND USES THEREOF

(71) Applicant: IMMVIRA CO., LIMITED, Shenzhen (CN)

(72) Inventors: Mingjiu Chen, Hockessin, DE (US); Wei Tan, San Diego, CA (US)

(73) Assignee: Immvira Co., Limited, Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/631,672

(22) Filed: Apr. 10, 2024

(65) Prior Publication Data
US 2024/0270850 A1 Aug. 15, 2024

Related U.S. Application Data

(63) Continuation of application No. 17/047,649, filed as application No. PCT/US2019/027115 on Apr. 12, 2019, now Pat. No. 12,037,395.

(60) Provisional application No. 62/657,927, filed on Apr. 15, 2018.

(51) Int. Cl.
C07K 16/28 (2006.01)
A61P 35/00 (2006.01)
C12N 7/00 (2006.01)

(52) U.S. Cl.
CPC .......... *C07K 16/2818* (2013.01); *A61P 35/00* (2018.01); *C07K 2317/24* (2013.01); *C07K 2317/565* (2013.01); *C07K 2317/74* (2013.01)

(58) Field of Classification Search
None
See application file for complete search history.

(56) References Cited

U.S. PATENT DOCUMENTS

| | | |
|---|---|---|
| 2013/0133091 A1 | 5/2013 | Korman et al. |
| 2015/0017185 A1 | 1/2015 | Akbar et al. |
| 2016/0039921 A1 | 2/2016 | Luo et al. |
| 2018/0011114 A1 | 1/2018 | Nogami et al. |
| 2019/0083555 A1* | 3/2019 | Zhou ............... C12N 15/86 |

FOREIGN PATENT DOCUMENTS

| | | |
|---|---|---|
| RU | 2599417 C2 | 10/2016 |
| WO | 2006121168 A1 | 11/2006 |
| WO | 2014179662 A2 | 11/2014 |
| WO | 2014179664 A2 | 11/2014 |
| WO | 2015112805 A1 | 7/2015 |
| WO | 2016014688 A2 | 1/2016 |
| WO | 2016057841 A1 | 4/2016 |
| WO | 2016092419 A1 | 6/2016 |
| WO | 2017058115 A1 | 4/2017 |
| WO | 2018006005 A1 | 1/2018 |
| WO | 2018053709 | 3/2018 |

OTHER PUBLICATIONS

International Search Report and Written Opinion for International Application No. PCT/US2019/027115 dated Sep. 10, 2019. (9 pages).
Almagro JC, Fransson J. Humanization of antibodies. Front Biosci. Jan. 1, 2008 ;13:1619-33. (Year: 2008).
Chen et al., Enhancement and destruction of antibody function by somatic mutation: unequal occurrence is controlled by V gene combinatorial associations. EMBO J. Jun. 15, 1995;14(12):2784-94. (Year: 1995).
Kussie et al. A single engineered amino acid substitution changes antibody fine specificity. J Immunol. Jan. 1, 1994;152(1): 146-52. (Year: 1994).
Edwards et al. The remarkable flexibility of the human antibody repertoire; isolation of over one thousand different antibodies to a single protein, BLyS. J Mol Biol Nov. 14, 2003;334(1):103-18. (Year: 2003).
Koenig et al. Mutational landscape of antibody variable domains reveals a switch modulating the interdomain conformational dynamics and antigen binding. PNAS Jan. 24, 2017 114(4)E486-E495;first published Jan. 5, 2017. (Year: 2017).

* cited by examiner

*Primary Examiner* — Aurora M Fontainhas
*Assistant Examiner* — Jennifer A Benavides
(74) *Attorney, Agent, or Firm* — Sheppard, Mullin, Richter & Hampton LLP

(57) ABSTRACT

An isolated monoclonal antibody that specifically binds human PD-1. A nucleic acid molecule encoding the antibody, an expression vector, a host cell and a method for expressing the antibody are also provided. The present invention further provides an immunoconjugate, a bispecific molecule, a chimeric antigen receptor, an oncolytic virus and a pharmaceutical composition comprising the antibody, as well as a treatment method using an anti-PD-1 antibody of the invention.

8 Claims, 1 Drawing Sheet
Specification includes a Sequence Listing.

SEQUENCE LISTING

```
Sequence total quantity: 130
SEQ ID NO: 1            moltype = AA   length = 8
FEATURE                 Location/Qualifiers
REGION                  1..8
                        note = VH-CDR1 for C1E1, huC1E1-V1 - huC1E1-V7 and
                         huC1E1-V10
source                  1..8
                        mol_type = protein
                        organism = synthetic construct
SEQUENCE: 1
GFTFSSYL                                                                   8
```

```
SEQ ID NO: 2              moltype = AA   length = 8
FEATURE                   Location/Qualifiers
REGION                    1..8
                          note = VH-CDR2 for C1E1, huC1E1-V1 - huC1E1-V7 and
                           huC1E1-V10
source                    1..8
                          mol_type = protein
                          organism = synthetic construct
SEQUENCE: 2
ISGGGGDT                                                                  8

SEQ ID NO: 3              moltype = AA   length = 13
FEATURE                   Location/Qualifiers
REGION                    1..13
                          note = VH-CDR3 for C1E1, huC1E1-V1 - huC1E1-V7 and
                           huC1E1-V10
source                    1..13
                          mol_type = protein
                          organism = synthetic construct
SEQUENCE: 3
VRFGGAGYYW YFD                                                            13

SEQ ID NO: 4              moltype = AA   length = 8
FEATURE                   Location/Qualifiers
REGION                    1..8
                          note = VH-CDR1 for D1F2
source                    1..8
                          mol_type = protein
                          organism = synthetic construct
SEQUENCE: 4
GFTFSSYT                                                                  8

SEQ ID NO: 5              moltype = AA   length = 8
FEATURE                   Location/Qualifiers
REGION                    1..8
                          note = VH-CDR2 for D1F2
source                    1..8
                          mol_type = protein
                          organism = synthetic construct
SEQUENCE: 5
ISGGGSNI                                                                  8

SEQ ID NO: 6              moltype = AA   length = 13
FEATURE                   Location/Qualifiers
REGION                    1..13
                          note = VH-CDR3 for D1F2
source                    1..13
                          mol_type = protein
                          organism = synthetic construct
SEQUENCE: 6
VLNYAYAMDY WGQ                                                            13

SEQ ID NO: 7              moltype = AA   length = 8
FEATURE                   Location/Qualifiers
REGION                    1..8
                          note = VH-CDR1 for C1F5
source                    1..8
                          mol_type = protein
                          organism = synthetic construct
SEQUENCE: 7
GFAFSSYD                                                                  8

SEQ ID NO: 8              moltype = AA   length = 8
FEATURE                   Location/Qualifiers
REGION                    1..8
                          note = VH-CDR2 for C1F5
source                    1..8
                          mol_type = protein
                          organism = synthetic construct
SEQUENCE: 8
ITGGGSSS                                                                  8

SEQ ID NO: 9              moltype = AA   length = 13
FEATURE                   Location/Qualifiers
REGION                    1..13
                          note = VH-CDR3 for C1F5
source                    1..13
                          mol_type = protein
```

-continued

```
SEQUENCE: 9
ASPYLSYFDY WGQ                                                    13

SEQ ID NO: 10         moltype = AA  length = 8
FEATURE               Location/Qualifiers
REGION                1..8
                      note = VH-CDR1 for D1A1
source                1..8
                      mol_type = protein
                      organism = synthetic construct
SEQUENCE: 10
GFTFSNYA                                                          8

SEQ ID NO: 11         moltype = AA  length = 8
FEATURE               Location/Qualifiers
REGION                1..8
                      note = VH-CDR2 for D1A1
source                1..8
                      mol_type = protein
                      organism = synthetic construct
SEQUENCE: 11
ISGGGGNI                                                          8

SEQ ID NO: 12         moltype = AA  length = 13
FEATURE               Location/Qualifiers
REGION                1..13
                      note = VH-CDR3 for D1A1
source                1..13
                      mol_type = protein
                      organism = synthetic construct
SEQUENCE: 12
ASPYANYVWY LDV                                                    13

SEQ ID NO: 13         moltype = AA  length = 8
FEATURE               Location/Qualifiers
REGION                1..8
                      note = VH-CDR1 for D1F1
source                1..8
                      mol_type = protein
                      organism = synthetic construct
SEQUENCE: 13
GFTFSSNT                                                          8

SEQ ID NO: 14         moltype = AA  length = 8
FEATURE               Location/Qualifiers
REGION                1..8
                      note = VH-CDR2 for D1F1
source                1..8
                      mol_type = protein
                      organism = synthetic construct
SEQUENCE: 14
ISGGGVNT                                                          8

SEQ ID NO: 15         moltype = AA  length = 13
FEATURE               Location/Qualifiers
REGION                1..13
                      note = VH-CDR3 for D1F1
source                1..13
                      mol_type = protein
                      organism = synthetic construct
SEQUENCE: 15
ARHGNYNYYG MDY                                                    13

SEQ ID NO: 16         moltype = AA  length = 8
FEATURE               Location/Qualifiers
REGION                1..8
                      note = VH-CDR1 for C1E2
source                1..8
                      mol_type = protein
                      organism = synthetic construct
SEQUENCE: 16
GYTFTNYW                                                          8

SEQ ID NO: 17         moltype = AA  length = 8
FEATURE               Location/Qualifiers
REGION                1..8
                      note = VH-CDR2 for C1E2
source                1..8
```

-continued

```
                        mol_type = protein
                        organism = synthetic construct
SEQUENCE: 17
IYPGGGYT                                                                8

SEQ ID NO: 18           moltype = AA  length = 13
FEATURE                 Location/Qualifiers
REGION                  1..13
                        note = VH-CDR3 for C1E2
source                  1..13
                        mol_type = protein
                        organism = synthetic construct
SEQUENCE: 18
ARGYGTNYWY FDV                                                         13

SEQ ID NO: 19           moltype = AA  length = 10
FEATURE                 Location/Qualifiers
REGION                  1..10
                        note = VH-CDR1 for C1A1
source                  1..10
                        mol_type = protein
                        organism = synthetic construct
SEQUENCE: 19
GFSLSTSGMG                                                             10

SEQ ID NO: 20           moltype = AA  length = 7
FEATURE                 Location/Qualifiers
REGION                  1..7
                        note = VH-CDR2 for C1A1
source                  1..7
                        mol_type = protein
                        organism = synthetic construct
SEQUENCE: 20
IWWDDDK                                                                7

SEQ ID NO: 21           moltype = AA  length = 13
FEATURE                 Location/Qualifiers
REGION                  1..13
                        note = VH-CDR3 for C1A1
source                  1..13
                        mol_type = protein
                        organism = synthetic construct
SEQUENCE: 21
ARTGGFITTG YWY                                                         13

SEQ ID NO: 22           moltype = AA  length = 8
FEATURE                 Location/Qualifiers
REGION                  1..8
                        note = VH-CDR1 for C1F4
source                  1..8
                        mol_type = protein
                        organism = synthetic construct
SEQUENCE: 22
GYKFTDYA                                                               8

SEQ ID NO: 23           moltype = AA  length = 8
FEATURE                 Location/Qualifiers
REGION                  1..8
                        note = VH-CDR2 for C1F4
source                  1..8
                        mol_type = protein
                        organism = synthetic construct
SEQUENCE: 23
ISTYSGDV                                                               8

SEQ ID NO: 24           moltype = AA  length = 13
FEATURE                 Location/Qualifiers
REGION                  1..13
                        note = VH-CDR3 for C1F4
source                  1..13
                        mol_type = protein
                        organism = synthetic construct
SEQUENCE: 24
SRLGITAGFA YWG                                                         13

SEQ ID NO: 25           moltype = AA  length = 8
FEATURE                 Location/Qualifiers
REGION                  1..8
                        note = VH-CDR1 for D2C2
```

| | | |
|---|---|---|
| source | 1..8<br>mol_type = protein<br>organism = synthetic construct | |
| SEQUENCE: 25<br>GFTFSSNT | | 8 |
| SEQ ID NO: 26<br>FEATURE<br>REGION | moltype = AA  length = 8<br>Location/Qualifiers<br>1..8<br>note = VH-CDR2 for D2C2 | |
| source | 1..8<br>mol_type = protein<br>organism = synthetic construct | |
| SEQUENCE: 26<br>ISGGGVDT | | 8 |
| SEQ ID NO: 27<br>FEATURE<br>REGION | moltype = AA  length = 13<br>Location/Qualifiers<br>1..13<br>note = VH-CDR3 for D2C2 | |
| source | 1..13<br>mol_type = protein<br>organism = synthetic construct | |
| SEQUENCE: 27<br>ARHGNYNYYG MDY | | 13 |
| SEQ ID NO: 28<br>FEATURE<br>REGION | moltype = AA  length = 8<br>Location/Qualifiers<br>1..8<br>note = VH-CDR1 for 2G2 | |
| source | 1..8<br>mol_type = protein<br>organism = synthetic construct | |
| SEQUENCE: 28<br>GFTFSYYG | | 8 |
| SEQ ID NO: 29<br>FEATURE<br>REGION | moltype = AA  length = 8<br>Location/Qualifiers<br>1..8<br>note = VH-CDR2 for 2G2 | |
| source | 1..8<br>mol_type = protein<br>organism = synthetic construct | |
| SEQUENCE: 29<br>ISSGSSFT | | 8 |
| SEQ ID NO: 30<br>FEATURE<br>REGION | moltype = AA  length = 13<br>Location/Qualifiers<br>1..13<br>note = VH-CDR3 for 2G2 | |
| source | 1..13<br>mol_type = protein<br>organism = synthetic construct | |
| SEQUENCE: 30<br>TRREGIYDAS WDY | | 13 |
| SEQ ID NO: 31<br>FEATURE<br>REGION | moltype = AA  length = 8<br>Location/Qualifiers<br>1..8<br>note = VH-CDR1 for C1C5 | |
| source | 1..8<br>mol_type = protein<br>organism = synthetic construct | |
| SEQUENCE: 31<br>GYTFTNYG | | 8 |
| SEQ ID NO: 32<br>FEATURE<br>REGION | moltype = AA  length = 8<br>Location/Qualifiers<br>1..8<br>note = VH-CDR2 for C1C5 | |
| source | 1..8<br>mol_type = protein<br>organism = synthetic construct | |
| SEQUENCE: 32<br>INTYSGEP | | 8 |
| SEQ ID NO: 33<br>FEATURE<br>REGION | moltype = AA  length = 13<br>Location/Qualifiers<br>1..13 | |

```
                        note = VH-CDR3 for C1C5
source                  1..13
                        mol_type = protein
                        organism = synthetic construct
SEQUENCE: 33
VRQGDFDYED AMD                                                         13

SEQ ID NO: 34           moltype = AA  length = 15
FEATURE                 Location/Qualifiers
REGION                  1..15
                        note = VL-CDR1 for C1E1, huC1E1-V1 - huC1E1-V7 and
                         huC1E1-V10
source                  1..15
                        mol_type = protein
                        organism = synthetic construct
SEQUENCE: 34
RASKSVDDSG ISFMH                                                       15

SEQ ID NO: 35           moltype = AA  length = 7
FEATURE                 Location/Qualifiers
REGION                  1..7
                        note = VL-CDR2 for C1E1, huC1E1-V1 - huC1E1-V7 and
                         huC1E1-V10
source                  1..7
                        mol_type = protein
                        organism = synthetic construct
SEQUENCE: 35
AASNQGS                                                                 7

SEQ ID NO: 36           moltype = AA  length = 9
FEATURE                 Location/Qualifiers
REGION                  1..9
                        note = VL-CDR3 for C1E1, huC1E1-V1 - huC1E1-V7 and
                         huC1E1-V10
source                  1..9
                        mol_type = protein
                        organism = synthetic construct
SEQUENCE: 36
HQTKEVPWT                                                               9

SEQ ID NO: 37           moltype = AA  length = 11
FEATURE                 Location/Qualifiers
REGION                  1..11
                        note = VL-CDR1 for D1F2
source                  1..11
                        mol_type = protein
                        organism = synthetic construct
SEQUENCE: 37
RASQDISNFL N                                                           11

SEQ ID NO: 38           moltype = AA  length = 7
FEATURE                 Location/Qualifiers
REGION                  1..7
                        note = VL-CDR2 for D1F2
source                  1..7
                        mol_type = protein
                        organism = synthetic construct
SEQUENCE: 38
YTSRLQS                                                                 7

SEQ ID NO: 39           moltype = AA  length = 9
FEATURE                 Location/Qualifiers
REGION                  1..9
                        note = VL-CDR3 for D1F2
source                  1..9
                        mol_type = protein
                        organism = synthetic construct
SEQUENCE: 39
QQGSSLPWT                                                               9

SEQ ID NO: 40           moltype = AA  length = 11
FEATURE                 Location/Qualifiers
REGION                  1..11
                        note = VL-CDR1 for C1F5
source                  1..11
                        mol_type = protein
                        organism = synthetic construct
SEQUENCE: 40
RASQSISNNL H                                                           11
```

```
SEQ ID NO: 41          moltype = AA   length = 6
FEATURE                Location/Qualifiers
REGION                 1..6
                       note = VL-CDR2 for C1F5
source                 1..6
                       mol_type = protein
                       organism = synthetic construct
SEQUENCE: 41
GSQSMS                                                                    6

SEQ ID NO: 42          moltype = AA   length = 9
FEATURE                Location/Qualifiers
REGION                 1..9
                       note = VL-CDR3 for C1F5
source                 1..9
                       mol_type = protein
                       organism = synthetic construct
SEQUENCE: 42
QQSNSWPLT                                                                 9

SEQ ID NO: 43          moltype = AA   length = 11
FEATURE                Location/Qualifiers
REGION                 1..11
                       note = VL-CDR1 for D1A1
source                 1..11
                       mol_type = protein
                       organism = synthetic construct
SEQUENCE: 43
RASQDISNYL N                                                             11

SEQ ID NO: 44          moltype = AA   length = 7
FEATURE                Location/Qualifiers
REGION                 1..7
                       note = VL-CDR3 for D1A1
source                 1..7
                       mol_type = protein
                       organism = synthetic construct
SEQUENCE: 44
YTSRLHS                                                                   7

SEQ ID NO: 45          moltype = AA   length = 9
FEATURE                Location/Qualifiers
REGION                 1..9
                       note = VL-CDR3 for D1A1
source                 1..9
                       mol_type = protein
                       organism = synthetic construct
SEQUENCE: 45
QQSNALPWT                                                                 9

SEQ ID NO: 46          moltype = AA   length = 15
FEATURE                Location/Qualifiers
REGION                 1..15
                       note = VL-CDR1 for D1F1
source                 1..15
                       mol_type = protein
                       organism = synthetic construct
SEQUENCE: 46
RASESVDNSG ISFMN                                                         15

SEQ ID NO: 47          moltype = AA   length = 7
FEATURE                Location/Qualifiers
REGION                 1..7
                       note = VL-CDR2 for D1F1
source                 1..7
                       mol_type = protein
                       organism = synthetic construct
SEQUENCE: 47
TASNQGS                                                                   7

SEQ ID NO: 48          moltype = AA   length = 9
FEATURE                Location/Qualifiers
REGION                 1..9
                       note = VL-CDR3 for D1F1
source                 1..9
                       mol_type = protein
                       organism = synthetic construct
SEQUENCE: 48
```

```
-continued

QQSYEVPWT                                                                    9

SEQ ID NO: 49          moltype = AA  length = 11
FEATURE                Location/Qualifiers
REGION                 1..11
                       note = VL-CDR1 for C1E2
source                 1..11
                       mol_type = protein
                       organism = synthetic construct
SEQUENCE: 49
KASQSVSNDV A                                                                11

SEQ ID NO: 50          moltype = AA  length = 7
FEATURE                Location/Qualifiers
REGION                 1..7
                       note = VL-CDR2 for C1E2
source                 1..7
                       mol_type = protein
                       organism = synthetic construct
SEQUENCE: 50
YAFHRYT                                                                      7

SEQ ID NO: 51          moltype = AA  length = 9
FEATURE                Location/Qualifiers
REGION                 1..9
                       note = VL-CDR3 for C1E2
source                 1..9
                       mol_type = protein
                       organism = synthetic construct
SEQUENCE: 51
QQDYSSPYT                                                                    9

SEQ ID NO: 52          moltype = AA  length = 11
FEATURE                Location/Qualifiers
REGION                 1..11
                       note = VL-CDR1 for C1A1
source                 1..11
                       mol_type = protein
                       organism = synthetic construct
SEQUENCE: 52
RASQDISNYL I                                                                11

SEQ ID NO: 53          moltype = AA  length = 7
FEATURE                Location/Qualifiers
REGION                 1..7
                       note = VL-CDR2 for C1A1
source                 1..7
                       mol_type = protein
                       organism = synthetic construct
SEQUENCE: 53
YTSRLHS                                                                      7

SEQ ID NO: 54          moltype = AA  length = 9
FEATURE                Location/Qualifiers
REGION                 1..9
                       note = VL-CDR3 for C1A1
source                 1..9
                       mol_type = protein
                       organism = synthetic construct
SEQUENCE: 54
QQHKTLPWT                                                                    9

SEQ ID NO: 55          moltype = AA  length = 11
FEATURE                Location/Qualifiers
REGION                 1..11
                       note = VL-CDR1 for C1F4
source                 1..11
                       mol_type = protein
                       organism = synthetic construct
SEQUENCE: 55
KASQNVRTAV A                                                                11

SEQ ID NO: 56          moltype = AA  length = 7
FEATURE                Location/Qualifiers
REGION                 1..7
                       note = VL-CDR2 for C1F4
source                 1..7
                       mol_type = protein
                       organism = synthetic construct
```

```
SEQUENCE: 56
LASNRHT                                                                      7

SEQ ID NO: 57           moltype = AA  length = 9
FEATURE                 Location/Qualifiers
REGION                  1..9
                        note = VL-CDR3 for C1F4
source                  1..9
                        mol_type = protein
                        organism = synthetic construct
SEQUENCE: 57
LQHWNYPYT                                                                    9

SEQ ID NO: 58           moltype = AA  length = 15
FEATURE                 Location/Qualifiers
REGION                  1..15
                        note = VL-CDR1 for D2C2
source                  1..15
                        mol_type = protein
                        organism = synthetic construct
SEQUENCE: 58
RASESVDNSG ISFMN                                                            15

SEQ ID NO: 59           moltype = AA  length = 7
FEATURE                 Location/Qualifiers
REGION                  1..7
                        note = VL-CDR2 for D2C2
source                  1..7
                        mol_type = protein
                        organism = synthetic construct
SEQUENCE: 59
IASNHGS                                                                      7

SEQ ID NO: 60           moltype = AA  length = 9
FEATURE                 Location/Qualifiers
REGION                  1..9
                        note = VL-CDR3 for D2C2
source                  1..9
                        mol_type = protein
                        organism = synthetic construct
SEQUENCE: 60
QQSYEVPWT                                                                    9

SEQ ID NO: 61           moltype = AA  length = 16
FEATURE                 Location/Qualifiers
REGION                  1..16
                        note = VL-CDR1 for 2G2
source                  1..16
                        mol_type = protein
                        organism = synthetic construct
SEQUENCE: 61
RSSQSIIRSN GNTYLE                                                           16

SEQ ID NO: 62           moltype = AA  length = 7
FEATURE                 Location/Qualifiers
REGION                  1..7
                        note = VL-CDR2 for 2G2
source                  1..7
                        mol_type = protein
                        organism = synthetic construct
SEQUENCE: 62
KVSNRFS                                                                      7

SEQ ID NO: 63           moltype = AA  length = 9
FEATURE                 Location/Qualifiers
REGION                  1..9
                        note = VL-CDR3 for 2G2
source                  1..9
                        mol_type = protein
                        organism = synthetic construct
SEQUENCE: 63
FQGSHVPWT                                                                    9

SEQ ID NO: 64           moltype = AA  length = 16
FEATURE                 Location/Qualifiers
REGION                  1..16
                        note = VL-CDR1 for C1C5
source                  1..16
                        mol_type = protein
```

```
                           organism = synthetic construct
SEQUENCE: 64
RSSQSIVHSN GHIYLE                                                        16

SEQ ID NO: 65           moltype = AA  length = 7
FEATURE                 Location/Qualifiers
REGION                  1..7
                        note = VL-CDR2 for C1C5
source                  1..7
                        mol_type = protein
                        organism = synthetic construct
SEQUENCE: 65
KVSKRFS                                                                  7

SEQ ID NO: 66           moltype = AA  length = 7
FEATURE                 Location/Qualifiers
REGION                  1..7
                        note = VL-CDR3 for C1C5
source                  1..7
                        mol_type = protein
                        organism = synthetic construct
SEQUENCE: 66
FQGSHGT                                                                  7

SEQ ID NO: 67           moltype = AA  length = 121
FEATURE                 Location/Qualifiers
REGION                  1..121
                        note = VH for C1E1
source                  1..121
                        mol_type = protein
                        organism = synthetic construct
SEQUENCE: 67
EVMLVESGGG LVKPGGSLKL SCAASGFTFS SYLMSWVRQT PEKRLEWVAT ISGGGGDTYF         60
PDSVKGRFTI SRDNVKNNLY LQMSSLRSED TALYYCVRFG GAGYYWYFDV WGAGTTVTVS        120
S                                                                      121

SEQ ID NO: 68           moltype = AA  length = 121
FEATURE                 Location/Qualifiers
REGION                  1..121
                        note = VH for huC1E1-V1, huC1E1-V3 - huC1E1-V7
source                  1..121
                        mol_type = protein
                        organism = synthetic construct
SEQUENCE: 68
EVQLVESGGG VVQPGRSLRL SCAASGFTFS SYLMSWVRQA PGKGLEWVAT ISGGGGDTYF         60
PDSVKGRFTI SRDNSKNTLY LQMNSLRAED TAVYYCVRFG GAGYYWYFDV WGAGTLVTVS        120
S                                                                      121

SEQ ID NO: 69           moltype = AA  length = 121
FEATURE                 Location/Qualifiers
REGION                  1..121
                        note = VH for huC1E1-V2 and huC1E1-V10
source                  1..121
                        mol_type = protein
                        organism = synthetic construct
SEQUENCE: 69
EVQLVESGGG VVQPGRSLRL SCAASGFTFS SYLMSWVRQA PGKGLEWVAT ISGGGGDTYF         60
PDSVKGRFTI SRDNSKNTLY LQMNSLRAED TAVYYCVRFG GAGYYWYFDV WGQGTLVTVS        120
S                                                                      121

SEQ ID NO: 70           moltype = AA  length = 117
FEATURE                 Location/Qualifiers
REGION                  1..117
                        note = VH for D1F2
source                  1..117
                        mol_type = protein
                        organism = synthetic construct
SEQUENCE: 70
EVMLVESGGG LVKPGGSLKL SCAASGFTFS SYTMSWVRQT PEKRLEWVAT ISGGGSNIYY         60
PDSVEGRFTV SRDNARNTLY LHMSSLRSED TALYYCVLNY AYAMDYWGQG TSVTVSS          117

SEQ ID NO: 71           moltype = AA  length = 117
FEATURE                 Location/Qualifiers
REGION                  1..117
                        note = VH for C1F5
source                  1..117
                        mol_type = protein
                        organism = synthetic construct
SEQUENCE: 71
```

```
EVQLVESGGG LVKPGGSLKL SCAASGFAFS SYDMSWVRQT PEKRLEWVAY ITGGGSSSFY    60
PDTVKGRFTI SRDNSKNTLY LQMTSLRSED TAMYYCASPY LSYFDYWGQG TTLTVSS     117

SEQ ID NO: 72           moltype = AA  length = 120
FEATURE                 Location/Qualifiers
REGION                  1..120
                        note = VH for D1A1
source                  1..120
                        mol_type = protein
                        organism = synthetic construct
SEQUENCE: 72
EVMLVESGGG LVKPGGSLKL SCAASGFTFS NYAMSWVRQT PEKRLEWVAT ISGGGGNIYY    60
PDSVKGRFTI SRDNARNTLY LQMSSLRSED TALYYCASPY ANYVWYLDVW GAGTTVTVSS   120

SEQ ID NO: 73           moltype = AA  length = 120
FEATURE                 Location/Qualifiers
REGION                  1..120
                        note = VH for D1F1
source                  1..120
                        mol_type = protein
                        organism = synthetic construct
SEQUENCE: 73
EVMLVESGGG LVKPGGSLKL SCAASGFTFS SNTMSWVRQT PEKRLEWVAA ISGGGVNTYY    60
PDSVKGRFTI SRDNARNTLY LQMSSLRSED TALYYCARHG NYNYYGMDYW GQGTSVTVSS   120

SEQ ID NO: 74           moltype = AA  length = 120
FEATURE                 Location/Qualifiers
REGION                  1..120
                        note = VH for C1E2
source                  1..120
                        mol_type = protein
                        organism = synthetic construct
SEQUENCE: 74
QVQLQQSGAE LVRPGTSVKI SCKASGYTFT NYWLGWVKQR PGHGLEWIGD IYPGGGYTNY    60
NENFKGKATL TADTSSSTAY MQLSSLTSED SAVFFCARGY GTNYWYFDVW GAGTTVTVSS   120

SEQ ID NO: 75           moltype = AA  length = 124
FEATURE                 Location/Qualifiers
REGION                  1..124
                        note = VH for C1A1
source                  1..124
                        mol_type = protein
                        organism = synthetic construct
SEQUENCE: 75
QVTLKESGPG ILKPSQTLSL TCSFSGFSLS TSGMGVGWIR QPSGKGLEWL AHIWWDDDKF    60
YNPSLKSQLT ISKDTSRNQV FLKITSVDTA DTATYYCART GGFITTGYWY FDVWGAGTTV   120
TVSS                                                               124

SEQ ID NO: 76           moltype = AA  length = 118
FEATURE                 Location/Qualifiers
REGION                  1..118
                        note = VH for C1F4
source                  1..118
                        mol_type = protein
                        organism = synthetic construct
SEQUENCE: 76
QVQLQQSGAE LVRPGVSVKI SCKGSGYKFT DYAMHWVRQS HAKSLEWIGI STYSGDVSF    60
NQNFKGKATM TVDKSSSTAY MELARLTSED SAIYYCSRLG ITAGFAYWGQ GTLVTVSA    118

SEQ ID NO: 77           moltype = AA  length = 120
FEATURE                 Location/Qualifiers
REGION                  1..120
                        note = VH for D2C2
source                  1..120
                        mol_type = protein
                        organism = synthetic construct
SEQUENCE: 77
EVMLVESGGG LVKPGGSLKL SCAASGFTFS SNTMSWVRQT PEKRLEWVAA ISGGGVDTYY    60
PDSVKGRFTI SRDNARNTLY LQMSSLRSED TALYYCARHG NYNYYGMDYW GQGTSVTVSS   120

SEQ ID NO: 78           moltype = AA  length = 124
FEATURE                 Location/Qualifiers
REGION                  1..124
                        note = VH for 2G2
source                  1..124
                        mol_type = protein
                        organism = synthetic construct
SEQUENCE: 78
EVQLVESGGD LVKPGGSLKL SCTASGFTFS YYGMSWVRQT PDKRLEWVAT ISSGSSFTYS    60
```

```
PDSVKGRFTI SRDNAKNTLY LQMNSLKSED TAIYYCTRRE GIYDASWDYS MDYWGQGTSV    120
TVSS                                                                124

SEQ ID NO: 79           moltype = AA  length = 121
FEATURE                 Location/Qualifiers
REGION                  1..121
                        note = VH for C1C5
source                  1..121
                        mol_type = protein
                        organism = synthetic construct
SEQUENCE: 79
QIQLVQSGPE LKKPGETVKI SCKASGYTFT NYGINWVKQA PGKGLKWMGW INTYSGEPTY    60
SDDFKGRFAF SLETSASTAY LQINNLKNED TSTYFCVRQG DFDYEDAMDY WGQGTSVTVS    120
S                                                                   121

SEQ ID NO: 80           moltype = AA  length = 111
FEATURE                 Location/Qualifiers
REGION                  1..111
                        note = VL for C1E1
source                  1..111
                        mol_type = protein
                        organism = synthetic construct
SEQUENCE: 80
DIVLTQSPAS LAVSLGQRAT ISCRASKSVD DSGISFMHWF QQKPGQPPKL LIYAASNQGS    60
GVPARFRGSG SGTDFSLNIH PMEEDDTAMY FCHQTKEVPW TFGGGTKLEI K             111

SEQ ID NO: 81           moltype = AA  length = 111
FEATURE                 Location/Qualifiers
REGION                  1..111
                        note = VL for huC1E1-V1 and huC1E1-V2
source                  1..111
                        mol_type = protein
                        organism = synthetic construct
SEQUENCE: 81
EIVLTQSPAT LSLSPGERAT LSCRASKSVD DSGISFMHWF QQKPGQPPRL LIYAASNQGS    60
GVPARFSGSG SGTDFTLTIS SLEPEDFAVY FCHQTKEVPW TFGQGTKVEI K             111

SEQ ID NO: 82           moltype = AA  length = 111
FEATURE                 Location/Qualifiers
REGION                  1..111
                        note = VL for huC1E1-V3
source                  1..111
                        mol_type = protein
                        organism = synthetic construct
SEQUENCE: 82
EIVLTQSPAT LSLSPGERAT LSCRASKSVD DSGISFMHWY QQKPGQPPRL LIYAASNQGS    60
GVPARFSGSG SGTDFTLTIS SLEPEDFAVY FCHQTKEVPW TFGQGTKVEI K             111

SEQ ID NO: 83           moltype = AA  length = 111
FEATURE                 Location/Qualifiers
REGION                  1..111
                        note = VL for huC1E1-V4
source                  1..111
                        mol_type = protein
                        organism = synthetic construct
SEQUENCE: 83
EIVLTQSPAT LSLSPGERAT LSCRASKSVD DSGISFMHWF QQKPGQAPRL LIYAASNQGS    60
GVPARFSGSG SGTDFTLTIS SLEPEDFAVY FCHQTKEVPW TFGQGTKVEI K             111

SEQ ID NO: 84           moltype = AA  length = 111
FEATURE                 Location/Qualifiers
REGION                  1..111
                        note = VL for huC1E1-V5
source                  1..111
                        mol_type = protein
                        organism = synthetic construct
SEQUENCE: 84
EIVLTQSPAT LSLSPGERAT LSCRASKSVD DSGISFMHWF QQKPGQPPRL LIYAASNQGS    60
GIPARFSGSG SGTDFTLTIS SLEPEDFAVY FCHQTKEVPW TFGQGTKVEI K             111

SEQ ID NO: 85           moltype = AA  length = 111
FEATURE                 Location/Qualifiers
REGION                  1..111
                        note = VL for huC1E1-V6
source                  1..111
                        mol_type = protein
                        organism = synthetic construct
SEQUENCE: 85
EIVLTQSPAT LSLSPGERAT LSCRASKSVD DSGISFMHWF QQKPGQPPRL LIYAASNQGS    60
```

```
GVPARFSGSG SGTDFTLTIS SLEPEDFAVY YCHQTKEVPW TFGQGTKVEI K          111

SEQ ID NO: 86           moltype = AA  length = 111
FEATURE                 Location/Qualifiers
REGION                  1..111
                        note = VL for huC1E1-V7 and huC1E1-V10
source                  1..111
                        mol_type = protein
                        organism = synthetic construct
SEQUENCE: 86
EIVLTQSPAT LSLSPGERAT LSCRASKSVD DSGISFMHWY QQKPGQAPRL LIYAASNQGS  60
GIPARFSGSG SGTDFTLTIS SLEPEDFAVY YCHQTKEVPW TFGQGTKVEI K          111

SEQ ID NO: 87           moltype = AA  length = 107
FEATURE                 Location/Qualifiers
REGION                  1..107
                        note = VL for D1F2
source                  1..107
                        mol_type = protein
                        organism = synthetic construct
SEQUENCE: 87
DIQMTQTTSS LSASLGDRVT ISCRASQDIS NFLNWYQQKP DGTVKLLIYY TSRLQSGVPS  60
RFSGTGSGTD YSLTISNLEQ EDLATYFCQQ GSSLPWTFGG GTKLEIK              107

SEQ ID NO: 88           moltype = AA  length = 107
FEATURE                 Location/Qualifiers
REGION                  1..107
                        note = VL for C1F5
source                  1..107
                        mol_type = protein
                        organism = synthetic construct
SEQUENCE: 88
DIVLTQSPAT LSVTPGDSVS LSCRASQSIS NNLHWYQQKS HESPRLLIKY GSQSMSGIPS  60
RFSGSGSGTD FTLVINSVET EDFGMYFCQQ SNSWPLTFGA GTKLELK              107

SEQ ID NO: 89           moltype = AA  length = 107
FEATURE                 Location/Qualifiers
REGION                  1..107
                        note = VL for D1A1
source                  1..107
                        mol_type = protein
                        organism = synthetic construct
SEQUENCE: 89
DIQMTQTTSS LSASLGDRVT ISCRASQDIS NYLNWYQQKP DGTVKLLIYY TSRLHSGVPS  60
RFSGSGSGTD FSLTISNLEE EDIATYFCQQ SNALPWTFGG GTKLEIK              107

SEQ ID NO: 90           moltype = AA  length = 111
FEATURE                 Location/Qualifiers
REGION                  1..111
                        note = VL for D1F1
source                  1..111
                        mol_type = protein
                        organism = synthetic construct
SEQUENCE: 90
DIVLTQSPAS LVVSLGQRAT ISCRASESVD NSGISFMNWF QQKPGQPPKL LIYTASNQGS  60
GVPARFSGSG SGTDFSLNIH PMEEDDSAMY FCQQSYEVPW TFGGGTKLEI K          111

SEQ ID NO: 91           moltype = AA  length = 107
FEATURE                 Location/Qualifiers
REGION                  1..107
                        note = VL for C1E2
source                  1..107
                        mol_type = protein
                        organism = synthetic construct
SEQUENCE: 91
SIVMTQTPKF LLVSAGDRVT ITCKASQSVS NDVAWYQQKP GQSPKLLIYY AFHRYTGVPD  60
RFTGSGYGTD FTFTISTVQA EDLAVYFCQQ DYSSPYTFGG GTKLEIK              107

SEQ ID NO: 92           moltype = AA  length = 107
FEATURE                 Location/Qualifiers
REGION                  1..107
                        note = VL for C1A1
source                  1..107
                        mol_type = protein
                        organism = synthetic construct
SEQUENCE: 92
DIQMTQTTSS LSASLGDRVT ISCRASQDIS NYLIWYQQKT DGTLKLLIYY TSRLHSGVPS  60
RFSGSGSGTD YSLTISNLEQ EDIATYFCQQ HKTLPWTFGG GTKLEIK              107
```

```
SEQ ID NO: 93                  moltype = AA   length = 107
FEATURE                        Location/Qualifiers
REGION                         1..107
                               note = VL for C1F4
source                         1..107
                               mol_type = protein
                               organism = synthetic construct
SEQUENCE: 93
DIVMTQSQKF MSTSVGDRVT ITCKASQNVR TAVAWYQQKP GQSPKALIYL ASNRHTGVPD    60
RFTGSGSGTD FTLTISNVQS KDLADYFCLQ HWNYPYTFGG GTKLEIK                 107

SEQ ID NO: 94                  moltype = AA   length = 111
FEATURE                        Location/Qualifiers
REGION                         1..111
                               note = VL for D2C2
source                         1..111
                               mol_type = protein
                               organism = synthetic construct
SEQUENCE: 94
DIVLTQSPAS LAVSLGQRAT ISCRASESVD NSGISFMNWF QQKPGQSPKL LIYIASNHGS    60
GVPARFSGSG SGTDFSLNIH PMEEDDSAMY FCQQSYEVPW TFGGGTKLEI K            111

SEQ ID NO: 95                  moltype = AA   length = 112
FEATURE                        Location/Qualifiers
REGION                         1..112
                               note = VL for 2G2
source                         1..112
                               mol_type = protein
                               organism = synthetic construct
SEQUENCE: 95
DVLMTQTPLS LPVSLGDQAS ISCRSSQSII RSNGNTYLEW YLQKPGQSPK LLIYKVSNRF    60
SGVPDRFSGS GSGTDFTLKI SRVEADDLGL YYCFQGSHVP WTFGGGTKLE IK           112

SEQ ID NO: 96                  moltype = AA   length = 110
FEATURE                        Location/Qualifiers
REGION                         1..110
                               note = VL for C1C5
source                         1..110
                               mol_type = protein
                               organism = synthetic construct
SEQUENCE: 96
DVLMTQSPLS LPVSLGDQAS ISCRSSQSIV HSNGHIYLEW YLQKPGQSPK LLIYKVSKRF    60
SGVPDRFSGS GSGTDFTLKI SRVEAEDLGV YYCFQGSHGT FGGGTKLEIK              110

SEQ ID NO: 97                  moltype = AA   length = 330
FEATURE                        Location/Qualifiers
REGION                         1..330
                               note = human IgG1 heavy chain constant region
source                         1..330
                               mol_type = protein
                               organism = synthetic construct
SEQUENCE: 97
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 98                  moltype = AA   length = 107
FEATURE                        Location/Qualifiers
REGION                         1..107
                               note = human kappa light chain constant region
source                         1..107
                               mol_type = protein
                               organism = synthetic construct
SEQUENCE: 98
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 99                  moltype = AA   length = 98
FEATURE                        Location/Qualifiers
REGION                         1..98
                               note = human IgG1 heavy chain CH1 region
source                         1..98
                               mol_type = protein
                               organism = synthetic construct
SEQUENCE: 99
ASTKGPSVFP LAPSSKSTSG GTAALGCLVK DYFPEPVTVS WNSGALTSGV HTFPAVLQSS    60
```

```
GLYSLSSVVT VPSSSLGTQT YICNVNHKPS NTKVDKKV                                  98

SEQ ID NO: 100              moltype = AA  length = 371
FEATURE                     Location/Qualifiers
source                      1..371
                            mol_type = protein
                            organism = Homo sapiens
SEQUENCE: 100
LDSPDRPWNP PTFSPALLVV TEGDNATFTC SFSNTSESFV LNWYRMSPSN QTDKLAAFPE           60
DRSQPGQDCR FRVTQLPNGR DFHMSVVRAR RNDSGTYLCG AISLAPKAQI KESLRAELRV          120
TERRAEVPTA HPSPSPRPAG QFQEPKSCDK THTCPPCPAP ELLGGPSVFL FPPKPKDTLM          180
ISRTPEVTCV VVDVSHEDPE VKFNWYVDGV EVHNAKTKPR EEQYNSTYRV VSVLTVLHQD          240
WLNGKEYKCK VSNKALPAPI EKTISKAKGQ PREPQVYTLP PSREEMTKNQ VSLTCLVKGF          300
YPSDIAVEWE SNGQPENNYK TTPPVLDSDG SFFLYSKLTV DKSRWQQGNV FSCSVMHEAL          360
HNHYTQKSLS L                                                              371

SEQ ID NO: 101              moltype = AA  length = 453
FEATURE                     Location/Qualifiers
source                      1..453
                            mol_type = protein
                            organism = Homo sapiens
SEQUENCE: 101
FTVTVPKDLY VVEYGSNMTI ECKFPVEKQL DLAALIVYWE MEDKNIIQFV HGEEDLKVQH           60
SSYRQRARLL KDQLSLGNAA LQITDVKLQD AGVYRCMISY GGADYKRITV KVNAPYNKIN          120
QRILVVDPVT SEHELTCQAE GYPKAEVIWT SSDHQVLSGK TTTTNSKREE KLFNVTSTLR          180
INTTTNEIFY CTFRRLDPEE NHTAELVIPE LPLAHPPNER TEPKSCDKTH TCPPCPAPEL          240
LGGPSVFLFP PKPKDTLMIS RTPEVTCVVV DVSHEDPEVK FNWYVDGVEV HNAKTKPREE          300
QYNSTYRVVS VLTVLHQDWL NGKEYKCKVS NKALPAPIEK TISKAKGQPR EPQVYTLPPS          360
REEMTKNQVS LTCLVKGFYP SDIAVEWESN GQPENNYKTT PPVLDSDGSF FLYSKLTVDK          420
SRWQQGNVFS CSVMHEALHN HYTQKSLSLS PGK                                      453

SEQ ID NO: 102              moltype = DNA  length = 363
FEATURE                     Location/Qualifiers
misc_feature                1..363
                            note = VH for C1E1
source                      1..363
                            mol_type = other DNA
                            organism = synthetic construct
SEQUENCE: 102
gaagtgatgc tggtggagtc tgggggaggg ttagtgaagc ctggagggtc cctgaaactc           60
tcctgtgcag cctctggatt cacgttcagt agttatctta tgtcttgggt tcgccagact         120
ccggagaaga ggctggagtg ggtcgcaacc attagtggtg gtggtggtga cacctacttt         180
ccagacagtg tgaagggtcg attcaccatc tccagagaca atgtcaagaa caacctgtat         240
ctgcaaatga gcagtcttag gtctgaggac acggccttgt attactgtgt aagatttggg         300
ggcgctggtt actactggta tttcgatgtc tggggcgcag ggaccacggt caccgtctcc         360
tca                                                                       363

SEQ ID NO: 103              moltype = DNA  length = 363
FEATURE                     Location/Qualifiers
misc_feature                1..363
                            note = VH for huC1E1-V2 and huC1E1-V10
source                      1..363
                            mol_type = other DNA
                            organism = synthetic construct
SEQUENCE: 103
gaggtgcagc tggtggagtc tgggggaggc gtggtccagc ctggagggtc cctgagactc           60
tcctgtgcag cctctggatt caccttcagt agctatctta tgtcctgggt ccgccaggct         120
ccaggcaagg ggctagagtg ggtggcaact atatcaggtg gtggaggtga cacatacttc         180
ccagactccg tgaagggccg attcaccatc tccagagaca attccaagaa cacgctgtat         240
ctgcaaatga acagcctgag agctgaggac acggctgtgt attactgtgt gagattcggt         300
ggtgctggtt actactggta ctttgacgtc tggggccaag gaaccctggt caccgtctcg         360
agt                                                                       363

SEQ ID NO: 104              moltype = DNA  length = 351
FEATURE                     Location/Qualifiers
misc_feature                1..351
                            note = VH for D1F2
source                      1..351
                            mol_type = other DNA
                            organism = synthetic construct
SEQUENCE: 104
gaagtgatgc tggtggagtc tgggggaggc ttagtgaagc ctggagggtc cctgaaactc           60
tcctgtgcag cctctggatt cactttcagt agctatacca tgtcttgggt tcgccagact         120
ccggagaaga ggctggagtg ggtcgcaacc attagtggtg gtggtagtaa catctactat         180
ccagacagtg tggagggtcg attcaccgtc tccagagaca atgccaggaa caccctgtac         240
ctgcatatga gcagtctgag gtctgaggac acggcctat attactgtgt ccttaactac          300
gcctatgcta tggactactg gggtcaagga acctcagtca ccgtctcctc a                  351

SEQ ID NO: 105              moltype = DNA  length = 351
```

| FEATURE | Location/Qualifiers |
|---|---|
| misc_feature | 1..351 |
| | note = VH for C1F5 |
| source | 1..351 |
| | mol_type = other DNA |
| | organism = synthetic construct |

SEQUENCE: 105

```
gaagtgcagc tggtggagtc tggggggaggc ttagtgaagc ctggagggtc cctgaaactc    60
tcctgtgcag cctctggatt cgctttcagt agctatgaca tgtcttgggt tcgccagact   120
ccggagaaga ggctggagtg ggtcgcatac attactggtg gtggtagtag ttccttctat   180
ccagacactg tgaagggccg attcaccatc tccagagaca attccaagaa caccctgtat   240
ttgcaaatga ccagtctgag gtctgaggac acagccatgt attactgtgc aagcccctac   300
ttatcctact ttgactactg gggccaaggc accactctca cagtctcctc a             351
```

| SEQ ID NO: 106 | moltype = DNA length = 360 |
|---|---|
| FEATURE | Location/Qualifiers |
| misc_feature | 1..360 |
| | note = VH for D1A1 |
| source | 1..360 |
| | mol_type = other DNA |
| | organism = synthetic construct |

SEQUENCE: 106

```
gaagtgatgc tggtggagtc tggggggaggc ttagtgaagc ctggagggtc cctgaaactc    60
tcctgtgcag cctctggatt cactttcagt aactatgcca tgtcttgggt tcgccagact   120
ccggagaaga ggctggagtg ggtcgcaacc attagtggtg gtggtggtaa catctactat   180
ccagacagtg tgaagggtcg attcaccatc tccagagaca atgccaggaa caccctgtac   240
ctgcaaatga gcagtctgag gtctgaggac acggccttgt attattgtgc aagcccgtat   300
gctaactacg tatggtacct cgatgtctgg ggcgcaggga ccacggtcac cgtctcctca   360
```

| SEQ ID NO: 107 | moltype = DNA length = 360 |
|---|---|
| FEATURE | Location/Qualifiers |
| misc_feature | 1..360 |
| | note = VH for D1F1 |
| source | 1..360 |
| | mol_type = other DNA |
| | organism = synthetic construct |

SEQUENCE: 107

```
gaagtgatgc tggtggagtc tggggggaggc ttagtgaagc ctggagggtc cctgaaactc    60
tcctgtgcag cctctggatt cactttcagt agcaatacca tgtcttgggt tcgccagact   120
ccggagaaga ggctggagtg ggtcgcagcc attagtggtg gtggtgttaa cacctactat   180
ccagacagtg tgaagggtcg attcaccatc tccagagaca atgccaggaa caccctgtac   240
ctgcaaatga gcagtctgag gtctgaggac acggccctgt attattgtgc aagacatggt   300
aactacaatt actatggtat ggactactgg ggtcaaggaa cctcagtcac cgtctcctca   360
```

| SEQ ID NO: 108 | moltype = DNA length = 360 |
|---|---|
| FEATURE | Location/Qualifiers |
| misc_feature | 1..360 |
| | note = VH for C1E2 |
| source | 1..360 |
| | mol_type = other DNA |
| | organism = synthetic construct |

SEQUENCE: 108

```
caggtccagt tgcagcagtc tggagctgag ctggtaaggc ctgggacttc agtgaagata    60
tcctgcaagg cttctggcta caccttcact aactactggc taggttgggt aaaacagagg   120
cctggacatg gacttgagtg gattggagat atttacccta gaggtggtta tactaactac   180
aatgagaact tcaagggcaa ggccacactg actgcagaca catcctccag cactgcctac   240
atgcagctca gtagcctgac atctgaggac tctgctgtct ttttctgtgc aagaggctac   300
ggtactaatt actggtactt cgatgtctgg ggcgcaggga ccacggtcac cgtctcctca   360
```

| SEQ ID NO: 109 | moltype = DNA length = 372 |
|---|---|
| FEATURE | Location/Qualifiers |
| misc_feature | 1..372 |
| | note = VH for C1A1 |
| source | 1..372 |
| | mol_type = other DNA |
| | organism = synthetic construct |

SEQUENCE: 109

```
caagttactc taaaagagtc tggccctggg atattgaagc cctcacagac cctcagtctg    60
acttgttctt tctctgggtt ttcactgagc acttctggta tgggtgtagg ctggattcgt   120
cagccttcag ggaagggtct ggagtggctg gcacacattt ggtgggatga tgataagttc   180
tataacccat ccctgaagag ccagctcaca atctccaagg atacctccag aaaccaggtt   240
ttcctcaaga tcaccagtgt ggacactgca gatactgcca cttactactg tgctcgaacc   300
ggggggttta ttactacggg ctactggtac ttcgatgtct ggggcgcagg gaccacggtc   360
accgtctcct ca                                                        372
```

| SEQ ID NO: 110 | moltype = DNA length = 354 |
|---|---|
| FEATURE | Location/Qualifiers |
| misc_feature | 1..354 |
| | note = VH for C1F4 |

```
source                     1..354
                           mol_type = other DNA
                           organism = synthetic construct
SEQUENCE: 110
caggtccagc tgcaacagtc tgggctgag ctggtgaggc ctggggtctc agtgaagatt    60
tcctgcaagg gttctggcta caaattcact gattatgcta tgcactgggt gaggcagagt   120
catgcaaaga gtctagagtg gattggaatt attagtactt actctggtga cgttagtttc   180
aaccagaact tcaagggcaa ggccacaatg actgtagaca atcctccag cacagccat    240
atggaacttg ccagactgac atctgaggat tctgccatct attactgttc aagactgggg   300
attacggcgg ggtttgctta ctggggccaa gggactctgg tcactgtctc tgca         354

SEQ ID NO: 111             moltype = DNA   length = 360
FEATURE                    Location/Qualifiers
misc_feature               1..360
                           note = VH for D2C2
source                     1..360
                           mol_type = other DNA
                           organism = synthetic construct
SEQUENCE: 111
gaagtgatgc tggtggagtc tgggggaggc ttagtgaagc ctggagggtc cctgaaactc    60
tcctgtgcag cctctggatt cactttcagt agcaatacca tgtcttgggt tcgccagact   120
ccggagaaga ggctggagtg ggtcgcagcc attagtggtg gtggtgttga cacctactat   180
ccagacagtg tgaaggggcg attcaccatc tccagagaca atgccaggaa cacccctgtac  240
ctgcaaatga gcagtctgag gtctgaggac acggccctgt attactgtgc aagacatggt   300
aactacaatt actatggtat ggactactgg ggtcaaggaa cctcagtcac cgtctcctca   360

SEQ ID NO: 112             moltype = DNA   length = 372
FEATURE                    Location/Qualifiers
misc_feature               1..372
                           note = VH for 2G2
source                     1..372
                           mol_type = other DNA
                           organism = synthetic construct
SEQUENCE: 112
gaggtgcaac tggtggagtc tgggggagac ttagtgaagc ctggagggtc cctgaaactc    60
tcctgtacag cctctggatt cactttcagt tactatggca tgtcttgggt tcgccagact   120
ccagacaaga ggctggaatg gtcgcaacc attagtagtg gtagtagttt cacctactct   180
ccagacagtg tgaaggggcg attcaccatc tccagagaca atgccaagaa cacccctgtac  240
ctacaaatga cagtctgaa gtctgaggac acagccattt attactgtac aagacgagag   300
gggatctatg atgcttcctg ggattattct atggactact ggggtcaagg aacctcagtc   360
accgtctcct ca                                                       372

SEQ ID NO: 113             moltype = DNA   length = 363
FEATURE                    Location/Qualifiers
misc_feature               1..363
                           note = VH for C1C5
source                     1..363
                           mol_type = other DNA
                           organism = synthetic construct
SEQUENCE: 113
cagatccagt tggtgcagtc aggacctgag ctgaagaagc ctggagagac agtcaagatc    60
tcctgcaagg cttctgggta taccttcaca aactatggaa taaactgggt gaagcaggct   120
ccaggaaagg gtttaaagtg gatgggctgg ataaacacct atagtggaga gccaacatat   180
tctgatgact caagggacg ctttgccttc tctttggaaa cctctgccag cactgcctat    240
ttgcagatca caacctcaa aaatgaggac acgtctacat atttctgtgt aagacagggg   300
gactttgatt acgaggatgc tatggactac tggggtcaag gaacctcagt caccgtctcc   360
tca                                                                 363

SEQ ID NO: 114             moltype = DNA   length = 333
FEATURE                    Location/Qualifiers
misc_feature               1..333
                           note = VL for C1E1
source                     1..333
                           mol_type = other DNA
                           organism = synthetic construct
SEQUENCE: 114
gacattgtgc tgacccaatc tccagcttct ttggctgtgt ctctagggca gagggccacc    60
atctcctgca gagccagcaa aagtgttgat gattctggca ttagttttat gcactggttc   120
caacgaaac caggacagcc acccaaactc ctcatcatg ctgcatccaa ccaaggatcc     180
ggggtccctg ccaggtttcg tggcagtggg tctgggacag acttcagcct caacatccat   240
cctatggagg aggatgatac tgcaatgtat ttctgtcacc aaactaagga ggttccgtgg   300
acgttcggtg gaggcaccaa gctggaaatc aaa                                333

SEQ ID NO: 115             moltype = DNA   length = 333
FEATURE                    Location/Qualifiers
misc_feature               1..333
                           note = VL for huC1E1-V7 and huC1E1-V10
source                     1..333
                           mol_type = other DNA
```

```
                        organism = synthetic construct
SEQUENCE: 115
gaaattgtgt tgacacagtc tccagccacc ctgtctttgt ctccagggga aagagccacc    60
ctctcctgca gggccagtaa gtctgttgac gacagtggta tcagcttcat gcactggtat   120
caacagaaac ctggccaggc tcccaggctc ctcatcatg ctgcatccaa ccagggctct    180
ggcatcccag ccaggttcag tggcagtggg tctgggacag acttcactct caccatcagc   240
agcctagagc ctgaagattt tgcagtttat tactgtcatc agactaagga ggtgccttgg   300
acgttcggcc aagggaccaa ggtggagatc aaa                                333

SEQ ID NO: 116         moltype = DNA  length = 321
FEATURE                Location/Qualifiers
misc_feature           1..321
                       note = VL for D1F2
source                 1..321
                       mol_type = other DNA
                       organism = synthetic construct
SEQUENCE: 116
gatatccaga tgacacagac tacatcctcc ctgtctgcct ctctgggaga cagagtcacc    60
atcagttgca gggccagtca ggacattagc aattttttaa actggtatca gcagaaacca   120
gatggaactg ttaaactcct gatctactac acatcaagat tacagtcagg agtcccatca   180
aggttcagtg gcactgggtc tgggacagat tattctctca ccattagcaa cctgaacaa    240
gaagatcttg ccacttactt ttgccaacag ggtagttcgc ttccgtggac gttcggtgga   300
ggcaccaagc tggaaatcaa a                                             321

SEQ ID NO: 117         moltype = DNA  length = 321
FEATURE                Location/Qualifiers
misc_feature           1..321
                       note = VL for C1F5
source                 1..321
                       mol_type = other DNA
                       organism = synthetic construct
SEQUENCE: 117
gatattgtgc taactcagtc tccagccacc ctgtctgtga ctccaggaga tagcgtcagt    60
cttcctgca gggccagcca aagtattagc aacaactac tggtatca caaaaatca        120
catgagtctc caaggcttct catcaagtat ggttcccagt ccatgtctgg gatcccctcc   180
aggttcagtg gcagtggatc agggacagat ttcactctcg ttatcaacag tgtggagact   240
gaagattttg gaatgtattt ctgtcaacag agtaacagct ggcctctcac gttcggtgct   300
gggaccaagc tggagctgaa a                                             321

SEQ ID NO: 118         moltype = DNA  length = 321
FEATURE                Location/Qualifiers
misc_feature           1..321
                       note = VL for D1A1
source                 1..321
                       mol_type = other DNA
                       organism = synthetic construct
SEQUENCE: 118
gatatccaga tgacacagac tacatcctcc ctgtctgcct ctctgggaga cagagtcacc    60
atcagttgca gggcaagtca ggacattagc aattatttaa actggtatca gcagaaacca   120
gatggaactg ttaaactcct gatctactac acatcaagat tacactcagg agtcccatca   180
aggttcagtg gcagtgggtc tggaacagat ttttctctca ccattagcaa cctgaagaa    240
gaagatattg ccacttactt ttgccaacag agtaatgcgc ttccgtggac gttcggtgga   300
ggcaccaaac tggaaatcaa a                                             321

SEQ ID NO: 119         moltype = DNA  length = 333
FEATURE                Location/Qualifiers
misc_feature           1..333
                       note = VL for D1F1
source                 1..333
                       mol_type = other DNA
                       organism = synthetic construct
SEQUENCE: 119
gacattgtgt tgacccaatc tccagcttct ttggttgtgt ctctagggca gagggccacc    60
atctcctgca gagccagcga aagtgttgat aattctgca ttagttttat gaactggttc    120
caacagaaac caggacagcc acccaaactc ctcatctata ctgcatccaa ccaaggatcc   180
ggggtccctg ccaggtttag tggcagtggg tctgggacag acttcagcct caacatccat   240
cctatggagg aggatgattc tgcaatgtat ttctgtcagc aaagttatga ggttccttgg   300
acgttcggtg gaggcaccaa gctggaaatc aaa                                333

SEQ ID NO: 120         moltype = DNA  length = 321
FEATURE                Location/Qualifiers
misc_feature           1..321
                       note = VL for C1E2
source                 1..321
                       mol_type = other DNA
                       organism = synthetic construct
SEQUENCE: 120
agtattgtga tgacccagac tcccaaattc ctgcttgtat cagcaggaga cagggttacc    60
ataacctgca aggccagtca gagtgtgagt aatgatgtag cttggtacca acagaagcca   120
```

```
gggcagtctc ctaaactgct gatatactat gcatttcatc gctacactgg agtccctgat    180
cgcttcactg gcagtggata tgggacggat ttcactttca ccatcagcac tgtgcaggct    240
gaagacctgg cagtttattt ctgtcagcag gattatagct ctccgtacac gttcggaggg    300
gggaccaagc tggaaataaa a                                              321

SEQ ID NO: 121            moltype = DNA  length = 321
FEATURE                   Location/Qualifiers
misc_feature              1..321
                          note = VL for C1A1
source                    1..321
                          mol_type = other DNA
                          organism = synthetic construct
SEQUENCE: 121
gatatccaga tgacacagac tacatcctcc ctgtctgcct ctctgggaga cagagtcacc    60
atcagttgca gggcaagtca ggacattagc aattatttaa tctggtatca gcagaaaaca    120
gatggaactc ttaaactcct gatctactac acatcaagat tacactcagg agtcccatca    180
aggttcagtg gcagtgggtc tggaacagat tattctctca ccattagcaa cctggagcaa    240
gaagatattg ccacttactt ttgccagcag cataaaacgc ttccgtggac gttcggtgga    300
ggcaccaagc tggaaatcaa a                                              321

SEQ ID NO: 122            moltype = DNA  length = 321
FEATURE                   Location/Qualifiers
misc_feature              1..321
                          note = VL for C1F4
source                    1..321
                          mol_type = other DNA
                          organism = synthetic construct
SEQUENCE: 122
gacattgtga tgacccagtc tcaaaaattc atgtccacat cagtaggaga cagggtcacc    60
atcacctgca aggccagtca gaatgttcgt actgctgtag cctggtatca acagaaacca    120
gggcagtctc ctaaagcact gatttacttg gcatccaacc ggcacactgg agtccctgat    180
cgcttcacag gcagtggatc tgggacagat ttcactctca ccattagcaa tgtgcaatct    240
aaagacctgg cagattattt ctgtctgcaa cattggaatt atccgtacac gttcggaggg    300
gggaccaagc tggaaataaa a                                              321

SEQ ID NO: 123            moltype = DNA  length = 333
FEATURE                   Location/Qualifiers
misc_feature              1..333
                          note = VL for D2C2
source                    1..333
                          mol_type = other DNA
                          organism = synthetic construct
SEQUENCE: 123
gacattgtgc tgacccaatc tccagcttct ttggctgtgt ctctagggca gagggccacc    60
atctcctgca gagccagcga aagtgttgat aattctggca ttagttttat gaactggttc    120
caacagaaac caggacagtc acccaaactc ctcatctata ttgcatccaa ccacggatcc    180
ggggtccctg ccaggtttag tggcagtggg tctgggacag acttcagcct caacatccat    240
cctatggagg aggatgattc tgcaatgtat ttctgtcagc aaagttatga ggttccttgg    300
acgttcggtg gaggcaccaa gctggaaatc aaa                                 333

SEQ ID NO: 124            moltype = DNA  length = 336
FEATURE                   Location/Qualifiers
misc_feature              1..336
                          note = VL for 2G2
source                    1..336
                          mol_type = other DNA
                          organism = synthetic construct
SEQUENCE: 124
gatgttttga tgacccaaac tccactctcc ctgcctgtca gtcttggaga tcaagcctcc    60
atctcttgca gatctagtca gagcattata cgtagtaatg gaaacaccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgacga tctgggactt tattactgct ttcaaggttc acatgttccg    300
tggacgttcg gtggaggcac caagctggaa atcaaa                              336

SEQ ID NO: 125            moltype = DNA  length = 330
FEATURE                   Location/Qualifiers
misc_feature              1..330
                          note = VL for C1C5
source                    1..330
                          mol_type = other DNA
                          organism = synthetic construct
SEQUENCE: 125
gatgttttga tgacccaaag tccactctcc ctgcctgtca gtcttggaga tcaagcctcc    60
atctcttgca gatctagtca gagtattgta catagtaatg gacacatcta tttagaatgg    120
tacctgcaga aaccaggcca gtctccaaag ctcctgatct acaaagtttc caagcgattt    180
tctggggtcc cagacaggtt cagtggcagt ggatcaggga cagatttcac actcaagatc    240
agcagagtgg aggctgagga tctggagtt tattactgct ttcaaggttc acatgggacg    300
ttcggtggag gcaccaagct ggaaatcaaa                                     330
```

```
SEQ ID NO: 126          moltype = DNA   length = 990
FEATURE                 Location/Qualifiers
misc_feature            1..990
                        note = human IgG1 heavy chain constant region
source                  1..990
                        mol_type = other DNA
                        organism = synthetic construct
SEQUENCE: 126
gctagcacca agggcccatc ggtcttcccc ctggcaccct cctccaagag cacctctggg   60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagcgc  300
aaatcttgtg acaaaactca cacatgccca ccgtgcccag cacctgaact cctggggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacaac  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                   990

SEQ ID NO: 127          moltype = DNA   length = 321
FEATURE                 Location/Qualifiers
misc_feature            1..321
                        note = human kappa light chain constant region
source                  1..321
                        mol_type = other DNA
                        organism = synthetic construct
SEQUENCE: 127
cgtacggtgg cggcgccatc tgtcttcatc ttcccgccat ctgatgagca gttgaaatct   60
ggaactgcct ctgttgtgtg cctgctgaat aacttctatc ccagagaggc caaagtacag  120
tggaaggtgg ataacgccct ccaatcgggt aactcccagg agagtgtcac agagcaggac  180
agcaaggaca gcacctacag cctcagcagc accctgacgc tgagcaaagc agactacgag  240
aaacacaaag tctacgcctg cgaagtcacc catcagggcc tgagctcgcc cgtcacaaag  300
agcttcaaca ggggagagtg t                                            321

SEQ ID NO: 128          moltype = DNA   length = 294
FEATURE                 Location/Qualifiers
misc_feature            1..294
                        note = human IgG1 heavy chain CH1 region
source                  1..294
                        mol_type = other DNA
                        organism = synthetic construct
SEQUENCE: 128
gcctccacca agggcccatc ggtcttcccc ctggcaccct cctccaagag cacctctggg   60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agtt        294

SEQ ID NO: 129          moltype = AA    length = 324
FEATURE                 Location/Qualifiers
REGION                  1..324
                        note = Heavy chain constant region for mouse antibodies
source                  1..324
                        mol_type = protein
                        organism = synthetic construct
SEQUENCE: 129
AKTTPPSVYP LAPGSAAQTN SMVTLGCLVK GYFPEPVTVT WNSGSLSSGV HTFPAVLQSD   60
LYTLSSSVTV PSSTWPSETV TCNVAHPASS TKVDKKIVPR DCGCKPCICT VPEVSSVFIF  120
PPKPKDVLTI TLTPKVTCVV VDISKDDPEV QFSWFVDDVE VHTAQTQPRE EQFNSTFRSV  180
SELPIMHQDW LNGKEFKCRV NSAAFPAPIE KTISKTKGRP KAPQVYTIPP PKEQMAKDKV  240
SLTCMITDFF PEDITVEWQW NGQPAENYKN TQPIMDTDGS YFVYSKLNVQ KSNWEAGNTF  300
TCSVLHEGLH NHHTEKSLSH SPGK                                         324

SEQ ID NO: 130          moltype = AA    length = 107
FEATURE                 Location/Qualifiers
REGION                  1..107
                        note = Light chain constant region for mouse antibodies
source                  1..107
                        mol_type = protein
                        organism = synthetic construct
SEQUENCE: 130
```

```
RADAAPTVSI FPPSSEQLTS GGASVVCFLN NFYPKDINVK WKIDGSERQN GVLNSWTDQD     60
SKDSTYSMSS TLTLTKDEYE RHNSYTCEAT HKTSTSPIVK SFNRGEC                 107
```

ANTIBODIES BINDING PD-1 AND USES THEREOF

CROSS-REFERENCE TO RELATED APPLICATION

This application is a continuation of U.S. application Ser. No. 17/047,649, filed Oct. 14, 2020, which is a U.S. national stage of International Application No. PCT/US2019/027115, filed Apr. 12, 2019, which claims the benefit under 35 U.S.C. § 119(e) from U.S. Application No. 62/657,927, filed Apr. 15, 2018. The contents of the foregoing applications are hereby incorporated by reference in their entirety.

SEQUENCE LISTING

The contents of the electronic sequence listing (Sequencelisting_44GC-320421-US2.xml; Size: 176,592 bytes; and Date of Creation: Apr. 10, 2024) is herein incorporated by reference in its entirety.

FIELD OF THE INVENTION

The present invention relates generally to an isolated monoclonal antibody, particularly a mouse, chimeric or humanized monoclonal antibody that specifically binds to human PD-1 with high affinity and functionality. A nucleic acid molecule encoding the antibody, an expression vector, a host cell and a method for expressing the antibody are also provided. The present invention further provides an immunoconjugate, a bispecific molecule, an oncolytic virus, and a pharmaceutical composition comprising the antibody, as well as a diagnostic and treatment method using an anti-PD-1 antibody of the invention.

BACKGROUND OF THE INVENTION

Programmed cell death protein 1, also known as PD-1 or CD279, is a member of the CD28 family of T cell regulators, and expressed on activated B cells, T cells, and myeloid cells (Agata et al., (1996) *Int Immunol* 8:765-72; Okazaki et al., (2002) *Curr. Opin. Immunol.* 14: 391779-82; Bennett et al., (2003) *J Immunol* 170:711-8). It contains a membrane proximal immunoreceptor tyrosine inhibitory motif (ITIM) and a membrane distal tyrosine-based switch motif (ITSM) (Thomas, M. L. (1995) *J Exp Med* 181:1953-6; Vivier, E and Daeron, M (1997) *Immunol Today* 18:286-91). Two ligands for PD-1 have been identified, PD-L1 and PD-L2, both are B7 homologs that bind to PD-1, but do not bind to other CD28 family members.

Several lines of evidence have suggested that PD-1 and its ligands negatively regulate immune responses. For example, PD-1 was found abundant in a variety of human cancers (Dong et al., (2002) *Nat. Med.* 8:787-9). Further, the interaction between PD-1 and PD-L1 was reported to cause a decrease in tumor infiltrating lymphocytes and T-cell receptor mediated proliferation, and immune evasion of cancerous cells (Dong et al., (2003) *J. Mol. Med.* 81:281-7; Blank et al., (2005) *Cancer Immunol. Immunother.* 54:307-314; Konishi et al., (2004) *Clin. Cancer Res.* 10:5094-100). Studies also showed that immune suppression can be reversed by inhibiting the local interaction of PD-1 with PD-L1, and the effect was additive when the interaction of PD-1 with PD-L2 was blocked as well (Iwai et al., (2002) *Proc. Nat'l. Acad. Sci.* USA 99:12293-7; Brown et al., (2003) *J. Immunol.* 170:1257-66).

PD-1 deficient animals may develop various autoimmune phenotypes, including autoimmune cardiomyopathy and a lupus-like syndrome with arthritis and nephritis (Nishimura et al., (1999) *Immunity* 11:141-51; Nishimura et al., (2001) *Science* 291:319-22). Additionally, PD-1 has been found to play a role in autoimmune encephalomyelitis, systemic lupus erythematosus, graft-versus-host disease (GVHD), type I diabetes, and rheumatoid arthritis (Salama et al., (2003) *J Exp Med* 198:71-78; Prokunina and Alarcon-Riquelme (2004) *Hum Mol Genet* 13:R143; Nielsen et al., (2004) *Lupus* 13:510). In a murine B cell tumor line, the ITSM of PD-1 was shown to be essential to block BCR-mediated $Ca^{2+}$-flux and tyrosine phosphorylation of downstream effector molecules (Okazaki et al., (2001) *PNAS* 98:13866-71).

A number of cancer immunotherapy agents that target PD-1 have been developed for disease treatment. One such anti-PD-1 antibody is Nivolumab (sold under the tradename of OPDIVO® by Bristol Myers Squibb), which produced complete or partial responses in non-small-cell lung cancer, melanoma, and renal-cell cancer, in a clinical trial with a total of 296 patients (Topalian S L et al., (2012) *The New England Journal of Medicine.* 366 (26): 2443-54). It was approved in Japan in 2014 and by US FDA in 2014 to treat metastatic melanoma. Another anti-PD-1 antibody, Pembrolizumab (KEYTRUDA™, MK-3475, Merck) targeting PD-1, was also approved by US FDA in 2014 to treat metastatic melanoma. It is being used in clinical trials in US for lung cancer, lymphoma, and mesothelioma.

Despite the anti-PD-1 antibodies that are already developed and approved, there is a need for additional monoclonal antibodies with enhanced binding affinity to PD-1 and other desirable pharmaceutical characteristics.

SUMMARY OF THE INVENTION

The present invention provides an isolated monoclonal antibody, for example, a mouse, human, chimeric or humanized monoclonal antibody, that binds to PD-1 (e.g., the human PD-1, and monkey PD-1) and has increased affinity to PD-1 and comparable, if not better, anti-tumor effect compared to existing anti-PD-1 antibodies such as Nivolumab.

The antibody of the invention can be used for a variety of applications, including detection of the PD-1 protein, and treatment and prevention of PD-1 associated diseases, such as cancers, autoimmune cardiomyopathy, autoimmune encephalomyelitis, systemic lupus erythematosus, graft-versus-host disease (GVHD), type I diabetes, and rheumatoid arthritis.

Accordingly, in one aspect, the invention pertains to an isolated monoclonal antibody (e.g., a mouse, chimeric or humanized antibody), or an antigen-binding portion thereof, that binds PD-1, having a heavy chain variable region that comprises a CDR1 region, a CDR2 region and a CDR3 region, wherein the CDR1 region, the CDR2 region and the CDR3 region comprise amino acid sequences having at least 80%, 85%, 90%, 95%, 98%, 99% or 100% identity to (1) SEQ ID NOs: 1, 2 and 3, respectively; (2) SEQ ID NOs: 4, 5 and 6, respectively; (3) SEQ ID NOs: 7, 8 and 9, respectively; (4) SEQ ID NOs: 10, 11 and 12, respectively; (5) SEQ ID NOs: 13, 14 and 15, respectively; (6) SEQ ID NOs: 16, 17 and 18, respectively; (7) SEQ ID NOs: 19, 20 and 21, respectively; (8) SEQ ID NOs: 22, 23 and 24, respectively; (9) SEQ ID NOs: 25, 26 and 27, respectively; (10) SEQ ID NOs: 28, 29 and 30, respectively; or (11) SEQ ID NOs: 31, 32 and 33, respectively, wherein, the antibody, or antigen-binding fragment thereof, binds to PD-1.

In one aspect, an isolated monoclonal antibody, or an antigen-binding portion thereof, of the present invention comprises a heavy chain variable region comprising an amino acid sequence having at least 80%, 85%, 90%, 95%, 98%, 99% or 100% identity to SEQ ID NOs: 67, 68, 69, 70, 71, 72, 73, 74, 75, 76, 77, 78 or 79, wherein the antibody or antigen-binding fragment thereof binds to PD-1. SEQ ID NOs: 67 and 69-79 may be encoded by nucleic acid sequences of SEQ ID NOs: 102-113, respectively.

In one aspect, an isolated monoclonal antibody, or an antigen-binding portion thereof, of the present invention comprises a light chain variable region that comprises a CDR1 region, a CDR2 region and a CDR3 region, wherein the CDR1 region, the CDR2 region, and the CDR3 region comprise amino acid sequences having at least 80%, 85%, 90%, 95%, 98%, 99% or 100% identity to (1) SEQ ID NOs: 34, 35 and 36, respectively; (2) SEQ ID NOs: 37, 38 and 39, respectively; (3) SEQ ID NOs: 40, 41 and 42, respectively; (4) SEQ ID NOs: 43, 44 and 45, respectively; (5) SEQ ID NOs: 46, 47 and 48, respectively; (6) SEQ ID NOs: 49, 50 and 51, respectively; (7) SEQ ID NOs: 52, 53 and 54, respectively; (8) SEQ ID NOs: 55, 56 and 57, respectively; (9) SEQ ID NOs: 58, 59 and 60, respectively; (10) SEQ ID NOs: 61, 62 and 63, respectively; or (11) SEQ ID NOs: 64, 65 and 66, respectively, wherein, the antibody, or antigen-binding fragment thereof, binds to PD-1.

In one aspect, an isolated monoclonal antibody, or an antigen-binding portion thereof, of the present invention comprises a light chain variable region comprising an amino acid sequence having at least 80%, 85%, 90%, 95%, 98%, 99% or 100% identity to SEQ ID NOs: 80, 81, 82, 83, 84, 85, 86, 87, 88, 89, 90, 91, 92, 93, 94, 95 or 96, wherein the antibody or antigen-binding fragment thereof binds to PD-1. SEQ ID NOs: 80 and 86-96 may be encoded by nucleic acid sequences of SEQ ID NOs: 114-125, and, respectively.

In one aspect, an isolated monoclonal antibody, or an antigen-binding portion thereof, of the present invention comprises a heavy chain variable region and a light chain variable region each comprising a CDR1 region, a CDR2 region and a CDR3 region, wherein the heavy chain variable region CDR1, CDR2 and CDR3, and the light chain variable region CDR1, CDR2 and CDR3 comprise amino acid sequences having at least 80%, 85%, 90%, 95%, 98%, 99% or 100% identity to (1) SEQ ID NOs: 1, 2, 3, 34, 35 and 36, respectively; (2) SEQ ID NOs: 4, 5, 6, 37, 38 and 39, respectively; (3) SEQ ID NOs: 7, 8, 9, 40, 41 and 42, respectively; (4) SEQ ID NOs: 10, 11, 12, 43, 44 and 45, respectively; (5) SEQ ID NOs: 13, 14, 15, 46, 47 and 48, respectively; (6) SEQ ID NOs: 16, 17, 18, 49, 50 and 51, respectively; (7) SEQ ID NOs: 19, 20, 21, 52, 53 and 54, respectively; (8) SEQ ID NOs: 22, 23, 24, 55, 56 and 57, respectively; (9) SEQ ID NOs: 25, 26, 27, 58, 59 and 60, respectively; (10) SEQ ID NOs: 28, 29, 30, 61, 62 and 63, respectively; or (11) SEQ ID NOs: 31, 32, 32, 64, 65 and 66, respectively, wherein the antibody or antigen-binding fragment thereof binds to PD-1.

In one embodiment, an isolated monoclonal antibody, or the antigen-binding portion thereof, of the present invention comprises a heavy chain variable region and a light chain variable region, the heavy chain variable region and the light chain variable region comprising amino acid sequences having at least 80%, 85%, 90%, 95%, 98%, 99% or 100% identity to (1) SEQ ID NOs: 67 and 80, respectively; (2) SEQ ID NOs: 68 and 81, respectively; (3) SEQ ID NOs: 69 and 81, respectively; (4) SEQ ID NOs: 68 and 82, respectively; (5) SEQ ID NOs: 68 and 83, respectively; (6) SEQ ID NOs: 68 and 84, respectively; (7) SEQ ID NOs: 68 and 85, respectively; (8) SEQ ID NOs: 68 and 86, respectively; (9) SEQ ID NOs: 69 and 86, respectively; (10) SEQ ID NOs: 70 and 87 respectively; (11) SEQ ID NOs: 71 and 88, respectively; (12) SEQ ID NOs: 72 and 89, respectively; (13) SEQ ID NOs: 73 and 90, respectively; (14) SEQ ID NOs: 74 and 91, respectively; (15) SEQ ID NOs: 75 and 92, respectively; (16) SEQ ID NOs: 76 and 93, respectively; (17) SEQ ID NOs: 77 and 94, respectively; (18) SEQ ID NOs: 78 and 95, respectively; or (19) SEQ ID NOs: 79 and 96, respectively, wherein the antibody or antigen-binding fragment thereof binds to PD-1.

In one embodiment, an isolated monoclonal antibody, or the antigen-binding portion thereof, of the present invention comprises a heavy chain and a light chain, the heavy chain comprising a heavy chain variable region and a heavy chain constant region, the light chain comprising a light chain variable region and a light chain constant region, wherein, the heavy chain constant region comprises amino acid sequences having at least 80%, 85%, 90%, 95%, 98%, 99% or 100% identity to SEQ ID No: 97, 99 or 129, and the light chain constant region comprises amino acid sequences having at least 80%, 85%, 90%, 95%, 98%, 99% or 100% identity to SEQ ID No: 98 or 130, and the heavy chain variable region and the light chain variable region comprise amino acid sequences described above, wherein the antibody or antigen-binding fragment thereof binds to PD-1. These amino acid sequences of SEQ ID NOs: 97 and 99 may be encoded by nucleic acid sequences of SEQ ID NOs: 126 and 128, respectively. SEQ ID NO:98 may be encoded by SEQ ID NOs: 127.

The antibody of the present invention in some embodiments comprises or consists of two heavy chains and two light chains, wherein each heavy chain comprises the heavy chain constant region, heavy chain variable region or CDR sequences mentioned above, and each light chain comprises the light chain constant region, light chain variable region or CDR sequences mentioned above, wherein the antibody binds to PD-1. The antibody of the invention can be a full-length antibody, for example, of an IgG1, IgG2 or IgG4 isotype. The antibody of the present invention in other embodiments may be a single chain antibody, or antibody fragments, such as Fab or Fab'2 fragments.

The antibody, or antigen-binding portion thereof, of the present invention has higher binding affinity to human PD-1 than prior art anti-PD-1 antibodies such as Nivolumab, binding to human PD-1 with a $K_D$ of $6.36 \times 10^{-9}$M or less and inhibiting the binding of PD-L1 to PD-1. The antibody or antigen-binding portion thereof of the invention also provides comparable, if not better, anti-tumor effect compared to existing anti-PD-1 antibodies such as Nivolumab.

The invention also provides an immunoconjugate comprising an antibody of the invention, or antigen-binding portion thereof, linked to a therapeutic agent, such as a cytotoxin. The invention also provides a bispecific molecule comprising an antibody, or antigen-binding portion thereof, of the invention, linked to a second functional moiety (e.g., a second antibody) having a different binding specificity than said antibody, or antigen-binding portion thereof. In another aspect, the antibody or an antigen binding portions thereof of the present invention can be made into part of a chimeric antigen receptor (CAR). The antibody or an antigen binding portions thereof of the present invention can also be encoded by or used in conjuction with an oncolytic virus.

Compositions comprising an antibody, or antigen-binding portion thereof, or immunoconjugate, bispecific molecule, oncolytic virus, or CAR of the invention, and a pharmaceutically acceptable carrier, are also provided.

Nucleic acid molecules encoding the antibodies, or antigen-binding portions thereof, of the invention are also encompassed by the invention, as well as expression vectors comprising such nucleic acids and host cells comprising such expression vectors. A method for preparing an anti-PD-1 antibody using the host cell comprising the expression vector is also provided, comprising steps of (i) expressing the antibody in the host cell and (ii) isolating the antibody from the host cell or its cell culture.

In yet another aspect, the invention provides a method of modulating an immune response in a subject comprising administering to the subject the antibody, or antigen-binding portion thereof, of the invention such that the immune response in the subject is modulated. Preferably, the antibody of the invention enhances, stimulates or increases the immune response in the subject. In some embodiments, the method comprises administering a composition, a bispecific molecule, an immunnoconjugate, a CAR-T cell, or an antibody-encoding or antibody-bearing oncolytic virus of the invention, or alternatively a nucleic acid molecule capable of expressing the same in the subject.

In a further aspect, the invention provides a method of inhibiting tumor growth in a subject, comprising administering to a subject a therapeutically effective amount of the antibody, or antigen-binding portion thereof, of the present invention. The tumor may be a solid or non-solid tumor, including, but not limited to, lymphoma, leukemia, multiple myeloma, melanoma, colon adenocarcinoma, pancreas cancer, colon cancer, gastric intestine cancer, prostate cancer, bladder cancer, kidney cancer, ovary cancer, cervix cancer, breast cancer, lung cancer, renal-cell cancer and nasopharynx cancer. In some embodiments, the method comprises administering a composition, a bispecific molecule, an immunnoconjugate, a CAR-T cell, or an antibody-encoding or antibody-bearing oncolytic virus of the invention, or alternatively a nucleic acid molecule capable of expressing the same in the subject.

In another aspect, the invention provides a method of treating an infectious disease in a subject, comprising administering to a subject a therapeutically effective amount of the antibody, or antigen-binding portion thereof, of the present invention. In some embodiments, the method comprises administering a composition, a bispecific molecule, an immunnoconjugate, a CAR-T cell, or an antibody-encoding or antibody-bearing oncolytic virus of the invention, or alternatively a nucleic acid molecule capable of expressing the same in the subject.

Still further, the invention provides a method of enhancing an immune response to an antigen in a subject, comprising administering to the subject: (i) the antigen; and (ii) the antibody, or antigen-binding portion thereof, such that an immune response to the antigen in the subject is enhanced. The antigen can be, for example, a tumor antigen, a viral antigen, a bacterial antigen or an antigen from a pathogen.

The antibodies of the invention can be used in combination with at least one additional agent such as an immunostimulatory antibody (e.g., an anti-PD-L1 antibody and/or an anti-CTLA-4 antibody), a cytokine (e.g., IL-2 and/or IL-21), or a costimulatory antibody (e.g., an anti-CD137 and/or anti-GITR antibody).

Other features and advantages of the instant disclosure will be apparent from the following detailed description and examples, which should not be construed as limiting. The contents of all references, Genbank entries, patents and published patent applications cited throughout this application are expressly incorporated herein by reference.

DETAILED DESCRIPTION OF THE INVENTION

Figure 1:
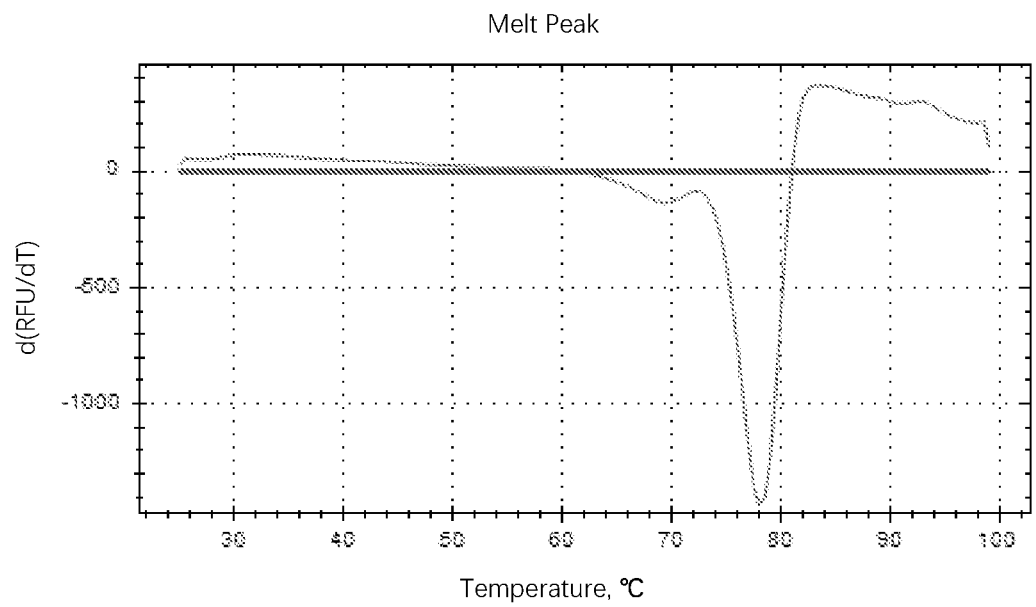
FIG. 1 shows humanized anti-PD-1 antibody huC1E1-V10's melt curve.

To ensure that the present disclosure may be more readily understood, certain terms are first defined. Additional definitions are set forth throughout the detailed description.

The term "PD-1" refers to programmed cell death protein 1. The term "PD-1" comprises variants, isoforms, homologs, orthologs and paralogs. For example, an antibody specific for a human PD-1 protein may, in certain cases, cross-react with a PD-1 protein from a species other than human, such as monkey. In other embodiments, an antibody specific for a human PD-1 protein may be completely specific for the human PD-1 protein and exhibit no cross-reactivity to other species or of other types; or may cross-react with PD-1 from certain other species but not all other species.

The term "human PD-1" refers to an PD-1 protein having an amino acid sequence from a human, such as the amino acid sequence of human PD-1 having Genbank Accession No. NP_005009.2. The terms "monkey or rhesus PD-1" and "mouse PD-1" refer to monkey and mouse PD-1 sequences, respectively, e.g. those with the amino acid sequences having Genbank Accession Nos. NP_001107830 and CAA48113, respectively.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

An "antigen-specific T cell response" refers to responses by a T cell that result from stimulation of the T cell with the antigen for which the T cell is specific. Non-limiting examples of responses by a T cell upon antigen-specific stimulation include proliferation and cytokine production (e.g., IL-2 production).

The term "antibody" as referred to herein includes whole antibodies and any antigen binding fragment (i.e., "antigen-binding portion") or single chains thereof. Whole antibodies are glycoproteins comprising two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a PD-1 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a PD-1 protein is substantially free of antibodies that specifically bind antigens other than PD-1 proteins). An isolated antibody that specifically binds a human PD-1 protein may, however, have cross-reactivity to other antigens, such as PD-1 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the invention can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimetic antibody is an antibody having genetic material from a certain species with genetic material from another species.

The term "humanized antibody", as used herein, refers to an antibody from non-human species whose protein sequences have been modified to increase similarity to antibody variants produced naturally in humans.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human PD-1" is intended to refer to an antibody that binds to human PD-1 protein (and possibly a PD-1 protein from one or more non-human species) but does not substantially bind to non-PD-1 proteins. Preferably, the antibody binds to human PD-1 protein with "high affinity", namely with a $K_D$ of $5.0 \times 10^{-8}$ M or less, more preferably $1.0 \times 10^{-8}$ M or less, and more preferably $7.0 \times 10^{-9}$ M or less.

The term "does not substantially bind" to a protein or cells, as used herein, means does not bind or does not bind with a high affinity to the protein or cells, i.e. binds to the protein or cells with a $K_D$ of $1.0 \times 10^{-6}$ M or more, more preferably $1.0 \times 10^{-5}$ M or more, more preferably $1.0 \times 10^{-4}$ M or more, more preferably $1.0 \times 10^{-3}$ M or more, even more preferably $1.0 \times 10^{-2}$ M or more.

The term "high affinity" for an IgG antibody refers to an antibody having a $K_D$ of $1.0 \times 10^{-6}$ M or less, more preferably $5.0 \times 10^{-8}$ M or less, even more preferably $1.0 \times 10^{-8}$ M or less, even more preferably $7.0 \times 10^{-9}$ M or less and even more preferably $1.0 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "$EC_{50}$", also known as half maximal effective concentration, refers to the concentration of an antibody which induces a response halfway between the baseline and maximum after a specified exposure time.

The term "$IC_{50}$", also known as half maximal inhibitory concentration, refers to the concentration of an antibody which inhibits a specific biological or biochemical function by 50% relative to the absence of the antibody.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody of the present invention sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

Various aspects of the invention are described in further detail in the following subsections.

Anti-PD-1 Antibodies Having Increased Binding Affinity to Human PD-1 and Better Anti-Tumor Effect The antibody, or the antigen-binding portion thereof, of the invention specifically binds to human PD-1 and have improved binding affinity as well as comparable, if not better, anti-tumor effect compared to previously described anti-PD-1 antibodies, particularly compared to Nivolumab.

The antibody, or the antigen-binding portion thereof, of the invention preferably binds to human PD-1 protein with a $K_D$ of $7.0 \times 10^{-9}$ M or less, more preferably with a $K_D$ of $5.0 \times 10^{-10}$ M or less. The antibodies of the invention also bind to Cynomolgus monkey PD-1 with a $K_D$ at about $1.0 \times 10^{-7}$ M to $1.0 \times 10^{-10}$ M.

Additional functional properties include the capacity to block PD-1/PD-L1 interaction. The antibodies of the present invention, in one embodiment, can inhibit binding of PD-1 to PD-L1 at a similar concentration as Nivolumab.

Other functional properties include the ability of the antibody to stimulate an immune response, such as an antigen-specific T cell response. This can be tested, for example, by assessing the ability of the antibody to stimulate interleukin-2 (IL-2) production in an antigen-specific T cell response. In certain embodiments, the antibody binds to human PD-1 and stimulates an antigen-specific T cell response. In other embodiments, the antibody binds to human PD-1 but does not stimulate an antigen-specific T cell response. Other means for evaluating the capacity of the antibody to stimulate an immune response include testing its ability to inhibit tumor growth, such as in an in vivo tumor graft model or the ability to stimulate an autoimmune response, such as the ability to promote the development of an autoimmune disease in an autoimmune model, e.g., the ability to promote the development of diabetes in the NOD mouse model.

Preferred antibodies of the invention are human monoclonal antibodies. Additionally or alternatively, the antibodies can be, for example, chimeric or humanized monoclonal antibodies.

Monoclonal Anti-PD-1 Antibody

The preferred antibody of the invention is the monoclonal antibody structurally and chemically characterized as described below and in the following Examples. The $V_H$ amino acid sequence of the anti-PD-1 antibody is set forth in SEQ ID NOs: 67, 68, 69, 70, 71, 72, 73, 74, 75, 76, 77, 78 or 79. The $V_L$ amino acid sequence of the anti-PD-1 antibody is shown in SEQ ID NOs: 80, 81, 82, 83, 84, 85, 86, 87, 88, 89, 90, 91, 92, 93, 94, 95 or 96. The amino acid sequence ID numbers of the heavy/light chain variable regions of the antibodies are summarized in Table 1 below, some clones sharing the same $V_H$ or $V_L$. The heavy chain constant region for all clones may be IgG1 heavy chain constant region having an amino acid sequence set forth in, e.g., SEQ ID NOs: 97, or 129, and the light chain constant region for all clones may be kappa constant region having an amino acid sequence set forth in, e.g., SEQ ID NOs: 98 or 130. The antibody Fab may contain heavy/light chain variable region, heavy chain CH1 region (such as the one set forth in SEQ ID NO: 99) and light chain constant region.

The heavy chain variable region CDRs and the light chain variable region CDRs in Table 1 have been defined by the IMGT numbering scheme and Kabat numbering system, respectively. However, as is well known in the art, CDR regions can also be determined by other systems such as Chothia, and CCG system/method, based on heavy chain/light chain variable region sequences.

TABLE 1

Amino acid sequence ID numbers of heavy/light chain variable regions

| | SEQ ID NO. | | | | | | | |
|---|---|---|---|---|---|---|---|---|
| Clone | VH-CDR1 | VH-CDR2 | VH-CDR3 | VH | VL-CDR1 | VL-CDR2 | VL-CDR3 | VL |
| C1E1 | 1 | 2 | 3 | 67 | 34 | 35 | 36 | 80 |
| huC1E1-V1 | 1 | 2 | 3 | 68 | 34 | 35 | 36 | 81 |
| huC1E1-V2 | 1 | 2 | 3 | 69 | 34 | 35 | 36 | 81 |
| huC1E1-V3 | 1 | 2 | 3 | 68 | 34 | 35 | 36 | 82 |
| huC1E1-V4 | 1 | 2 | 3 | 68 | 34 | 35 | 36 | 83 |
| huC1E1-V5 | 1 | 2 | 3 | 68 | 34 | 35 | 36 | 84 |
| huC1E1-V6 | 1 | 2 | 3 | 68 | 34 | 35 | 36 | 85 |
| huC1E1-V7 | 1 | 2 | 3 | 68 | 34 | 35 | 36 | 86 |
| huC1E1-V10 | 1 | 2 | 3 | 69 | 34 | 35 | 36 | 86 |
| D1F2 | 4 | 5 | 6 | 70 | 37 | 38 | 39 | 87 |
| C1F5 | 7 | 8 | 9 | 71 | 40 | 41 | 42 | 88 |
| D1A1 | 10 | 11 | 12 | 72 | 43 | 44 | 45 | 89 |
| D1F1 | 13 | 14 | 15 | 73 | 46 | 47 | 48 | 90 |
| C1E2 | 16 | 17 | 18 | 74 | 49 | 50 | 51 | 91 |
| C1A1 | 19 | 20 | 21 | 75 | 52 | 53 | 54 | 92 |
| C1F4 | 22 | 23 | 24 | 76 | 55 | 56 | 57 | 93 |
| D2C2 | 25 | 26 | 27 | 77 | 58 | 59 | 60 | 94 |
| 2G2 | 28 | 29 | 30 | 78 | 61 | 62 | 63 | 95 |
| C1C5 | 31 | 32 | 33 | 79 | 64 | 65 | 66 | 96 |

The $V_H$ and $V_L$ sequences (or CDR sequences) of other anti-PD-1 antibodies which bind to human PD-1 can be "mixed and matched" with the $V_H$ and $V_L$ sequences (or CDR sequences) of the anti-PD-1 antibody of the present invention. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the invention, or an antigen binding portion thereof, comprises:
  (a) a heavy chain variable region comprising an amino acid sequence listed above in Table 1; and
  (b) a light chain variable region comprising an amino acid sequence listed above in Table 1, or the $V_L$ of another anti-PD-1 antibody, wherein the antibody specifically binds human PD-1.

In another embodiment, an antibody of the invention, or an antigen binding portion thereof, comprises:
  (a) the CDR1, CDR2, and CDR3 regions of the heavy chain variable region listed above in Table 1; and
  (b) the CDR1, CDR2, and CDR3 regions of the light chain variable region listed above in Table 1 or the CDRs of another anti-PD-1 antibody, wherein the antibody specifically binds human PD-1.

In yet another embodiment, the antibody, or antigen binding portion thereof, includes the heavy chain variable CDR2 region of anti-PD-1 antibody combined with CDRs of other antibodies which bind human PD-1, e.g., CDR1 and/or CDR3 from the heavy chain variable region, and/or CDR1, CDR2, and/or CDR3 from the light chain variable region of a different anti-PD-1 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal 8: Scientific Review* 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the invention comprise the CDR2 of the heavy chain variable region of the anti-PD-1 antibody and at least the CDR3 of the heavy and/or light chain variable region of the anti-PD-1 antibody, or the CDR3 of the heavy and/or light chain variable region of another anti-PD-1 antibody, wherein the antibody is capable of specifically binding to human PD-1. These antibodies preferably (a) compete for binding with PD-1; (b) retain the functional characteristics; (c) bind to the same epitope; and/or (d) have a similar binding affinity as the anti-PD-1 antibody of the present invention. In yet another embodiment, the antibodies further may comprise the CDR2 of the light chain variable region of the anti-PD-1 antibody, or the CDR2 of the light chain variable region of another anti-PD-1 antibody, wherein the antibody is capable of specifically binding to human PD-1. In another embodiment, the antibodies of the invention may include the CDR1 of the heavy and/or light chain variable region of the anti-PD-1 antibody, or the CDR1 of the heavy and/or light chain variable region of another anti-PD-1 antibody, wherein the antibody is capable of specifically binding to human PD-1.

Conservative Modifications

In another embodiment, an antibody of the invention comprises a heavy and/or light chain variable region sequences of CDR1, CDR2 and CDR3 sequences which differ from those of the anti-PD-1 antibodies of the present invention by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:
  (a) the heavy chain variable region CDR1 sequence comprises a sequence listed in Table 1 above, and/or conservative modifications thereof; and/or
  (b) the heavy chain variable region CDR2 sequence comprises a sequence listed in Table 1 above, and/or conservative modifications thereof; and/or
  (c) the heavy chain variable region CDR3 sequence comprises a sequence listed in Table 1 above, and conservative modifications thereof; and/or
  (d) the light chain variable region CDR1, and/or CDR2, and/or CDR3 sequences comprise the sequence(s) listed in Table 1 above; and/or conservative modifications thereof; and
  (e) the antibody specifically binds human PD-1.

The antibody of the present invention possesses one or more of the following functional properties described above, such as high affinity binding to human PD-1, and the ability to induce ADCC or CDC against PD-1-expressing cells.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth above) using the functional assays described herein.

Engineered and Modified Antibodies

Antibodies of the invention can be prepared using an antibody having one or more of the $V_H/V_L$ sequences of the anti-PD-1 antibody of the present invention as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad.* See also U.S.A. 86:10029-10033; U.S. Pat. Nos. 5,225,539; 5,530,101; 5,585,089; 5,693,762 and 6,180,370).

Accordingly, another embodiment of the invention pertains to an isolated monoclonal antibody, or antigen binding portion thereof, comprising a heavy chain variable region comprising CDR1, CDR2, and CDR3 sequences comprising the sequences of the present invention, as described above, and/or a light chain variable region comprising CDR1, CDR2, and CDR3 sequences comprising the sequences of the present invention, as described above. While these antibodies contain the $V_H$ and $V_L$ CDR sequences of the monoclonal antibody of the present invention, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database, as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the invention are those that are structurally similar to the framework sequences used by antibodies of the invention. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the invention provides isolated anti-PD-1 monoclonal antibodies, or antigen binding portions thereof, comprising a heavy chain variable region comprising: (a) a $V_H$ CDR1 region comprising the sequence of the present invention, or an amino acid sequence having one, two, three, four or five amino acid substitutions, deletions or additions; (b) a $V_H$ CDR2 region comprising the sequence of the present invention, or an amino acid sequence having one, two, three, four or five amino acid substitutions, deletions or additions; (c) a $V_H$ CDR3 region comprising the sequence of the present invention, or an amino acid sequence having one, two, three, four or five amino acid substitutions, deletions or additions; (d) a $V_L$ CDR1 region comprising the sequence of the present invention, or an amino acid sequence having one, two, three, four or five amino acid substitutions, deletions or additions; (e) a $V_L$ CDR2 region comprising the sequence of the present invention, or an amino acid sequence having one, two, three, four or five amino acid substitutions, deletions or additions; and (f) a $V_L$ CDR3 region comprising the sequence of the present invention, or an amino acid sequence having one, two, three, four or five amino acid substitutions, deletions or additions.

Engineered antibodies of the invention include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α(1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704 and Yamane-Ohnuki et al., (2004) *Biotechnol Bioeng* 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277: 26733-26740). Antibodies with a modified glycosylation profile can also be produced in chicken eggs, as described in PCT Publication WO 06/089231. Alternatively, antibodies with a modified glycosylation profile can be produced in plant cells, such as *Lemna*. Methods for production of antibodies in a plant system are disclosed in the U.S. patent application filed on Aug. 11, 2006. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al., (1999) *Nat. Biotech.* 17:176-180). Alternatively, the fucose residues of the antibody can be cleaved off using a fucosidase enzyme; e.g., the fucosidase α-L-fucosidase removes fucosyl residues from antibodies (Tarentino et al., (1975) *Biochem.* 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EPO 154 316 and EP 0 401 384.

Antibody's Physical Properties

Antibodies of the invention can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp*

*Med* 168:1099-109; Spiro (2002) *Glycobiology* 12:43R-56R; Parekh et al (1985) *Nature* 316:452-7; Mimura et al., (2000) *Mol Immunol* 37:697-706). Glycosylation has been known to occur at motifs containing an N—X—S/T sequence. In some instances, it is preferred to have an anti-PD-1 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a link into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-PD-1 antibody that contains a pI value that falls in the normal range. This can be achieved either by selecting antibodies with a pI in the normal range or by mutating charged surface residues.

Nucleic Acid Molecules Encoding Antibodies of the Invention

In another aspect, the invention provides nucleic acid molecules that encode heavy and/or light chain variable regions, or CDRs, of the antibodies of the invention. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the invention can be, e.g., DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the invention include those encoding the $V_H$ and $V_L$ sequences of the PD-1 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Production of Monoclonal Antibodies of the Invention

Monoclonal antibodies (mAbs) of the present invention can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) *Science* 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) *Mol. Cell. Biol.* 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the invention can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr− CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Immunoconjugates

Antibodies of the invention can be conjugated to a therapeutic agent to form an immunoconjugate such as an antibody-drug conjugate (ADC). Suitable therapeutic agents include cytotoxins, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059,404; WO 08/083,312; and WO 08/103,693; U.S. Patent Publications 20060024317; 20060004081; and 20060247295; the disclosures of which are incorporated herein by reference.

Bispecific Molecules

In another aspect, the present disclosure features bispecific molecules comprising one or more antibodies of the invention linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-Fc binding specificity and an anti-PD-1 binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CD8, CD28, CD4, PD-1, or ICAM-1) or other immune cell, resulting in an increased immune response against the target cell.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv) 2 construct. Intermediate-sized bispecific molecules include two different F(ab) fragments linked by a peptidyl linker. Bispecific molecules of these and other formats can be prepared by genetic engineering, somatic hybridization, or chemical methods.

See, e.g., Kufer et al, cited supra; Cao and Suresh, *Bioconjugate Chemistry*, 9 (6), 635-644 (1998); and van Spriel et al., *Immunology Today*, 21 (8), 391-397 (2000), and the references cited therein.

Antibody-encoding or Antibody-bearing Oncolytic Virus

An oncolytic virus preferentially infects and kills cancer cells. Antibodies of the present invention can be used in conjunction with oncolytic viruses. Alternatively, oncolytic viruses encoding antibodies of the present invention can be introduced into human body.

Pharmaceutical Compositions

In another aspect, the present disclosure provides a pharmaceutical composition comprising one or more antibodies of the present invention formulated together with a pharmaceutically acceptable carrier. The antibodies can be dosed separately when the composition contains more than one antibody. The composition may optionally contain one or more additional pharmaceutically active ingredients, such as another antibody or a drug, such as an anti-tumor drug.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: *The Science and Practice of Pharmacy*, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the antibody, the dosage may range from about 0.0001 to 100 mg/kg, and more usually 0.01 to 5 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-PD-1 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/ml and in some methods about 25-300 µg/ml.

A "therapeutically effective dosage" of an anti-PD-1 antibody of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies of the invention can be formulated to ensure proper distribution in vivo. For example, to ensure that the therapeutic antibody of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

Uses and Methods of the Invention

Antibodies (compositions, bispecifics, immunoconjugates, and other modalities including oncolytic viruses) of the present invention have numerous in vitro and in vivo utilities involving, for example, enhancement of immune responses by blockade of PD-1. The antibodies can be administered to cells in culture, in vitro or ex vivo, or to human subjects, e.g., in vivo, to enhance immunity in a variety of situations. Accordingly, in one aspect, the invention provides a method of modifying an immune response in a subject comprising administering to the subject the antibody, or antigen-binding portion thereof, of the invention such that the immune response in the subject is modified. Preferably, the response is enhanced, stimulated or up-regulated.

Preferred subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-PD-1 antibodies can be administered together with an antigen of interest or the antigen may already be present in the subject to be treated (e.g., a tumor-bearing or virus-bearing subject). When antibodies to PD-1 are administered together with another agents, they can be administered in either order or simultaneously.

Given the ability of anti-PD-1 antibodies of the invention to inhibit the binding of PD-1 to PD-L1 and/or PD-L2 molecules and to stimulate antigen-specific T cell responses, the invention also provides in vitro and in vivo methods of using the antibodies to stimulate, enhance or upregulate antigen-specific T cell responses. For example, the invention provides a method of stimulating an antigen-specific T cell response comprising contacting said T cell with an antibody of the invention, such that an antigen-specific T cell response is stimulated. Any suitable indicator of an antigen-specific T cell response can be used to measure the antigen-specific T cell response.

Non-limiting examples of such suitable indicators include increased T cell proliferation in the presence of the antibody and/or increase cytokine production in the presence of the antibody. In a preferred embodiment, interleukin-2 production by the antigen-specific T cell is stimulated.

The invention also provides method for stimulating an immune response (e.g., an antigen-specific T cell response) in a subject comprising administering an antibody of the invention to the subject such that an immune response (e.g., an antigen-specific T cell response) in the subject is stimulated. In a preferred embodiment, the subject is a tumor-bearing subject and an immune response against the tumor is stimulated. In another preferred embodiment, the subject is a virus-bearing subject and an immune response against the virus is stimulated.

In another embodiment, the invention provides methods for inhibiting growth of tumor cells in a subject comprising administering to the subject an antibody of the invention such that growth of the tumor is inhibited in the subject. In yet another embodiment, the invention provides methods for treating a viral infection in a subject comprising administering to the subject an antibody of the invention such that the viral infection is treated in the subject.

These and other methods of the invention are discussed in further detail below.

Cancer

Blockade of PD-1 by antibodies can enhance the immune response to cancerous cells in the patient. In one aspect, the present invention relates to treatment of a subject in vivo using an anti-PD-1 antibody such that growth of cancerous tumors is inhibited. An anti-PD-1 antibody can be used alone to inhibit the growth of cancerous tumors. Alternatively, an anti-PD-1 antibody can be used in conjunction with other immunogenic agents used in cancer treatments such as oncolytic viruses, or other antibodies, as described below.

Accordingly, in one embodiment, the invention provides a method of inhibiting growth of tumor cells in a subject, comprising administering to the subject a therapeutically effective amount of an anti-PD-1 antibody, or antigen-binding portion thereof. Preferably, the antibody is a mouse, chimeric or humanized anti-PD-1 antibody.

Preferred cancers whose growth may be inhibited using the antibodies of the invention include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer), whether original or metastatic. Additionally, the invention includes refractory or recurrent malignancies whose growth may be inhibited using the antibodies of the invention.

Examples of other cancers that can be treated using the methods of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-1 (Iwai et al. (2005) *Int. Immunol.* 17:133-144).

Optionally, antibodies to PD-1 can be combined with an immunogenic agents, such as cancerous cells, purified tumor antigens (including recombinant proteins, peptides, and carbohydrate molecules), and cells transfected with genes encoding immune stimulating cytokines (He et al (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

PD-1 blockade is likely to be more effective when combined with a vaccination protocol. Many experimental strategies for vaccination against tumors have been devised (see Rosenberg, S., 2000, *Development of Cancer Vaccines*, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., *Cancer Vaccines*, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

The study of gene expression and large scale gene expression patterns in various tumors has led to the definition of so called tumor specific antigens (Rosenberg, SA (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-1 blockade can be used in conjunction with a collection of recombinant proteins and/or peptides expressed in a tumor in order to generate an immune response to these proteins. These proteins are normally viewed by the immune system as self-antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) *Science* 266: 2011-2013). These somatic tissues may be protected from immune attack by various means. Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) Science 269:1585-1588; Tamura et al. (1997) Science 278:117-120).

Dendritic cells (DC) are potent antigen presenting cells that can be used to prime antigen-specific responses. DCs can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) Nature Medicine 6:332-336). As a method of vaccination, DC immunization can be effectively combined with PD-1 blockade to activate more potent anti-tumor responses.

PD-1 blockade can also be combined with standard cancer treatments. PD-1 blockade can be effectively combined with chemotherapeutic regimes. In these instances, it may be possible to reduce the dose of chemotherapeutic reagent administered (Mokyr et al. (1998) *Cancer Research* 58: 5301-5304). An example of such a combination is an anti-PD-1 antibody in combination with decarbazine for the treatment of melanoma. Another example of such a combination is an anti-PD-1 antibody in combination with interleukin-2 (IL-2) for the treatment of melanoma. The scientific rationale behind the combined use of PD-1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-1 blockade through cell death are radiation, surgery, and hormone deprivation. Each of these protocols creates a source of tumor antigen in the host. Angiogenesis inhibitors can also be combined with PD-1 blockade. Inhibition of angiogenesis leads to tumor cell death which may feed tumor antigen into host antigen presentation pathways.

PD-1 blocking antibodies can also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example, anti-Fc receptor/anti-tumor antigen (e.g., Her-2/neu) bispecific antibodies have been used to target macrophages to sites of tumor. This targeting may more effectively activate tumor specific responses. The T cell arm of these responses would be augmented by the use of PD-1 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be used in combination with anti-PD-1 to counteract the effects of the immunosuppressive agent and favor tumor immune responses by the host.

Other antibodies which activate host immune responsiveness can be used in combination with anti-PD-1. These include molecules on the surface of dendritic cells which activate DC function and antigen presentation. Anti-CD40 antibodies are able to substitute effectively for T cell helper activity (Ridge et al. (1998) *Nature* 393: 474-478) and can be used in conjunction with PD-1 antibodies (Ito et al. (2000) *Immunobiology* 201 (5) 527-40). Activating antibodies to T cell costimulatory molecules such as CTLA-4 (e.g., U.S. Pat. No. 5,811,097), OX-40 (Weinberg et al. (2000) *Immunol* 164: 2160-2169), 4-1BB (Melero et al. (1997) *Nature Medicine* 3: 682-685 (1997), and ICOS (Hutloff et al. (1999) *Nature* 397: 262-266) may also provide for increased levels of T cell activation.

There are also several experimental treatment protocols that involve ex vivo activation and expansion of antigen specific T cells and adoptive transfer of these cells into recipients in order to stimulate antigen-specific T cells against tumor (Greenberg & Riddell (1999) *Science* 285: 546-51). These methods can also be used to activate T cell responses to infectious agents such as CMV. Ex vivo activation in the presence of anti-PD-1 antibodies can increase the frequency and activity of the adoptively transferred T cells.

Infectious Diseases

Other methods of the invention are used to treat patients that have been exposed to particular toxins or pathogens. Accordingly, another aspect of the invention provides a method of treating an infectious disease in a subject comprising administering to the subject an anti-PD-1 antibody, or antigen-binding portion thereof, such that the subject is treated for the infectious disease. Preferably, the antibody is a chimeric or humanized antibody.

Similar to its application to tumors as discussed above, antibody mediated PD-1 blockade can be used alone, or as an adjuvant, in combination with vaccines, to stimulate the immune response to pathogens, toxins, and self-antigens. Examples of pathogens for which this therapeutic approach can be particularly useful, include pathogens for which there is currently no effective vaccine, or pathogens for which conventional vaccines are less than completely effective. These include, but are not limited to HIV, Hepatitis (A, B, & C), Influenza, Herpes, *Giardia*, Malaria, *Leishmania, Staphylococcus aureus, Pseudomonas aeruginosa*. PD-1 blockade is particularly useful against established infections by agents such as HIV that present altered antigens over the course of the infections. These novel epitopes are recognized as foreign at the time of anti-human PD-1 administration, thus provoking a strong T cell response that is not dampened by negative signals through PD-1.

Some examples of pathogenic viruses causing infections treatable by methods of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include *Chlamydia*, rickettsial bacteria, mycobacteria, staphylococci, streptococci, pneumonococci, meningococci and gonococci, *Klebsiella, Proteus, Serratia, Pseudomonas, Legionella*, diphtheria, *Salmonella*, bacilli, cholera, tetanus, botulism, anthrax, plague, leptospirosis, and Lymes disease bacteria.

Some examples of pathogenic fungi causing infections treatable by methods of the invention include *Candida (albicans, krusei, glabrata, tropicalis*, etc.), *Cryptococcus neoformans, Aspergillus (fumigatus, niger*, etc.), Genus *Mucorales (mucor, absidia, rhizopus), Sporothrix schenkii, Blastomyces dermatitidis, Paracoccidioides brasiliensis, Coccidioides immitis* and *Histoplasma capsulatum.*

Some examples of pathogenic parasites causing infections treatable by methods of the invention include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis.*

In all of the above methods, PD-1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) *Proc. Natl. Acad. Sci. USA* 90:6444-6448; Poljak (1994) *Structure* 2:1121-1123).

Autoimmune Reactions

Anti-PD-1 antibodies may provoke and amplify autoimmune responses. Indeed, induction of anti-tumor responses using tumor cell and peptide vaccines reveals that many anti-tumor responses involve anti-self reactivities (van Elsas et al. (2001) *J. Exp. Med.* 194:481-489; Overwijk, et al. (1999) *Proc. Natl. Acad. Sci. U.S.A.* 96: 2982-2987; Hurwitz, (2000) supra; Rosenberg & White (1996) *J. Immunother Emphasis Tumor Immunol* 19 (1): 81-4). Therefore, it is possible to consider using anti-PD-1 blockade in conjunction with various self-proteins in order to devise vaccination protocols to efficiently generate immune responses against these self-proteins for disease treatment.

Other self-proteins can also be used as targets such as IgE for the treatment of allergy and asthma, and TNFα for rheumatoid arthritis. Finally, antibody responses to various hormones may be induced by the use of anti-PD-1 antibody. Neutralizing antibody responses to reproductive hormones can be used for contraception. Neutralizing antibody response to hormones and other soluble factors that are required for the growth of particular tumors can also be considered as possible vaccination targets.

Analogous methods as described above for the use of anti-PD-1 antibody can be used for induction of therapeutic autoimmune responses to treat patients having an inappropriate accumulation of other self-antigens, such as cytokines such as TNFα, and IgE.

Combination Therapy

In another aspect, the invention provides methods of combination therapy in which an anti-PD-1 antibody (or antigen-binding portion thereof) of the present invention is co-administered with one or more additional antibodies that are effective in stimulating immune responses to thereby further enhance, stimulate or upregulate immune responses in a subject. In one embodiment, the invention provides a method for stimulating an immune response in a subject comprising administering to the subject an anti-PD-1 antibody and one or more additional immune-stimulatory antibodies, such as an anti-LAG-3 antibody, an anti-PD-L1 antibody and/or an anti-CTLA-4 antibody, such that an immune response is stimulated in the subject, for example to inhibit tumor growth or to stimulate an anti-viral response. In another embodiment, the subject is administered an anti-PD-1 antibody and an anti-LAG-3 antibody. In still another embodiment, the subject is administered an anti-PD-1 antibody and an anti-PD-L1 antibody. In yet another embodiment, the subject is administered an anti-PD-1 antibody and an anti-CTLA-4 antibody. In another embodiment, the at least one additional immune-stimulatory antibody (e.g., anti-PD-1, anti-PD-L1 and/or anti-CTLA-4 antibody) is a human antibody. Alternatively, the at least one additional immune-stimulatory antibody can be, for example, a chimeric or humanized antibody (e.g., prepared from a mouse anti-LAG-3, anti-PD-L1 and/or anti-CTLA-4 antibody).

In another embodiment, the invention provides a method for treating a hyperproliferative disease (e.g., cancer), comprising administering a PD-1 antibody and a CTLA-4 antibody to a subject. In further embodiments, the anti-PD-1 antibody is administered at a subtherapeutic dose, the anti-CTLA-4 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti-PD-1 antibody and a subtherapeutic dose of anti-CTLA-4 antibody to a subject. In certain embodiments, the subject is human. In other embodiments, the anti-CTLA-4 antibody is human sequence monoclonal antibody 10DI (described in PCT Publication WO 01/14424) and the anti-PD-1 antibody is mouse sequence monoclonal antibody, such as anti-PD-1 antibody C1H5 described herein. Other anti-CTLA-4 antibodies encompassed by the methods of the present invention include, for example, those disclosed in: WO 98/42752; WO 00/37504; U.S. Pat. No. 6,207,156; Hurwitz et al. (1998) *Proc. Natl. Acad. Sci. USA* 95(17):10067-10071; Camacho et al. (2004) *J. Clin. Oncology* 22(145): Abstract No. 2505 (antibody CP-675206); and Mokyr et al. (1998) *Cancer Res.* 58:5301-5304. In certain embodiments, the anti-CTLA-4 antibody binds to human CTLA-4 with a $K_D$ of $5\times10^{-8}$ M or less, binds to human CTLA-4 with a $K_D$ of $1\times10^{-8}$ M or less, binds to human CTLA-4 with a $K_D$ of $5\times10^{-9}$ M or less, or binds to human CTLA-4 with a $K_D$ of between $1\times10^{-8}$ M and $1\times10^{-0}$ M or less.

In another embodiment, the present invention provides a method for treating a hyperproliferative disease (e.g., cancer), comprising administering an anti-PD-1 antibody and an anti-LAG-3 antibody to a subject.

In another embodiment, the present invention provides a method for treating a hyperproliferative disease (e.g., cancer), comprising administering an anti-PD-1 antibody and an anti-PD-L1 antibody to a subject.

Blockade of PD-1 and one or more second target antigens such as CTLA-4 and/or LAG-3 and/or PD-L1 by antibodies can enhance the immune response to cancerous cells in the patient. Cancers whose growth may be inhibited using the antibodies of the instant disclosure include cancers typically responsive to immunotherapy. Representative examples of cancers for treatment with the combination therapy of the instant disclosure include those cancers specifically listed above in the discussion of monotherapy with anti-PD-1 antibodies.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). In another example, antibodies to each of these entities can be further combined with an anti-PD-1 and anti-CTLA-4 and/or anti-LAG-3 and/or anti-PD-L1 antibody combination to counteract the effects of immunosuppressive agents and favor anti-tumor immune responses by the host.

Other antibodies that can be used to activate host immune responsiveness can be further used in combination with an anti-PD-1 and anti-CTLA-4 and/or anti-LAG-3 and/or anti-PD-L1 antibody combination. These include molecules on the surface of dendritic cells that activate DC function and antigen presentation. Anti-CD40 antibodies (Ridge et al., supra) can be used in conjunction with an anti-PD-1 and anti-CTLA-4 and/or anti-LAG-3 and/or anti-PD-L1 combination (Ito et al., supra). Other activating antibodies to T cell costimulatory molecules (Weinberg et al., supra, Melero et al. supra, Hutloff et al., supra) may also provide for increased levels of T cell activation.

As discussed above, bone marrow transplantation is currently being used to treat a variety of tumors of hematopoietic origin. A combined PD-1 and CTLA-4 and/or LAG-3 and/or PD-L1 blockade can be used to increase the effectiveness of the donor engrafted tumor specific T cells.

Several experimental treatment protocols involve ex vivo activation and expansion of antigen specific T cells and adoptive transfer of these cells into recipients of antigen-specific T cells against tumor (Greenberg & Riddell, supra). These methods can also be used to activate T cell responses to infectious agents such as CMV. Ex vivo activation in the presence of anti-PD-1 and anti-CTLA-4 and/or anti-LAG-3 and/or anti-PD-L1 antibodies can be expected to increase the frequency and activity of the adoptively transferred T cells.

In certain embodiments, the present invention provides a method for altering an adverse event associated with treatment of a hyperproliferative disease (e.g., cancer) with an immunostimulatory agent, comprising administering an anti-PD-1 antibody and a subtherapeutic dose of anti-CTLA-4 and/or anti-LAG-3 and/or anti-PD-L1 antibody to a subject. For example, the methods of the present invention provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such an antibody, this entire patient population is suitable for therapy according to the methods of the present invention. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a combination of PD-1 with CTLA-4 and/or LAG-3 and/or PD-L1 blockade (i.e., immunostimulatory therapeutic antibodies anti-PD-1 and anti-CTLA-4 and/or anti-LAG-3 antibodies and/or anti-PD-L1 antibodies) can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of the invention, the non-absorbable steroid is budesonide. Budesonide is a locally-acting glucocorticosteroid, which is extensively metabolized, primarily by the liver, following oral administration. ENTOCORT EC™ (Astra-Zeneca) is a pH- and time-dependent oral formulation of budesonide developed to optimize drug delivery to the ileum and throughout the colon. ENTOCORT EC™ is approved in the U.S. for the treatment of mild to moderate Crohn's disease involving the ileum and/or ascending colon. The usual oral dosage of ENTOCORT EC™ for the treatment of Crohn's disease is 6 to 9 mg/day.

ENTOCORT EC™ is released in the intestines before being absorbed and retained in the gut mucosa. Once it passes through the gut mucosa target tissue, ENTOCORT EC™ is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC™ can result in systemic glucocorticoid effects such as hypercorticism and adrenal suppression. See PDR 58$^{th}$ ed. 2004; 608-610.

In still further embodiments, a combination of PD-1 with CTLA-4 and/or LAG-3 and/or PD-L1 blockade (i.e., immunostimulatory therapeutic antibodies anti-PD-1 and anti-CTLA-4 and/or anti-LAG-3 and/or anti-PD-L1 antibodies) in conjunction with a non-absorbable steroid can be further combined with a salicylate. Salicylates include 5-ASA agents such as, for example: sulfasalazine (AZULFIDINE™, Pharmacia & UpJohn); olsalazine (DIPENTUM™, Pharmacia & UpJohn); balsalazide (COLAZAL™, Salix Pharmaceuticals, Inc.); and mesalamine (ASACOL™, Procter & Gamble Pharmaceuticals; PENTASA™, Shire US; CANASA™, Axcan Scandipharm, Inc.; ROWASA™, Solvay).

In accordance with the methods of the present invention, a salicylate administered in combination with anti-PD-1 and anti-CTLA-4 and/or anti-LAG-3 and/or anti-PD-L1 antibodies and a non-absorbable steroid can include any overlapping or sequential administration of the salicylate and the non-absorbable steroid for the purpose of decreasing the incidence of colitis induced by the immunostimulatory antibodies. Thus, for example, methods for reducing the incidence of colitis induced by the immunostimulatory antibodies according to the present invention encompass administering a salicylate and a non-absorbable concurrently or sequentially (e.g., a salicylate is administered 6 hours after a non-absorbable steroid), or any combination thereof. Further, according to the present invention, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the combination of anti-PD-1 with anti-CTLA-4 and/or anti-LAG-3 and/or anti-PD-L1 antibodies.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Generation of Mouse Anti-PD-1 Monoclonal Antibodies Using Hybridoma Technology Immunization Mice were immunized according to the method as described in E Harlow, D. Lane, Antibody: A Laboratory Manual, Cold Spring Harbor Laboratory Press, Cold Spring Harbor, N.Y., 1998. Recombinant human PD-1 protein with human IgG1 Fc tag at the C-terminus (Acro biosystems, #PD-1-H5257, containing extra-cellular domain, AA Leu 25-Gln 167) was used as the immunogen. Human PD-1-his protein (Sino biological, #10377-H08H) was used for determining anti-sera titer and for screening hybridomas secreting antigen-specific antibodies.

In specific, each animal was injected with 25 µg human PD1 Fc protein in complete Freud's adjuvant (Sigma, St. Louis, Mo., USA), and then boosted for 2 to 3 times by injection of 25 µg human PD1 Fc protein in noncomplete Freud's adjuvant (Sigma, St. Louis, Mo., USA) depending on the anti-sera titer. The anti-sera titer was measured by ELISA-based screening using recombinant human PD1-his protein. Briefly, diluted sera (60 µl) was added to each well and incubated at 37° C. for 40 minutes. Plates were then washed 4 times, HRP-goat anti-mouse-IgG (Jackson Immuno research, Cat #115-036-071) was used for detection, and binding ODs were observed at 450 nm. Animals with good titers were given a final boost by intraperitoneal injection before hybridoma fusion.

Hybridoma Fusion and Screening

Cells of murine myeloma cell line (SP2/0-Ag14, ATCC #CRL-1581) were cultured to reach the log phase stage right before fusion. Spleen cells from immunized mice were prepared sterilely and fused with myeloma cells according to the method as described in Kohler G, and Milstein C, "Continuous cultures of fused cells secreting antibody of predefined specificity," Nature, 256: 495-497(1975). Fused "hybrid cells" were subsequently dispensed into 96-well plates in DMEM/20% FCS/HAT media. Surviving hybridoma colonies were observed under the microscope seven to ten days post fusion. After two weeks, the supernatant from each well was subjected to ELISA-based screening using recombinant human PD1-his protein. Briefly, ELISA plates were coated with 60 µl of human PD1-his (Sino biological, #10377-H08H, 2.0 µg/ml in PBS) overnight at 4° C. Plates were washed 4 times with PBST and blocked with 200 µl blocking buffer (5% non-fatty milk in PBST). Diluted hybridoma supernatant (60 µl) was added to each well and incubated at 37° C. for 40 minutes. Plates were then washed 4 times, HRP-goat anti-mouse-IgG (Jackson Immuno research, Cat #115-036-071) was used for detection, and binding ODs were observed at 450 nm. Positive hybridoma secreting antibody that binds to human PD1-his were then selected and transferred to 24-well plates. Hybridoma clones producing antibodies that showed high specific binding and PD1/PDL1 blocking activity were subcloned, and antibodies produced by the subclones were purified by protein A affinity chromatography. Briefly, Protein A sepharose column (from bestchrom(Shanghai) Biosciences, Cat #AA0273) was washed using PBS buffer in 5 to 10 column volumes. Cell supernatants were passed through the columns, and then the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris-HCl, pH 9.0). Fractions containing IgG were pooled and dialyzed in PBS overnight at 4° C.

Example 2 Affinity Determination of Mouse Anti-PD-1 Monoclonal Antibodies Using BIACORE Surface Plasmon Resonance Technology The purified anti-PD-1 mouse monoclonal antibodies (mAbs) generated in Example 1, having heavy/light chain variable region sequences as set forth in Table 1 above and heavy/light chain constant region sequences of SEQ ID NO.:

129 and 130, respectively, were characterized for affinities and binding kinetics by Biacore T200 system (GE healthcare, Pittsburgh, PA, USA).

Briefly, goat anti-mouse IgG (GE healthcare, Cat #BR100839, Human Antibody Capture Kit) was covalently linked to a CM5 chip (carboxy methyl dextran coated chip) via primary amines, using a standard amine coupling kit (GE healthcare, Pittsburgh, PA, USA) provided by Biacore. Unreacted moieties on the biosensor surface were blocked with ethanolamine. Then purified anti-PD-1 antibodies and Nivolumab (OPDIVO®) at the concentration of 66.7 nM were flowed onto the chip at a flow rate of 10 µL/min. Then, recombinant human PD-1-his (Sino biological, #10377-H08H) or cynomolgus monkey PD-1-his protein (Acro biosystems, #PD-1-C5223) in HBS EP buffer (provided by Biacore) was flowed onto the chip at a flow rate of 30 µL/min. The antigen-antibody association kinetics was followed for 2 minutes and the dissociation kinetics was followed for 10 minutes. The association and dissociation curves were fit to a 1:1 *Langmuir* binding model using BIA evaluation software.

The $k_a$, $k_d$ and $K_D$ values were determined and shown in Table 2 below.

TABLE 2

Biacore Kinetics of Mouse Anti-PD-1 Monoclonal Antibodies Binding to Human or Cynomolgus Monkey PD-1

| | Kinetics on Biacore | | | | | |
| --- | --- | --- | --- | --- | --- | --- |
| | Human PD-1 | | | Cynomolgus PD-1 | | |
| Clone | $K_a$ $(M^{-1}s^{-1})$ | $K_d$ $(s^{-1})$ | $K_D$ (M) | $K_a$ $(M^{-1}s^{-1})$ | $K_d$ $(s^{-1})$ | $K_D$ (M) |
| D1F2 | 1.94E+05 | 2.03E−04 | 1.05E−09 | 2.00E+05 | 0.006324 | 3.17E−08 |
| C1F5 | 3.53E+05 | 1.31E−04 | 3.72E−10 | 1.38E+05 | 0.002489 | 1.81E−08 |
| C1E1 | 1.72E+05 | 5.88E−05 | 3.42E−10 | 2.03E+05 | 7.89E+04 | 3.90E−09 |
| D1A1 | 1.88E+05 | 3.86E−04 | 2.06E−09 | 2.10E+05 | 0.002358 | 1.13E−08 |
| D1F1 | 2.04E+05 | 5.77E−04 | 2.83E−09 | 2.60E+04 | 0.002919 | 1.12E−07 |
| C1E2 | 1.53E+05 | 4.42E−04 | 2.88E−09 | 2.38E+05 | 0.002978 | 1.25E−08 |
| C1A1 | 1.68E+05 | 1.89E−04 | 1.13E−09 | 3.48E+05 | 3.31E−03 | 9.50E−09 |
| C1F4 | 1.56E+05 | 3.59E−04 | 2.30E−09 | 3.01E+05 | 0.005208 | 1.73E−08 |
| D2C2 | 1.73E+05 | 3.07E−04 | 1.77E−09 | 2.06E+04 | 0.00238 | 1.16E−07 |
| 2G2 | 1.63E+05 | 4.36E−04 | 2.68E−09 | 1.40E+05 | 1.83E−03 | 1.30E−08 |
| C1C5 | 2.31E+05 | 2.03E−04 | 8.80E−10 | 3.22E+05 | 4.70E−03 | 1.46E−08 |
| OPDIVO ® | 4.33E+05 | 1.41E−03 | 3.25E−09 | / | / | / |

The antibodies of the present invention bound to human PD-1 specifically with a lower $K_D$ than Nivolumab, indicating higher affinity to human PD-1.

Example 3 Binding Activity of Mouse Anti-PD-1 Monoclonal Antibodies 96-well micro plates were coated with 2 µg/ml goat anti-mouse IgG Fcγ fragment (Jackson Immuno Research, #115-006-071,100 µl/well) in PBS and incubated overnight at 4° C. Plates were washed 4 times with wash buffer (PBS+0.05% Tween-20, PBST) and then blocked with 200 µl/well blocking buffer (5% w/v non-fatty milk in PBST) for 2 hours at 37° C. Plates were washed again and incubated with 100 µl/well purified anti-PD-1 antibodies of Example 1 and Nivolumab (0.004-66.7 nM, 5-fold serial dilution in 2.5% non-fatty milk in PBST) for 40 minutes at 37° C., and then washed 4 times again. Plates containing captured anti-PD-1 antibodies were incubated with biotin-labeled human PD-1 Fc protein (SEQ ID NO: 100, 60 nM in 2.5% non-fatty milk in PBST, 100 µl/well) for 40 minutes at 37° C., washed 4 times, and incubated with streptavidin conjugated HRP (1:10000 dilution in PBST, Jackson Immuno Research, #016-030-084, 100 µl/well) for 40 minutes at 37° C. After a final wash, plates were incubated with 100 µl/well ELISA substrate TMB (Innoreagents). The reaction was stopped in 15 minutes at 25° C. with 50 µl/well 1M $H_2SO_4$, and the absorbance was read at 450 nm. Data were analyzed using Graphpad Prism software and $EC_{50}$ values were reported.

The results were summarized in Table 3 below.

TABLE 3

Binding Activity of anti-PD-1 antibodies to Human PD-1

| Clone | Capture ELISA ($EC_{50}$, nM) |
| --- | --- |
| D1F2 | 0.19 |
| C1F5 | 0.16 |
| C1E1 | 0.16 |
| D1A1 | 0.2 |
| D1F1 | 0.24 |
| C1E2 | 0.2 |

TABLE 3-continued

Binding Activity of anti-PD-1 antibodies to Human PD-1

| Clone | Capture ELISA ($EC_{50}$, nM) |
| --- | --- |
| C1A1 | 0.18 |
| C1F4 | 0.25 |
| D2C2 | 0.2 |
| 2G2 | 0.18 |
| C1C5 | 0.16 |
| OPDIVO ® | 0.21 |

The result indicated that the antibodies of the present invention bound to human PD-1 specifically, with several clones having lower $EC_{50}$ values than Nivolumab.

Example 4 Functional Blockage Assays Using ELISA and Report Assays 4.1 Ligand Blocking ELISA The ability of anti-PD-1 antibodies of the present invention to block the PD-1-PD-L1 interaction was measured using a competitive ELISA assay. Briefly, human PD-L1-Fc proteins (SEQ ID NO:101) were coated on 96-well micro plates at 2 µg/mL PBS and incubated overnight at 4° C. The next day, plates were washed with wash buffer (PBS+0.05% Tween-20, PBST), and blocked with 5% non-fatty milk in PBST for 2 hours at 37° C. Plates were then washed again using wash buffer.

Dilutions of the anti-PD-1 antibodies of the present invention or Nivolumab (starting at 100 nM with a four-fold serial dilution) in biotin labeled human PD-1-Fc (SEQ ID NO: 100, 10 nM in 2.5% non-fatty milk in PBST) were prepared and incubated at room temperature for 40 minutes, and then the antibodies/PD-1-Fc-biotin mixtures (100 µl/well) were added to PD-L1-coated plates. After incubation at 37° C. for 40 minutes, plates were washed for 4 times using wash buffer. Then 100 µl/well streptavidin conjugated HRP was added and incubated for 40 minutes at 37° C. to detect biotin-labeled human PD-1 bound to PD-L1. Plates were washed again using wash buffer. Finally, TMB was added and the reaction was stopped using 1M $H_2SO_4$, and the absorbance was read at 450 nm. Data were analyzed using Graphpad Prism software and $IC_{50}$ values were reported.

4.2 Benchmark Blocking ELISA

The ability of the anti-PD-1 antibodies of the present invention to block Benchmark (Nivolumab)-human PD-1 binding was measured using a competitive ELISA assay. Briefly, Nivolumab was coated on 96-well micro plates at 2 µg/mL in PBS and incubated overnight at 4° C. The next day, plates were washed with wash buffer, and blocked with 5% non-fatty milk in PBST for 2 hours at 37° C. While blocking, biotin labeled human PD-1 Fc (SEQ ID NO:100, 10 nM in 2.5% non-fatty milk in PBST) was mixed with each of the antibodies to test (137 pM-100 nM, 3-fold serial dilution) and incubated for 40 minutes at 25° C. After washing, the PD-1/antibody mixtures (100 µl/well) were added to plates coated with Nivolumab and incubated for 40 minutes at 37° C. Plates were washed again with wash buffer, and then 100 µl/well SA-HRP was added and incubated for 40 minutes at 37° C. to detect biotin-labeled human PD-1 bound to Opdivo©. Plates were finally washed using wash buffer. TMB was added and the reaction was stopped using 1M $H_2SO_4$, and the absorbance was read at 450 nm. Data were analyzed using Graphpad Prism software and $IC_{50}$ values were reported.

4.3 Cell-Based Functional Assays

The activity of antibodies to block cell membrane PD-1/PD-L1 interaction was evaluated by using a cell-based reporter assay. This assay consisted of two genetically engineered cell lines, PD-1 Effector Cell Line (Genscript, GS-J2/PD-1) stably expressing human PD-1 and a luciferase reporter driven by an NFAT response element (NFAT-RE), and PD-L1 Cell Line (Genscript, GS-C2/PD-L1, APC cells) stably expressing human PD-L1 and an engineered cell surface protein-antigenic peptide/major histocompatibility complex (MHC). When these two cell lines were co-cultured, the T-cell receptor (TCR)-mediated luciferase expression of PD-1 effector cell (via of the NFAT pathway) was inhibited by PD-1/PD-L1 interaction.

The cell-based functional assay was carried out as follows. Briefly, PD-L1 cells at the log phase stage were seeded into 384-well cell culture plates at the density of $5*10^5$/ml. The next day, dilution of anti-PD-1 antibodies of the present invention or Nivolumab (starting from 333.3 nM, 5-fold serial dilution) in assay buffer (RPMI 1640+1% FBS) were prepared. Meanwhile, the media of PD-L1 cells in 384-well plates were discarded, and then the dilutions of anti-PD-1 antibodies (20 µl/well) and PD-1 effector cells (at the density of $6.25*10^5$/ml, 20 µl/well) were added to 384-well cell culture plates. After co-cultured at 37° C. for six hours, the plates were removed from the incubator and the luminescence of each well was read according to the manufacturer's instructions with One-Glo Luciferase Assay system (Promega, #E6120). The dose-response curves were analyzed using Graphpad Prism software and $EC_{50}$ values were reported.

The results of the three assays were summarized in Table 4 below.

TABLE 4

Anti-PD-1 antibodies' Capacity for Blocking PD-1/PD-L1 interaction

| Clone | Functional Blockage Assays Competition ELISA ($IC_{50}$, nM) | | Reporter Activation ($EC_{50}$, nM) human PD-1 cell |
|---|---|---|---|
| | human PD-1/ human PD-L1 | Opdivo ®/ human PD-1 | (NFAT-luc)/ human PD-L1 cell |
| D1F2 | 0.21 | 1.4 | 7.349 |
| C1F5 | 0.21 | 0.87 | 7.579 |
| C1E1 | 0.26 | 1.1 | 9.114 |
| D1A1 | 0.22 | 1.28 | 9.128 |
| D1F1 | 0.2 | 2.13 | 10.84 |
| C1E2 | 0.25 | 1.49 | 11.13 |
| C1A1 | 0.27 | 1.4 | 12.14 |
| C1F4 | 0.43 | 2.26 | 13.24 |
| D2C2 | 0.21 | 1.89 | 14.67 |
| 2G2 | 0.32 | 14.45 | 17.86 |
| C1C5 | 0.23 | 1.34 | 23.36 |
| OPDIVO ® | 0.12 | 3.79 | 13.62 |

It can be seen that the antibodies of the present invention were capable of blocking human PD-1/human PD-L1 interaction, with several clones having lower $EC_{50}$ or $IC_{50}$ values than Nivolumab.

The data also showed that the antibodies of the present invention were able to block human PD-1/Nivolumab interaction, wherein antibodies from Clone 2G2 had partial blocking, indicating they bound to the same or similar epitope as Nivolumab did.

Example 5 Generation and Characterization of Chimeric Antibodies

The variable domains of the heavy and light chain of the anti-PD1 mouse mAb C1E1 were cloned in frame to human IgG1 heavy-chain and human kappa light-chain constant regions, respectively. The heavy chain variable region and the light chain variable region had amino acid sequences set forth in SEQ ID NOs.: 67 and 80, respectively, while the amino acid sequences of the human IgG1 heavy-chain and human kappa light-chain constant regions were set forth in SEQ ID NOs.: 97 and 98, respectively. The activities of the resulting chimeric antibodies were confirmed in binding capture ELISA, competition ELISA and cell-based functional reporter assay following the protocols in the foregoing Examples. The data showed that the chimeric C1E1 antibody had activities comparable to those of the benchmark (OPDIVO®), as shown in Table 5 below.

TABLE 5

Binding and functional activities of Chimeric Antibodies

| Clone ID# | Capture binding ELISA ($EC_{50}$, nM) | PD1/PDL1 ligand blocking ELISA ($IC_{50}$, nM) | Benchmark blocking ELISA ($IC_{50}$, nM) | Cell-based functional reporter assay ($IC_{50}$, nM) |
|---|---|---|---|---|
| Chimeric C1E1 | 0.23 | 0.53 | 0.20 | 8.53 |
| OPDIVO ® | 0.37 | 0.41 | 0.38 | 10.32 |

Example 6 Humanization of Anti-PD-1 Mouse Monoclonal Antibody C1E1

Mouse anti-PD1 antibody C1E1 was selected for humanization and further investigations. Humanization of the mouse antibody was conducted using the well-established CDR-grafting method as described in detail below.

To select acceptor frameworks for humanization of mouse antibody C1E1, the light and heavy chain variable region sequences of mouse C1E1 were blasted against the human immunoglobulin gene database. The human germline IGVH and IGVK with the highest homology to mouse C1E1 were selected as the acceptor frameworks for humanization. The mouse antibody heavy/light chain variable region CDRs were inserted the selected frameworks, and the residue(s) in the frameworks was/were further mutated to obtain more candidate heavy chain/light chain variable regions.

The vectors containing nucleotide sequences encoding humanized C1E1 heavy chain/light chain variable regions and human IgG1 heavy-chain and human kappa light-chain constant regions were transiently transfected into 50 ml of 293F suspension cell cultures in a ratio of 60% to 40% light to heavy chain construct, with 1.2 mg/ml PEI. Cell supernatants were harvested after six days in shaking flasks, spun down to pellet cells, and filtered through 0.22 μm filters before IgG separation. The antibodies were purified by protein A affinity chromatography. Briefly, Protein A sepharose column (from bestchrom (Shanghai) Biosciences, Cat #AA0273) was washed using PBS buffer in 5 to 10 column volumes. Cell supernatants were passed through the columns, and then the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris-HCl, pH 9.0). Fractions containing IgG were pooled and dialyzed in PBS overnight at 4° C.

A total of 10 humanized antibodies were obtained, 8 of which were further characterized, namely from huC1E1-V1 to huC1E1-V7 and huC1E1-V10. The heavy chain/light chain variable region amino acid sequences of the 8 antibodies were summarized in Table 1 above, and the human IgG1 heavy-chain and human kappa light-chain constant region sequences were set forth in SEQ ID NOs.: 97 and 98, respectively.

The binding affinity of huC1E1-V1 to huC1E1-V7 to human PD1 were assessed by the BIACORE technology as described in Example 2, and the affinities $K_D$ values were summarized in Table 6 below. Antibody huC1E1-V10 was assessed for its binding activity to human PD1 through a capture binding ELISA as describe in Example 3, which utilized a goat anti-human IgG Fab capture antibody (Jackson ImmunoResearch, Cat #109-005-097) to capture IgG, and the binding $EC_{50}$ values were summarized in Table 7. All 8 humanized antibodies had comparable affinities to the chimeric antibody C1EL.

TABLE 6

Affinities of Humanized C1E1 mAbs

| mAb | Human PD1 Biacore (KD, M) |
|---|---|
| huC1E1-V1 | 3.88E−09 |
| huC1E1-V2 | 2.49E−09 |
| huC1E1-V3 | 4.52E−09 |
| huC1E1-V4 | 2.95E−09 |
| huC1E1-V5 | 3.37E−09 |
| huC1E1-V6 | 3.05E−09 |
| huC1E1-V7 | 6.36E−09 |
| huC1E1-V10 | 9.68E−10 |
| Chimeric C1E1 | 1.83E−09 |
| OPDIVO ® | 1.49E−08 |

TABLE 7

Binding Activities of Humanized C1E1 mAb

| mAb | Human PD1 Binding capture ELISA ($EC_{50}$, nM) |
|---|---|
| huC1E1-V10 | 0.44 |
| Chimeric C1E1 | 0.16 |
| OPDIVO ® | 1.19 |

The humanized antibody huC1E1-V10 was then tested for the affinity for human and cynomolgus PD1 by Biacore and by binding capture ELISA, and also tested for the functional activities by competition ELISA and by cell-based reporter assay, following the protocols in Examples 2 to 4. As showed in Table 8, huC1E1-V10 showed comparable in vitro activities to the chimeric C1E1 antibody.

TABLE 8

Binding and Functional activities of Humanized C1E1 mAb Summary of

| | Binding assay | | | Functional assay | | Cell-based reporter assay ($EC_{50}$, nM) |
|---|---|---|---|---|---|---|
| | Human PD1 | | Cynomolgus | Competition ELISA ($IC_{50}$, nM) | | |
| mAbs | Binding ELISA ($EC_{50}$, nM) | Biacore (KD, M) | PD1 Biacore (KD, M) | PD1/PDL1 ligand blocking ELISA | Benchmark blocking ELISA | |
| huC1E1-V10 | 0.34 | 9.68E−10 | 8.92E−10 | 0.88 | 0.35 | 11.26 |
| chC1E1 | 0.23 | 8.81E−10 | 8.45E−10 | 0.53 | 0.20 | 8.53 |
| OPDIVO ® | 0.37 | 8.17−09 | 1.40E−08 | 0.41 | 0.38 | 10.32 |

Example 7 Physicochemical Properties of Humanized C1E1 Antibody

Physicochemical Properties of the anti-PD1 humanized antibody huC1E1-V10 were examined by using Protein Thermal Shift assay, cIEF Technique, SEC Technique and Freeze-Thaw Method as described below.

Protein Thermal Shift Assay to Determine Tm

The thermal stability of the anti-PD1 humanized antibody huC1E1-V10 was measured using a GloMelt™ Thermal Shift Protein Stability Kit (Biotium, Cat #33022-T, lot #: 181214). Briefly, GloMelt™ dye was allowed to thaw and reach room temperature. The vial containing the dye was vortexed and centrifuged. 10× dye was prepared by adding 5 μL 200× dye to 95 μL PBS. 2 μL 10× dye and 10 μg antibody were added in a total 20 μL reaction volume. The run of a melt curve program having detailed parameters in Table 9 was set up. Tubes were spun briefly and placed in real-time PCR thermocycler (Roche, LightCycler 480 II). The results were analyzed using Microsoft Excel 2010 software.

TABLE 9

Parameters for Melt Curve Program

| Profile step | Temperature | Ramp rate | Holding Time |
|---|---|---|---|
| Initial hold | 25° C. | NA | 30 s |
| Melt curve | 25-99° C. | 0.1° C./s | NA | cIEF Technique to Determine pI

Capillary isoelectric focusing (cIEF) was used to determine the pI and charge heterogeneity of the anti-PD1 humanized antibody huC1E1-V10. Briefly, 35 μL 0.1% MC, 4 μL pH3-10 Pharmlyte, 2 μL 0.5 mol/L Arg, 1 μL Mark-7.05 and 1 μL Mark-9.99 were added to a tube containing 20 μg antibody in PBS, then ddH₂O was added up to 100 μL. The electrophoresis program consisted of two phases: initial separation for 1 minute at 1500 V followed by 6 minutes at 3000 V. After 5 min exposures for detection, data were analyzed using Maurice™ Compass™ software (Proteinsimple Inc., USA).

SEC Technique to Determine Aggregation

The percentage of monomer was assessed with size exclusion chromatography (SEC) (Agilent Technologies, 1260 Infinity II). Antibodies were carried in an aqueous mobile phase and passed through a porous stationary phase resin packed in a column. The retention time in the column was a function of the hydrodynamic size of the protein and the size of the pores in the packed resin bed. Smaller molecules can penetrate into smaller pores in the resin and were retained longer than larger molecules. Upon elution from the column, the proteins were detected by UV absorbance. The mobile phase was a phosphate-buffered saline solution and the absorbance was monitored at 280 nm. The flow rate was 0.8 mL/minute. Injection volume was 40 μL of 1 mg/mL sample. The column temperature was room temperature. The auto-sampler temperature was 2-8° C. The total run time was 25 minutes.

Freeze-Thaw Method to Determine Stability

Antibody solutions at 1 mg/ml in 1×PBS formulation(s) (containing 137 mmol/L NaCl, 2.7 mmol/L KCl, 10 mmol/L Na₂HPO₄·12H₂O, 2 mmol/L KH₂PO₄) were frozen at −80° C. for at least 24 hours and then thawed at room temperature for 30-60 minutes. The freeze and thaw cycle was repeated 5 times for each sample. After certain freeze-thaw cycles, e.g., second, third and fourth, a portion of the solution was withdrawn for analysis by SEC before refreezing.

Figure 2:
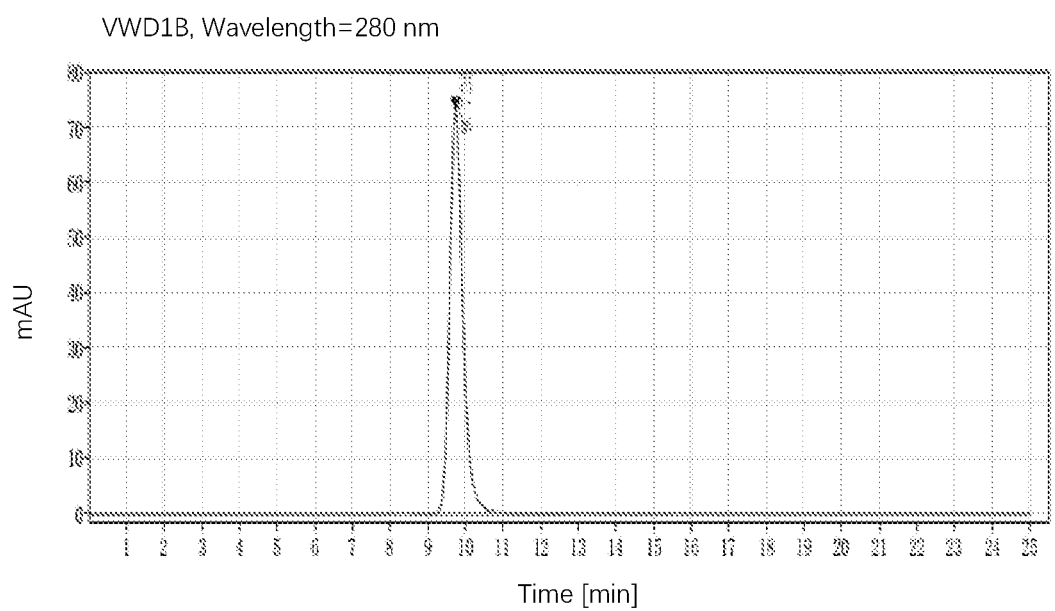
FIG. 2 shows the result of size exclusion chromatography of humanized anti-PD-1 antibody huC1E1-V10.

Instability leading to denaturation was assessed by a GloMelt™ Thermal Shift Protein Stability Kit. As shown in FIG. 1, anti-PD1 humanized antibody huC1E1-V10 showed high melting temperature (Tm) typically at 78° C. and also a minor peak at 69.5° C. The cIEF assay for huC1E1-V10 indicated that the % Major Isoform was about 81.5%, the % Acidic Species was about 11.0% and the % Basic Species was about 7.5%. The pIs were calculated using Maurice™ Compass™ software, and the pI value of huC1E1-V10 antibody was 8.36. The huC1E1-V10 humanized antibody had a pI significantly above 7 and therefore expected to have a significant positive charge at neutral pH. SEC test for huC1E1-V10 indicated that the % Monomer was 100.0% (see FIG. 2). Stability to freezing and thawing was assessed by size exclusion chromatography (SEC). Antibody huC1E1-V10 showed no apparent increase in level of aggregation over time, and no precipitation or cloudiness was observed after 5 times of repeated freezing and thawing.

Example 8 In Vivo Anti-Tumor Efficacy of Mouse C1E1 Antibody

In vivo anti-tumor activity of mouse C1E1 antibody was evaluated in NCG mice. Briefly, NCG mice were subcutaneously injected with 4×10⁶ human melanoma A375 cells mixed with 5×10⁵ tumor reactivated PBMCs at the right axilla on Day 1. Tumor volumes were measured twice a week for three weeks using electronic caliper and calculated as (length×width²)/2. Twenty-four tumor-bearing mice were selected and randomized into four groups on Day 14. The animals were intraperitoneally administered with vehicle (5% Glucose Solution), mouse C1E1, mouse C1E1 Fab, and Nivolumab, respectively at a dose of 3 mg/kg, on Day 14, 21 and 28. The mouse antibody C1E1 contained mouse heavy chain variable region and human IgG1 constant region as well as mouse light chain variable region and human Ck1 constant region having the sequences set forth in SEQ ID NOs: 67, 97, 80 and 98, respectively, while mouse C1E1 Fab contained mouse heavy chain variable domain and human IgG1 CH1 constant domain as well as light chain variable domain and human Ck1 constant domain having the sequences set forth in SEQ ID NOs: 67, 99, 80 and 98, respectively.

The mice were euthanized on Day 35, and tumors were collected and weighed. Tumor growth inhibition (% TGI= (1−mean tumor volume in each treatment group/mean tumor volume in control group)×100%) was calculated.

All treatments were well tolerated by the tumor-bearing animals. As can be seen in Table 10, both mouse C1E1 treatment at 3 mg/kg and mouse C1E1 Fab treatment at 3 mg/kg had significantly better efficacy than Nivolumab at 3 mg/kg on humane melanoma A375 xenograft model.

TABLE 10

Anti-tumor Efficacy of Mouse C1E1 Antibody in the Human melanoma cell A375 Xenograft Model

| Group No. | Drug | Dose | Tumor Volume$^a$ (mm$^3$) | % TGI | Tumor weight (g) |
|---|---|---|---|---|---|
| 1 | Vehicle | n/a | 509.22 ± 132.69 | — | 0.61 ± 0.20 |
| 2 | Mouse C1E1 | 3 mg/kg | 116 ± 40.33* | 77.22% | 0.13 ± 0.06 |
| 3 | Mouse C1E1 Fab | 3 mg/kg | 91.38 ± 33.17* | 82.05% | 0.11 ± 0.04 |
| 4 | OPDIVO ® | 3 mg/kg | 276.47 ± 124.61 | 45.71% | 0.28 ± 0.12 |

$^a$Compared with vehicle control group by student's t test, *P < 0.05.

Example 9 In Vivo Anti-Tumor Efficacy of Herpes Virus T3011 Inserted with Mouse C1E1-Encoding Sequences The anti-tumor efficacy of Herpes Virus T3011 inserted with the mouse C1E1 antibody-encoding sequences was evaluated on B16F10-hPD-L1 melanoma Xenograft Model.

Herpes Virus T3011 is genetically modified Herpes Simplex Virus Type 1 (HSV-1) by removing Inverted Repeat Region and replaced by human IL-12 gene (see, e.g., PCT/CN2016/080025), in addition to insertion of C1E1 Fab fragment sequence into the genomic region between UL3-UL4. C1E1 Fab sequence contains mouse heavy chain variable domain and human IgG1 CH1 constant domain as well as mouse light chain variable domain and human Ckappa1 constant domain having the sequences set forth in SEQ ID NOs: 67, 99, 80 and 98, respectively.

Briefly, female B-hPD-1 humanized mice were subcutaneously injected with 1×10$^5$ B16F10-hPD-L1 melanoma cells at the right anterior flank. When tumor volumes reached approximately 90 mm$^3$, the mice were randomized into five groups, with 8 mice in each group. These mice were intratumorally administered with vehicle (5% Glucose Solution), T3011 (5×10$^6$ PFU/mouse), T3011 (1×10$^7$ PFU/mouse), T3011 (3×10$^7$ PFU/mouse) and NV1020 (3×10$^7$ PFU/mouse, a recombinant oncolytic HSV-based virus, being developed by MediGene (formerly NeuroVir) for the potential cancer treatment, see e.g, Phase I/II study of oncolytic herpes simplex virus NV1020 in patients with extensively pretreated refractory colorectal cancer metastatic to the liver. Hum Gene Ther. 2010 September; 21(9): 1119-28), respectively. Tumor volumes were measured twice a week.

Twelve days after drug administration, the mice were euthanized and tumors were collected, weighted and photographed. Relative tumor volume (RTV=TVn/TV$_0$, where TVn referred to the tumor volume at day n and TV$_0$ referred to the tumor volume at day 0), tumor growth inhibition rate (TGI %=1-mean tumor volume in each treatment group/mean tumor volume in control group)×100%) and tumor weight inhibition rate (IR$_{TW}$=(1−mean tumor weight in each treatment group/mean tumor weight in control group)× 100%) were calculated.

As showed in Table 11 below, T3011 inserted with the mouse C1E1 antibody-encoding sequences provided evident anti-tumor activity in a dose-dependent manner. T3011 administration showed better anti-tumor efficacy than NV1020 administration at 3×10$^7$ PFU/mouse dose level.

TABLE 11

Anti-tumor Efficacy of Herpes Virus T3011 Inserted with Mouse C1E1-encoding Sequences against B16F10-hPD-L1 melanoma Xenograft Model

| Group No. | Drug | Dose | Tumor Volume$^a$ (mm$^3$) | TGI (%) | IR$_{TW}$ |
|---|---|---|---|---|---|
| 1 | Vehicle | n/a | 3396 ± 836 | — | — |
| 2 | T3011 | 5 × 10$^6$ PFU/mouse | 1724 ± 471* | 50.6% | 18.9% |
| 3 | T3011 | 1 × 10$^7$ PFU/mouse | 1365 ± 361* | 61.4% | 28.4% |
| 4 | T3011 | 3 × 10$^7$ PFU/mouse | 458 ± 128** | 88.9% | 73.6% |
| 5 | NV1020 | 3 × 10$^7$ PFU/mouse | 1277 ± 423* | 64.1% | 41.2% |

$^a$Compared with vehicle control group by student's t test, *P < 0.05 and **P < 0.01.

Example 12 In Vivo Anti-Tumor Efficacy of Humanized C1E1 Antibody

The effect of humanized C1E1 antibodies on tumor growth was evaluated on MC38 xenograft model. Briefly, female B-hPD-1 mice were subcutaneously injected with 5×10$^5$ cells at the right hind flank. When tumor volumes reached about 100-150 mm$^3$, mice were randomly divided into 7 groups, 8 mice/group. The animals were intraperitoneally administered with vehicle (PBS), huC1E1-V10 and OPDIVO@, respectively, at a dose of 1 mg/kg, 3 mg/kg or 10 mg/kg, twice a week, for three weeks. The humanized antibody huC1E1-V10 contained heavy chain variable region and constant region as well as light chain variable region and constant region having the sequences set forth in SEQ ID NOs: 69, 97, 86 and 98, respectively. Tumor volumes were measured during the study.

Twenty-three days after treatment initiation, mice were were euthanized and tumors were collected, weighted and photographed. Tumor volume growth inhibition rate (TGI$_{TV}$) were calculated and showed in Table 12.

As showed in Table 12 below, all treatments were tolerated well by the tumor-bearing animals. HuC1E1-V10 treatments showed anti-tumor activity in MC38 xenograft model in a dose-dependent manner, which was comparable to OPDIVO@.

TABLE 12

Anti-tumor Efficacy of huC1E1-V10 in MC38 xenograft model

| Group No. | Drug | Treatment Group | Tumor Volume[a] (mm³) | $TGI_{TV}$ (%) |
|---|---|---|---|---|
| 1 | Vehicle | n/a | 3438 ± 571 | — |
| 2 | huC1E1-V10 | 1 mg/kg | 2357 ± 410 | 32.6 |
| 3 | huC1E1-V10 | 3 mg/kg | 1335 ± 241* | 63.4 |
| 4 | huC1E1-V10 | 10 mg/kg | 1189 ± 250* | 67.8 |
| 5 | OPDIVO ® | 1 mg/kg | 1255 ± 139 | 65.9 |
| 6 | OPDIVO ® | 3 mg/kg | 1444 ± 190** | 60.2 |
| 7 | OPDIVO ® | 10 mg/kg | 703 ± 151* | 82.5 |

[a] Compared with vehicle control group by student's t test, *P < 0.05 and **P < 0.01.

While the invention has been described above in connection with one or more embodiments, it should be understood that the invention is not limited to those embodiments, and the description is intended to cover all alternatives, modifications, and equivalents, as may be included within the spirit and scope of the appended claims. All referenced cited herein are further incorporated by reference in their entirety.

```
Description/Sequence/SEQ ID NO.

VH-CDR1 for C1EL huC1E1-V1 - huC1E1-V7 and huC1E1-V10
GFTFSSYL (SEQ ID NO: 1)

VH-CDR2 for C1EL huC1E1-V1 - huC1E1-V7 and huC1E1-V10
ISGGGGDT (SEQ ID NO: 2)

VH-CDR3 for C1EL huC1E1-V1 - huC1E1-V7 and huC1E1-V10
VRFGGAGYYWYFD (SEQ ID NO: 3)

VH-CDR1 for D1F2
GFTFSSYT (SEQ ID NO: 4)

VH-CDR2 for D1F2
ISGGGSNI (SEQ ID NO: 5)

VH-CDR3 for D1F2
VLNYAYAMDYWGQ (SEQ ID NO: 6)

VH-CDR1 for C1F5
GFAFSSYD (SEQ ID NO: 7)

VH-CDR2 for C1F5
ITGGGSSS (SEQ ID NO: 8)

VH-CDR3 for C1F5
ASPYLSYFDYWGQ (SEQ ID NO: 9)

VH-CDR1 for D1A1
GFTFSNYA (SEQ ID NO: 10)

VH-CDR2 for D1A1
ISGGGGNI (SEQ ID NO: 11)

VH-CDR3 for D1A1
ASPYANYVWYLDV (SEQ ID NO: 12)

VH-CDR1 for D1F1
GFTFSSNT (SEQ ID NO: 13)

VH-CDR2 for D1F1
ISGGGVNT (SEQ ID NO: 14)

VH-CDR3 for D1F1
ARHGNYNYYGMDY (SEQ ID NO: 15)

VH-CDR1 for C1E2
GYTFTNYW (SEQ ID NO: 16)

VH-CDR2 for C1E2
IYPGGGYT (SEQ ID NO: 17)

VH-CDR3 for C1E2
ARGYGTNYWYFDV (SEQ ID NO: 18)

VH-CDR1 for C1A1
GFSLSTSGMG (SEQ ID NO: 19)
```

| Description/Sequence/SEQ ID NO. |
|---|

-continued

VH-CDR2 for C1A1
IWWDDDK (SEQ ID NO: 20)

VH-CDR3 for C1A1
ARTGGFITTGYWY (SEQ ID NO: 21)

VH-CDR1 for C1F4
GYKFTDYA (SEQ ID NO: 22)

VH-CDR2 for C1F4
ISTYSGDV (SEQ ID NO: 23)

VH-CDR3 for C1F4
SRLGITAGFAYWG (SEQ ID NO: 24)

VH-CDR1 for D2C2
GFTFSSNT (SEQ ID NO: 25)

VH-CDR2 for D2C2
ISGGGVDT (SEQ ID NO: 26)

VH-CDR3 for D2C2
ARHGNYNYYGMDY (SEQ ID NO: 27)

VH-CDR1 for 2G2
GFTFSYYG (SEQ ID NO: 28)

VH-CDR2 for 2G2
ISSGSSFT (SEQ ID NO: 29)

VH-CDR3 for 2G2
TRREGIYDASWDY (SEQ ID NO: 30)

VH-CDR1 for C1C5
GYTFTNYG (SEQ ID NO: 31)

VH-CDR2 for C1C5
INTYSGEP (SEQ ID NO: 32)

VH-CDR3 for C1C5
VRQGDFDYEDAMD (SEQ ID NO: 33)

VL-CDR1 for CIEL huC1E1-V1 - huC1E1-V7 and huC1E1-V10
RASKSVDDSGISFMH (SEQ ID NO: 34)

VL-CDR2 for CIEL huC1E1-V1 - huC1E1-V7 and huC1E1-V10
AASNQGS (SEQ ID NO: 35)

VL-CDR3 for CIEL huC1E1-V1 - huC1E1-V7 and huC1E1-V10
HQTKEVPWT (SEQ ID NO: 36)

VL-CDR1 for D1F2
RASQDISNFLN (SEQ ID NO: 37)

VL-CDR2 for D1F2
YTSRLQS (SEQ ID NO: 38)

VL-CDR3 for D1F2
QQGSSLPWT (SEQ ID NO: 39)

VL-CDR1 for C1F5
RASQSISNNLH (SEQ ID NO: 40)

VL-CDR2 for C1F5
GSQSMS (SEQ ID NO: 41)

VL-CDR3 for C1F5
QQSNSWPLT (SEQ ID NO: 42)

VL-CDR1 for D1A1
RASQDISNYLN (SEQ ID NO: 43)

VL-CDR2 for D1A1
YTSRLHS (SEQ ID NO: 44)

| Description/Sequence/SEQ ID NO. |
| --- |

VL-CDR3 for D1A1
QQSNALPWT (SEQ ID NO: 45)

VL-CDR1 for D1F1
RASESVDNSGISFMN (SEQ ID NO: 46)

VL-CDR2 for D1F1
TASNQGS (SEQ ID NO: 47)

VL-CDR3 for D1F1
QQSYEVPWT (SEQ ID NO: 48)

VL-CDR1 for C1E2
KASQSVSNDVA (SEQ ID NO: 49)

VL-CDR2 for C1E2
YAFFIRYT (SEQ ID NO: 50)

VL-CDR3 for C1E2
QQDYSSPYT (SEQ ID NO: 51)

VL-CDR1 for C1A1
RASQDISNYLI (SEQ ID NO: 52)

VL-CDR2 for C1A1
YTSRLHS (SEQ ID NO: 53)

VL-CDR3 for C1A1
QQHKTLPWT (SEQ ID NO: 54)

VL-CDR1 for C1F4
KASQNVRTAVA (SEQ ID NO: 55)

VL-CDR2 for C1F4
LASNRHT (SEQ ID NO: 56)

VL-CDR3 for C1F4
LQHWNYPYT (SEQ ID NO: 57)

VL-CDR1 for D2C2
RASESVDNSGISFMN (SEQ ID NO: 58)

VL-CDR2 for D2C2
IASNHGS (SEQ ID NO: 59)

VL-CDR3 for D2C2
QQSYEVPWT (SEQ ID NO: 60)

VL-CDR1 for 2G2
RSSQSIIRSNGNTYLE (SEQ ID NO: 61)

VL-CDR2 for 2G2
KVSNRFS (SEQ ID NO: 62)

VL-CDR3 for 2G2
FQGSHVPWT (SEQ ID NO: 63)

VL-CDR1 for C1C5
RSSQSIVHSNGHIYLE (SEQ ID NO: 64)

VL-CDR2 for C1C5
KVSKRFS (SEQ ID NO: 65)

VL-CDR3 for C1C5
FQGSHGT (SEQ ID NO: 66)

VH for C1E1
EVMLVESGGGLVKPGGSLKLSCAASGFTFSSYLMSWVRQTPEKRLEWVATISGGGDTYFPD
SVKGRFTISRDNVKNNLYLQMSSLRSEDTALYYCVRFGGAGYYWYFDVWGAGTTVTVSS
(SEQ ID NO: 67)
GAAGTGATGCTGGTGGAGTCTGGGGGAGGGTTAGTGAAGCCTGGAGGGTCCCTGAAACTCTC
CTGTGCAGCCTCTGGATTCACGTTCAGTAGTTATCTTATGTCTTGGGTTCGCCAGACTCCGG
AGAAGAGGCTGGAGTGGGTCGCAACCATTAGTGGTGGTGGTGGTGACACCTACTTTCCAGAC
AGTGTGAAGGGTCGATTCACCATCTCCAGAGACAATGTCAAGAACAACCTGTACCTGCAAAT
GAGCAGTCTTAGGTCTGAGGACACGGCCTTGTATTACTGTGTAAGATTTGGGGGCGCTGGTT

| Description/Sequence/SEQ ID NO. |
|---|
| ACTACTGGTATTTCGATGTCTGGGGCGCAGGGACCACGGTCACCGTCTCCTCA (SEQ ID NO: 102) |
| |
| VH for huC1E1-V1, huC1E1-V3-huC1E1-V7<br>EVQLVESGGGVVQPGRSLRLSCAASGFTFSSYLMSWVRQAPGKGLEWVATISGGGGDTYFPD<br>SVKGRFTISRDNSKNTLYLQMNSLRAEDTAVYYCVRFGGAGYYWYFDVWGAGTLVTVSS<br>(SEQ ID NO: 68) |
| |
| VH for huC1E1-V2 and huC1E1-V10<br>EVQLVESGGGVVQPGRSLRLSCAASGFTFSSYLMSWVRQAPGKGLEWVATISGGGGDTYFPD<br>SVKGRFTISRDNSKNTLYLQMNSLRAEDTAVYYCVRFGGAGYYWYFDVWGQGTLVTVSS<br>(SEQ ID NO: 69)<br>GAGGTGCAGCTGGTGGAGTCTGGGGGAGGCGTGGTCCAGCCTGGGAGGTCCCTGAGACTCTC<br>CTGTGCAGCCTCTGGATTCACCTTCAGTAGCTATCTTATGTCCTGGGTCCGCCAGGCTCCAG<br>GCAAGGGGCTAGAGTGGGTGGCAACTATATCAGGTGGTGGAGGTGACACATACTTCCCAGAC<br>TCCGTGAAGGGCCGATTCACCATCTCCAGAGACAATTCCAAGAACACGCTGTATCTGCAAAT<br>GAACAGCCTGAGAGCTGAGGACACGGCTGTGTATTACTGTGTGAGATTCGGTGGTGCTGGTT<br>ACTACTGGTACTTTGACGTCTGGGGCCAAGGAACCCTGGTCACCGTCTCGAGT (SEQ ID NO: 103) |
| |
| VH for D1F2<br>EVMLVESGGGLVKPGGSLKLSCAASGFTFSSYTMSWVRQTPEKRLEWVATISGGGSNIYYPD<br>SVEGRFTVSRDNARNTLYLHMSSLRSEDTALYYCVLNYAYAMDYWGQGTSVTVSS (SEQ ID NO: 70)<br>GAAGTGATGCTGGTGGAGTCTGGGGGAGGCTTAGTGAAGCCTGGAGGGTCCCTGAAACTCTC<br>CTGTGCAGCCTCTGGATTCACTTTCAGTAGCTATACCATGTCTTGGGTTCGCCAGACTCCGG<br>AGAAGAGGCTGGAGTGGGTCGCAACCATTAGTGGTGGTGGTAGTAACATCTACTATCCAGAC<br>AGTGTGGAGGGTCGATTCACCGTCTCCAGAGACAATGCCAGGAACACCCTGTACCTGCATAT<br>GAGCAGTCTGAGGTCTGAGGACACGGCCTTATATTACTGTGTCCTTAACTACGCCTATGCTA<br>TGGACTACTGGGGTCAAGGAACCTCAGTCACCGTCTCCTCA (SEQ ID NO: 104) |
| |
| VH for C1F5<br>EVQLVESGGGLVKPGGSLKLSCAASGFAFSSYDMSWVRQTPEKRLEWVAYITGGGSSSFYPD<br>TVKGRFTISRDNSKNTLYLQMTSLRSEDTAMYYCASPYLSYFDYWGQGTTLTVSS (SEQ ID NO: 71)<br>GAAGTGCAGCTGGTGGAGTCTGGGGGAGGCTTAGTGAAGCCTGGAGGGTCCCTGAAACTCTC<br>CTGTGCAGCCTCTGGATTCGCTTTCAGTAGCTATGACATGTCTTGGGTTCGCCAGACTCCGG<br>AGAAGAGGCTGGAGTGGGTCGCATACATTACTGGTGGTGGTAGTAGTTCCTTCTATCCAGAC<br>ACTGTGAAGGGCCGATTCACCATCTCCAGAGACAATTCCAAGAACACCCTGTATTTGCAAAT<br>GACCAGTCTGAGGTCTGAGGACACAGCCATGTATTACTGTGCAAGCCCCTACTTATCCTACT<br>TTGACTACTGGGGCCAAGGCACCACTCTCACAGTCTCCTCA (SEQ ID NO: 105) |
| |
| VH for D1A1<br>EVMLVESGGGLVKPGGSLKLSCAASGFTFSNYAMSWVRQTPEKRLEWVATISGGGGNIYYPD<br>SVKGRFTISRDNARNTLYLQMSSLRSEDTALYYCASPYANYVWYLDVWGAGTTVTVSS<br>(SEQ ID NO: 72)<br>GAAGTGATGCTGGTGGAGTCTGGGGGAGGCTTAGTGAAGCCTGGAGGGTCCCTGAAACTCTC<br>CTGTGCAGCCTCTGGATTCACTTTCAGTAACTATGCCATGTCTTGGGTTCGCCAGACTCCGG<br>AGAAGAGGCTGGAGTGGGTCGCAACCATTAGTGGTGGTGGTGGTAACATCTACTATCCAGAC<br>AGTGTGAAGGGTCGATTCACCATCTCCAGAGACAATGCCAGGAACACCCTGTACCTGCAAAT<br>GAGCAGTCTGAGGTCTGAGGACACGGCCTTGTATTATTGTGCAAGCCCGTATGCTAACTACG<br>TATGGTACCTCGATGTCTGGGGCGCAGGGACCACGGTCACCGTCTCCTCA (SEQ ID NO: 106) |
| |
| VH for D1F1<br>EVMLVESGGGLVKPGGSLKLSCAASGFTFSSNTMSWVRQTPEKRLEWVAAISGGGVNTYYPD<br>SVKGRFTISRDNARNTLYLQMSSLRSEDTALYYCARHGNYNYYGMDYWGQGTSVTVSS<br>(SEQ ID NO: 73)<br>GAAGTGATGCTGGTGGAGTCTGGGGGAGGCTTAGTGAAGCCTGGAGGGTCCCTGAAACTCTC<br>CTGTGCAGCCTCTGGATTCACTTTCAGTAGCAATACCATGTCTTGGGTTCGCCAGACTCCGG<br>AGAAGAGGCTGGAGTGGGTCGCAGCCATTAGTGGTGGTGGTGTTAACACCTACTATCCAGAC<br>AGTGTGAAGGGTCGATTCACCATCTCCAGAGACAATGCCAGGAACACCCTGTACCTGCAAAT<br>GAGCAGTCTGAGGTCTGAGGACACGGCCCTGTATTACTGTGCAAGACATGGTAACTACAATT<br>ACTATGGTATGGACTACTGGGGTCAAGGAACCTCAGTCACCGTCTCCTCA (SEQ ID NO: 107) |
| |
| VH for C1E2<br>QVQLQQSGAELVRPGTSVKISCKASGYTFTNYWLGWVKQRPGHGLEWIGDIYPGGGYTNYN<br>ENFKGKATLTADTSSSTAYMQLSSLTSEDSAVFFCARGYGTNYWYFDVWGAGTTVTVSS<br>(SEQ ID NO: 74)<br>CAGGTCCAGTTGCAGCAGTCTGGAGCTGAGCTGGTAAGGCCTGGGACTTCAGTGAAGATATC<br>CTGCAAGGCTTCTGGCTACACCTTCACTAACTACTGGCTAGGTTGGGTAAAACAGAGGCCTG<br>GACATGGACTTGAGTGGATTGGAGATATTTACCCTGGAGGTGGTTATACTAACTACAATGAG<br>AACTTCAAGGGCAAGGCCACACTGACTGCAGACACATCCTCCAGCACTGCCTACATGCAGCT<br>CAGTAGCCTGACATCTGAGGACTCTGCTGTCTTTTTCTGTGCAAGAGGCTACGGTACTAATT<br>ACTGGTACTTCGATGTCTGGGGCGCAGGGACCACGGTCACCGTCTCCTCA (SEQ ID NO: 108) |

| Description/Sequence/SEQ ID NO. |
| --- |

VH for C1A1
QVTLKESGPGILKPSQTLSLTCSFSGFSLSTSGMGVGWIRQPSGKGLEWLAHIWWDDDKFYN
PSLKSQLTISKDTSRNQVFLKITSVDTADTATYYCARTGGFITTGYWYFDVWGAGTTVTVSS
(SEQ ID NO: 75)
CAAGTTACTCTAAAAGAGTCTGGCCCTGGGATATTGAAGCCCTCACAGACCCTCAGTCTGAC
TTGTTCTTTCTCTGGGTTTTCACTGAGCACTTCTGGTATGGGTGTAGGCTGGATTCGTCAGC
CTTCAGGGAAGGGTCTGGAGTGGCTGGCACACATTTGGTGGGATGATGATAAGTTCTATAAC
CCATCCCTGAAGAGCCAGCTCACAATCTCCAAGGATACCTCCAGAAACCAGGTTTTCCTCAA
GATCACCAGTGTGGACACTGCAGATACTGCCACTTACTACTGTGCTCGAACCGGGGGGTTTA
TTACTACGGGCTACTGGTACTTCGATGTCTGGGGCGCAGGGACCACGGTCACCGTCTCCTCA
(SEQ ID NO: 109)

VH for C1F4
QVQLQQSGAELVRPGVSVKISCKGSGYKFTDYAMHWVRQSHAKSLEWIGIISTYSGDVSFNQ
NFKGKATMTVDKSSSTAYMELARLTSEDSAIYYCSRLGITAGFAYWGQGTLVTVSA (SEQ
ID NO: 76)
CAGGTCCAGCTGCAACAGTCTGGGGCTGAGCTGGTGAGGCCTGGGGTCTCAGTGAAGATTTC
CTGCAAGGGTTCTGGCTACAAATTCACTGATTATGCTATGCACTGGGTGAGGCAGAGTCATG
CAAAGAGTCTAGAGTGGATTGGAATTATTAGTACTTACTCTGGTGACGTTAGTTTCAACCAG
AACTTCAAGGGCAAGGCCACAATGACTGTAGACAAATCCTCCAGCACAGCCTATATGGAACT
TGCCAGACTGACATCTGAGGATTCTGCCATCTATTACTGTTCAAGACTGGGGATTACGGCGG
GGTTTGCTTACTGGGGCCAAGGGACTCTGGTCACTGTCTCTGCA (SEQ ID NO: 110)

VH for D2C2
EVMLVESGGGLVKPGGSLKLSCAASGFTFSSNTMSWVRQTPEKRLEWVAAISGGGVDTYYPD
SVKGRFTISRDNARNTLYLQMSSLRSEDTALYYCARHGNYNYYGMDYWGQGTSVTVSS
(SEQ ID NO: 77)
GAAGTGATGCTGGTGGAGTCTGGGGGAGGCTTAGTGAAGCCTGGAGGGTCCCTGAAACTCTC
CTGTGCAGCCTCTGGATTCACTTTCAGTAGCAATACCATGTCTTGGGTTCGCCAGACTCCGG
AGAAGAGGCTGGAGTGGGTCGCAGCCATTAGTGGTGGTGGTGTTGACACCTACTATCCAGAC
AGTGTGAAGGGTCGATTCACCATCTCCAGAGACAATGCCAGGAACACCCTGTACCTGCAAAT
GAGCAGTCTGAGGTCTGAGGACACGGCCCTGTATTACTGTGCAAGACATGGTAACTACAATT
ACTATGGTATGGACTACTGGGGTCAAGGAACCTCAGTCACCGTCTCCTCA (SEQ ID NO:
111)

VH for 2G2
EVQLVESGGDLVKPGGSLKLSCTASGFTFSYYGMSWVRQTPDKRLEWVATISSGSSFTYSPD
SVKGRFTISRDNAKNTLYLQMNSLKSEDTAIYYCTRREGIYDASWDYSMDYWGQGTSVTVSS
(SEQ ID NO: 78)
GAGGTGCAACTGGTGGAGTCTGGGGGAGACTTAGTGAAGCCTGGAGGGTCCCTGAAACTCTC
CTGTACAGCCTCTGGATTCACTTTCAGTTACTATGGCATGTCTTGGGTTCGCCAGACTCCAG
ACAAGAGGCTGGAATGGGTCGCAACCATTAGTAGTGGTAGTAGTTTCACCTACTCTCCAGAC
AGTGTGAAGGGGCGATTCACCATCTCCAGAGACAATGCCAAGAACACCCTGTACCTACAAAT
GAACAGTCTGAAGTCTGAGGACACAGCCATTTATTACTGTACAAGACGAGAGGGGATCTATG
ATGCTTCCTGGGATTATTCTATGGACTACTGGGGTCAAGGAACCTCAGTCACCGTCTCCTCA
(SEQ ID NO: 112)

VH for C1C5
QIQLVQSGPELKKPGETVKISCKASGYTFTNYGINWVKQAPGKGLKWMGWINTYSGEPTYSD
DFKGRFAFSLETSASTAYLQINNLKNEDTSTYFCVRQGDFDYEDAMDYWGQGTSVTVSS
(SEQ ID NO: 79)
CAGATCCAGTTGGTGCAGTCAGGACCTGAGCTGAAGAAGCCTGGAGAGACAGTCAAGATCTC
CTGCAAGGCTTCTGGGTATACCTTCACAAACTATGGAATAAACTGGGTGAAGCAGGCTCCAG
GAAAGGGTTTAAAGTGGATGGGCTGGATAAACACCTATAGTGGAGAGCCAACATATTCTGAT
GACTTCAAGGGACGCTTTGCCTTCTCTTTGGAAACCTCTGCCAGCACTGCCTATTTGCAGAT
CAACAACCTCAAAAATGAGGACACGTCTACATATTTCTGTGTAAGACAGGGGGACTTTGATT
ACGAGGATGCTATGGACTACTGGGGTCAAGGAACCTCAGTCACCGTCTCCTCA (SEQ ID
NO: 113)

VL for C1E1
DIVLTQSPASLAVSLGQRATISCRASKSVDDSGISFMHWFQQKPGQPPKLLIYAASNQGSGV
PARFRGSGSGTDFSLNIIIPMEEDDTAMYFCHQTKEVPWTFGGGTKLEIK (SEQ ID NO:
80)
GACATTGTGCTGACCCAATCTCCAGCTTCTTTGGCTGTGTCTCTAGGGCAGAGGGCCACCAT
CTCCTGCAGAGCCAGCAAAAGTGTTGATGATTCTGGCATTAGTTTTATGCACTGGTTCCAAC
AGAAACCAGGACAGCCACCCAAACTCCTCATCTATGCTGCATCCAACCAAGGATCCGGGGTC
CCTGCCAGGTTTCGTGGCAGTGGGTCTGGGACAGACTTCAGCCTCAACATCCATCCTATGGA
GGAGGATGATACTGCAATGTATTTCTGTCACCAAACTAAGGAGGTTCCGTGGACGTTCGGTG
GAGGCACCAAGCTGGAAATCAAA (SEQ ID NO: 114)

VL for huC1E1-V1 and huC1E1-V2
EIVLTQSPATLSLSPGERATLSCRASKSVDDSGISFMHWFQQKPGQPPRLLIYAASNQGSGV
PARFSGSGSGTDFTLTISSLEPEDFAVYFCHQTKEVPWTFGQGTKVEIK (SEQ ID NO:
81)

| Description/Sequence/SEQ ID NO. |
|---|

VL for huC1E1-V3
EIVLTQSPATLSLSPGERATLSCRASKSVDDSGISFMHWYQQKPGQPPRLLIYAASNQGSGV
PARFSGSGSGTDFTLTISSLEPEDFAVYFCHQTKEVPWTFGQGTKVEIK (SEQ ID NO:
82)

VL for huC1E1-V4
EIVLTQSPATLSLSPGERATLSCRASKSVDDSGISFMHWFQQKPGQAPRLLIYAASNQGSGV
PARFSGSGSGTDFTLTISSLEPEDFAVYFCHQTKEVPWTFGQGTKVEIK (SEQ ID NO:
83)

VL for huC1E1-V5
EIVLTQSPATLSLSPGERATLSCRASKSVDDSGISFMHWFQQKPGQPPRLLIYAASNQGSGI
PARFSGSGSGTDFTLTISSLEPEDFAVYFCHQTKEVPWTFGQGTKVEIK (SEQ ID NO:
84)

VL for huC1E1-V6
EIVLTQSPATLSLSPGERATLSCRASKSVDDSGISFMHWFQQKPGQPPRLLIYAASNQGSGV
PARFSGSGSGTDFTLTISSLEPEDFAVYYCHQTKEVPWTFGQGTKVEIK (SEQ ID NO:
85)

VL for huC1E1-V7 and huC1E1-V10
EIVLTQSPATLSLSPGERATLSCRASKSVDDSGISFMHWYQQKPGQAPRLLIYAASNQGSGI
PARFSGSGSGTDFTLTISSLEPEDFAVYYCHQTKEVPWTFGQGTKVEIK (SEQ ID NO:
86)
GAAATTGTGTTGACACAGTCTCCAGCCACCCTGTCTTTGTCTCCAGGGGAAAGAGCCACCCT
CTCCTGCAGGGCCAGTAAGTCTGTTGACGACAGTGGTATCAGCTTCATGCACTGGTATCAAC
AGAAACCTGGCCAGGCTCCCAGGCTCCTCATCTATGCTGCATCCAACCAGGGCTCTGGCATC
CCAGCCAGGTTCAGTGGCAGTGGGTCTGGGACAGACTTCACTCTCACCATCAGCAGCCTAGA
GCCTGAAGATTTTGCAGTTTATTACTGTCATCAGACTAAGGAGGTGCCTTGGACGTTCGGCC
AAGGGACCAAGGTGGAGATCAAA (SEQ ID NO: 115)

VL for D1F2
DIQMTQTTSSLSASLGDRVTISCRASQDISNFLNWYQQKPDGTVKLLIYYTSRLQSGVPSRF
SGTGSGTDYSLTISNLEQEDLATYFCQQGSSLPWTFGGGTKLEIK (SEQ ID NO: 87)
GATATCCAGATGACACAGACTACATCCTCCCTGTCTGCCTCTCTGGGAGACAGAGTCACCAT
CAGTTGCAGGGCCAGTCAGGACATTAGCAATTTTTTAAACTGGTATCAGCAGAAACCAGATG
GAACTGTTAAACTCCTGATCTACTACACATCAAGATTACAGTCAGGAGTCCCATCAAGGTTC
AGTGGCACTGGGTCTGGGACAGATTATTCTCTCACCATTAGCAACCTGGAACAAGAAGATCT
TGCCACTTACTTTTGCCAACAGGGTAGTTCGCTTCCGTGGACGTTCGGTGGAGGCACCAAGC
TGGAAATCAAA (SEQ ID NO: 116)

VL for C1F5
DIVLTQSPATLSVTPGDSVSLSCRASQSISNNLHWYQQKSHESPRLLIKYGSQSMSGIPSRF
SGSGSGTDFTLVINSVETEDFGMYFCQQSNSWPLTFGAGTKLELK (SEQ ID NO: 88)
GATATTGTGCTAACTCAGTCTCCAGCCACCCTGTCTGTGACTCCAGGAGATAGCGTCAGTCT
TTCCTGCAGGGCCAGCCAAAGTATTAGCAACAACCTACACTGGTATCAACAAAAATCACATG
AGTCTCCAAGGCTTCTCATCAAGTATGGTTCCCAGTCCATGTCTGGGATCCCCTCCAGGTTC
AGTGGCAGTGGATCAGGGACAGATTTCACTCTCGTTATCAACAGTGTGGAGACTGAAGATTT
TGGAATGTATTTCTGTCAACAGAGTAACAGCTGGCCTCTCACGTTCGGTGCTGGGACCAAGC
TGGAGCTGAAA (SEQ ID NO: 117)

VL for D1A1
DIQMTQTTSSLSASLGDRVTISCRASQDISNYLNWYQQKPDGTVKLLIYYTSRLHSGVPSRF
SGSGSGTDFSLTISNLEEEDIATYFCQQSNALPWTFGGGTKLEIK (SEQ ID NO: 89)
GATATCCAGATGACACAGACTACATCCTCCCTGTCTGCCTCTCTGGGAGACAGAGTCACCAT
CAGTTGCAGGGCAAGTCAGGACATTAGCAATTATTTAAACTGGTATCAGCAGAAACCAGATG
GAACTGTTAAACTCCTGATCTACTACACATCAAGATTACACTCAGGAGTCCCATCAAGGTTC
AGTGGCAGTGGGTCTGGAACAGATTTTCTCTCACCATTAGCAACCTGGAAGAAGAAGATATT
GCCACTTACTTTTGCCAACAGAGTAATGCGCTTCCGTGGACGTTCGGTGGAGGCACCAAAC
TGGAAATCAAA (SEQ ID NO: 118)

VL for D1F1
DIVLTQSPASLVVSLGQRATISCRASESVDNSGISFMNWFQQKPGQPPKWYTASNQGSGVPA
RFSGSGSGTDFSLNIFIPMEEDDSAMYFCQQSYEVPWTFGGGTKLEIK (SEQ ID NO:
90)
GACATTGTGCTGACCCAATCTCCAGCTTCTTTGGTTGTGTCTCTAGGGCAGAGGGCCACCAT
CTCCTGCAGAGCCAGCGAAAGTGTTGATAATTCTGGCATTAGTTTTATGAACTGGTTCCAAC
AGAAACCAGGACAGCCACCCAAACTCCTCATCTATACTGCATCCAACCAAGGATCCGGGGTC
CCTGCCAGGTTTAGTGGCAGTGGGTCTGGGACAGACTTCAGCCTCAACATCCATCCTATGGA
GGAGGATGATTCTGCAATGTATTTCTGTCAGCAAAGTTATGAGGTTCCTTGGACGTTCGGTG
GAGGCACCAAGCTGGAAATCAAA (SEQ ID NO: 119)

VL for C1E2
SIVMTQTPKFLLVSAGDRVTITCKASQSVSNDVAWYQQKPGQSPKLLIYYAFHRYTGVPDRF
TGSGYGTDFTFTISTVQAEDLAVYFCQQDYSSPYTFGGGTKLEIK (SEQ ID NO: 91)
AGTATTGTGATGACCCAGACTCCCAAATTCCTGCTTGTATCAGCAGGAGACAGGGTTACCAT

| Description/Sequence/SEQ ID NO. |
| --- |

AACCTGCAAGGCCAGTCAGAGTGTGAGTAATGATGTAGCTTGGTACCAACAGAAGCCAGGGC
AGTCTCCTAAACTGCTGATATACTATGCATTTCATCGCTACACTGGAGTCCCTGATCGCTTC
ACTGGCAGTGGATATGGGACGGATTTCACTTTTCACCATCAGCACTGTGCAGGCTGAAGACCT
GGCAGTTTATTTCTGTCAGCAGGATTATAGCTCTCCGTACACGTTCGGAGGGGGGACCAAGC
TGGAAATAAAA (SEQ ID NO: 120)

VL for C1A1
DIQMTQTTSSLSASLGDRVTISCRASQDISNYLIWYQQKTDGTLKLLIYYTSRLHSGVPSRF
SGSGSGTDYSLTISNLEQEDIATYFCQQHKTLPWTFGGGTKLEIK (SEQ ID NO: 92)
GATATCCAGATGACACAGACTACATCCTCCCTGTCTGCCTCTCTGGGAGACAGAGTCACCAT
CAGTTGCAGGGCAAGTCAGGACATTAGCAATTATTTAATCTGGTATCAGCAGAAAACAGATG
GAACTCTTAAACTCCTGATCTACTACACATCAAGATTACACTCAGGAGTCCCATCAAGGTTC
AGTGGCAGTGGGTCTGGAACAGATTATTCTCTCACCATTAGCAACCTGGAGCAAGAAGATAT
TGCCACTTACTTTTGCCAGCAGCATAAAACGCTTCCGTGGACGTTCGGTGGAGGCACCAAGC
TGGAAATCAAA (SEQ ID NO: 121)

VL for C1F4
DIVMTQSQKFMSTSVGDRVTITCKASQNVRTAVAWYQQKPGQSPKALIYLASNRHTGVPDRF
TGSGSGTDFTLTISNVQSKDLADYFCLQHWNYPYTFGGGTKLEIK (SEQ ID NO: 93)
GACATTGTGATGACCCAGTCTCAAAAATTCATGTCCACATCAGTAGGAGACAGGGTCACCAT
CACCTGCAAGGCCAGTCAGAATGTTCGTACTGCTGTAGCCTGGTATCAACAGAAACCAGGGC
AGTCTCCTAAAGCACTGATTTACTTGGCATCCAACCGGCACACTGGAGTCCCTGATCGCTTC
ACAGGCAGTGGATCTGGGACAGATTTCACTCTCACCATTAGCAATGTGCAATCTAAAGACCT
GGCAGATTATTTCTGTCTGCAACATTGGAATTATCCGTACACGTTCGGAGGGGGGACCAAGC
TGGAAATAAAA (SEQ ID NO: 122)

VL for D2C2
DIVLTQSPASLAVSLGQRATISCRASESVDNSGISFMNWFQQKPGQSPKLLIYIASNHGSGV
PARFSGSGSGTDFSLNIFIPMEEDDSAMYFCQQSYEVPWTFGGGTKLEIK (SEQ ID NO:
94)
GACATTGTGCTGACCCAATCTCCAGCTTCTTTGGCTGTGTCTCTAGGGCAGAGGGCCACCAT
CTCCTGCAGAGCCAGCGAAAGTGTTGATAATTCTGGCATTAGTTTTATGAACTGGTTCCAAC
AGAAACCAGGACAGTCACCCAAATCCTCATCTATATTGCATCCAACCACGGATCCGGGGTC
CCTGCCAGGTTTAGTGGCAGTGGGTCTGGGACAGACTTCAGCCTCAACATCATCCTATGGA
GGAGGATGATTCTGCAATGTATTTCTGTCAGCAAAGTTATGAGGTTCCTTGGACGTTCGGTG
GAGGCACCAAGCTGGAAATCAAA (SEQ ID NO: 123)

VL for 2G2
DVLMTQTPLSLPVSLGDQASISCRSSQSIIRSNGNTYLEWYLQKPGQSPKWYKVSNRFSGVP
DRFSGSGSGTDFTLKISRVEADDLGLYYCFQGSHVPWTFGGGTKLEIK (SEQ ID NO:
95)
GATGTTTTGATGACCCAAACTCCACTCTCCCTGCCTGTCAGTCTTGGAGATCAAGCCTCCAT
CTCTTGCAGATCTAGTCAGAGCATTATACGTAGTAATGGAAACACCTATTTAGAATGGTACC
TGCAGAAACCAGGCCAGTCTCCAAAGCTCCTGATCTACAAAGTTTCCAACCGATTTTCTGGG
GTCCCAGACAGGTTCAGTGGCAGTGGATCAGGGACAGATTTCACACTCAAGATCAGCAGAGT
GGAGGCTGACGATCTGGGACTTTATTACTGCTTTCAAGGTTCACATGTTCCGTGGACGTTCG
GTGGAGGCACCAAGCTGGAAATCAAA (SEQ ID NO: 124)

VL for C1C5
DVLMTQSPLSLPVSLGDQASISCRSSQSIVHSNGHIYLEWYLQKPGQSPKWYKVSKRFSGVP
DRFSGSGSGTDFTLKISRVEAEDLGVYYCFQGSHGTFGGGTKLEIK (SEQ ID NO: 96)
GATGTTTTGATGACCCAAAGTCCACTCTCCCTGCCTGTCAGTCTTGGAGATCAAGCCTCCAT
CTCTTGCAGATCTAGTCAGAGTATTGTACATAGTAATGGACACATCTATTTAGAATGGTACC
TGCAGAAACCAGGCCAGTCTCCAAAGCTCCTGATCTACAAAGTTTCCAAGCGATTTTCTGGG
GTCCCAGACAGGTTCAGTGGCAGTGGATCAGGGACAGATTTCACACTCAAGATCAGCAGAGT
GGAGGCTGAGGATCTGGGAGTTTATTACTGCTTTCAAGGTTCACATGGGACGTTCGGTGGAG
GCACCAAGCTGGAAATCAAA (SEQ ID NO: 125)

human IgG1 heavy chain constant region
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK (SEQ ID NO: 97)
GCTAGCACCAAGGGCCCATCGGTCTTCCCCCTGGCACCCTCCTCCAAGAGCACCTCTGGGGG
CACAGCGGCCCTGGGCTGCCTGGTCAAGGACTACTTCCCCGAACCGGTGACGGTGTCGTGGA
ACTCAGGCGCCCTGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCAGACCTACATCTG
CAACGTGAATCACAAGCCCAGCAACACCAAGGTGGACAAGAAAGTTGAGCCCAAATCTTGTG
ACAAAACTCACACATGCCCACCGTGCCCAGCACCTGAACTCCTGGGGGGACCGTCAGTCTTC
CTCTTCCCCCCAAAACCCAAGGACACCCTCATGATCTCCCGGACCCCTGAGGTCACATGCGT
GGTGGTGGACGTGAGCCACGAAGACCCTGAGGTCAAGTTCAACTGGTACGTGGACGGCGTGG
AGGTGCATAATGCCAAGACAAAGCCGCGGGAGGAGCAGTACAACAGCACGTACCGTGTGGTC
AGCGTCCTCACCGTCCTGCACCAGGACTGGCTGAATGGCAAGGAGTACAAGTGCAAGGTCTC
CAACAAAGCCCTCCCAGCCCCCATCGAGAAAACCATCTCCAAAGCCAAAGGGCAGCCCCGAG
AACCACAGGTGTACACCCTGCCCCCATCCCGGGAGGAGATGACCAAGAACCAGGTCAGCCTG

| Description/Sequence/SEQ ID NO. |
|---|
| ACCTGCCTGGTCAAAGGCTTCTATCCCAGCGACATCGCCGTGGAGTGGGAGAGCAATGGGCA<br>GCCGGAGAACAACTACAAGACCACGCCTCCCGTGCTGGACTCCGACGGCTCCTTCTTCCTCT<br>ACAGCAAGCTCACCGTGGACAAGAGCAGGTGGCAGCAGGGGAACGTCTTCTCATGCTCCGTG<br>ATGCATGAGGCTCTGCACAACCACTACACGCAGAAGAGCCTCTCCCTGTCTCCGGGTAAA<br>(SEQ ID NO: 126)<br><br>human kappa light chain constant region<br>RTVAAPSVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC (SEQ ID NO: 98)<br>CGTACGGTGGCGGCGCCATCTGTCTTCATCTTCCCGCCATCTGATGAGCAGTTGAA<br>ATCTGGAACTGCCTCTGTTGTGTGCCTGCTGAATAACTTCTATCCCAGAGAGGCCA<br>AAGTACAGTGGAAGGTGGATAACGCCCTCCAATCGGGTAACTCCCAGGAGAGTGT<br>CACAGAGCAGGACAGCAAGGACAGCACCTACAGCCTCAGCAGCACCCTGACGCT<br>GAGCAAAGCAGACTACGAGAAACACAAAGTCTACGCCTGCGAAGTCACCCATCA<br>GGGCCTGAGCTCGCCCGTCACAAAGAGCTTCAACAGGGGAGAGTGT (SEQ ID NO:<br>127)<br><br>human IgG1 heavy chain CH1 region<br>ASTKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKKV (SEQ ID NO: 99)<br>Gcctccaccaagggcccatcggtcttccccctggcaccctcctccaagagcacctctggggg<br>cacagcggccctgggctgcctggtcaaggactacttccccgaaccggtgacggtgtcgtgga<br>actcaggcgccctgaccagcggcgtgcacaccttcccggctgtcctacagtcctcaggactc<br>tactccctcagcagcgtggtgaccgtgccctccagcagcttgggcacccagacctacatct<br>gcaacgtgaatcacaagcccagcaacaccaaggtggacaagaaagtt<br>(SEQ ID NO: 128)<br><br>human PD-1-Fc<br>LDSPDRPWNPPTFSPALLVVTEGDNATFTCSFSNTSESFVLNWYRMSPSNQTDKLAAFPEDRS<br>QPGQDCRFRVTQLPNGRDFHMSVVRARRNDSGTYLCGAISLAPKAQIKESLRAELRVTERRAE<br>VPTAHPSPSPRPAGQFQEPKSCDKTHTCPPCPAPELLGGPSVFLFPPKPKDTLMISRTPEVTC<br>VVVDVSHEDPEVKFNAVYVDGVEVHNAKTKPREEQYNSTYRVVSVLTVLHQDWLNGKEYKCKV<br>SNKALPAPIEKTISKAKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHNHYTQKSLSL (SEQ<br>ID NO: 100)<br><br>human PD-L1-Fc<br>FTVTVPKDLYVVEYGSNMTIECKFPVEKQLDLAALIVYWEMEDKNIIQFVHGEEDLKVQHSS<br>YRQRARLLKDQLSLGNAALQITDVKLQDAGVYRCMISYGGADYKRITVKVNAPYNKINQRIL<br>VVDPVTSEHELTCQAEGYPKAEVIWTSSDHQVLSGKTTTTNSKREEKLFNVTSTLRINTTTN<br>EIFYCTFRRLDPEENHTAELVIPELPLAHPPNERTEPKSCDKTHTCPPCPAPELLGGPSVFL<br>FPPKPKDTLMISRTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSREEMTKNQVSLT<br>CLVKGFYPSDIAVEWESNGQPENNYKTTPPVLDSDGSFFLYSKLTVDKSRWQQGNVFSCSVM<br>HEALHNHYTQKSLSLSPGK (SEQ ID NO: 101)<br><br>Heavy chain constant region for mouse antibodies<br>AKTTPPSVYPLAPGSAAQTNSMVTLGCLVKGYFPEPVTVTWNSGSLSSGVHTFPAVL<br>QSDLYTLSSSVTVPSSTWPSETVTCNVAHPASSTKVDKKIVPRDCGCKPCICTVPES<br>SVFIFPPKPKDVLTITLTPKVTCVVVDISKDDPEVQFSWFVDDVEVHTAQTQPREEQF<br>NSTFRSVSELPIMHQDWLNGKEFKCRVNSAAFPAPIEKTISKTKGRPKAPQVYTIPPPK<br>EQMAKDKVSLTCMITDFFPEDITVEWQWNGQPAENYKNTQPIMDTDGSYFVYSKLN<br>VQKSNWEAGNTFTCSVLHEGLHNHHTEKSLSHSPGK (SEQ ID NO: 129)<br><br>Light chain constant region for mouse antibodies<br>RADAAPTVSIFPPSSEQLTSGGASVVCFLNNFYPKDINVKWKIDGSERQNGVLNSWT<br>DQDSKDSTYSMSSTLTLTKDEYERHNSYTCEATHKTSTSPIVKSFNRGEC (SEQ ID NO:<br>130) |

SEQ ID NOs: 1-101, 129 and 130: amino acid sequence; SEQ ID NOs: 102-128: nucleotide sequence

---

What is claimed is:

1. A genetically modified Herpes Simplex Virus Type 1 (HSV-1), comprising a polynucleotide encoding a Fab of an anti-PD-1 antibody,
 wherein the anti-PD-1 antibody comprises a heavy chain variable region comprising heavy chain CDR1, CDR2, and CDR3 regions, and a light chain variable region comprising light chain CDR1, CDR2, and CDR3 regions, and
 wherein the heavy chain CDR1, CDR2, and CDR3 regions and the light chain CDR1, CDR2, and CDR3 regions comprise amino acid sequences set forth in SEQ ID NOs: 1, 2, 3, 34, 35, and 36, respectively.

2. The genetically modified HSV-1 of claim 1, wherein the heavy chain and the light chain variable regions comprise amino acid sequences having at least 80%, 85%, 90%, 95%, 98% 99% or 100% identity to SEQ ID NOs: 67 and 80, respectively.

3. The genetically modified HSV-1 of claim 1, wherein the anti-PD-1 antibody comprises a heavy chain constant region having an amino acid sequence having at least 80%, 85%, 90%, 95%, 98% 99% or 100% identity to SEQ ID NOs: 97, 99 or 129, and/or a light chain constant region having an amino acid sequence having at least 80%, 85%, 90%, 95%, 98% 99% or 100% identity to SEQ ID NOs: 98 or 130.

4. The genetically modified HSV-1 of claim 1, wherein the Fab of an anti-PD-1 antibody comprises a mouse heavy chain variable domain, a human IgG1 CH1 constant domain, a mouse light chain variable domain, and a human kappa light chain constant domain, having sequences set forth in SEQ ID NOs: 67, 99, 80, and 98, respectively.

5. The genetically modified HSV-1 of claim 1, further comprising a human IL-12 gene.

6. The genetically modified HSV-1 of claim 1, wherein an inverted repeat region is removed.

7. The genetically modified HSV-1 of claim 6, wherein the inverted repeat region is replaced by a human IL-12 gene.

8. The genetically modified HSV-1 of claim 1, wherein the polynucleotide encoding the Fab is inserted between UL3 and UL4.

* * * * *